United States Patent
Gieffers et al.

(10) Patent No.: US 10,683,338 B2
(45) Date of Patent: Jun. 16, 2020

(54) SINGLE-CHAIN TL1A RECEPTOR AGONIST PROTEINS

(71) Applicant: Apogenix AG, Heidelberg (DE)

(72) Inventors: Christian Gieffers, Dossenheim (DE); Oliver Hill, Neckarsteinach (DE); Meinolf Thiemann, Schriesheim (DE); Tim Schnyder, Igersheim (DE)

(73) Assignee: Apogenix AG, Heidelberg (DE)

( * ) Notice: Subject to any disclaimer, the term of this patent is extended or adjusted under 35 U.S.C. 154(b) by 0 days.

(21) Appl. No.: 15/958,180

(22) Filed: Apr. 20, 2018

(65) Prior Publication Data

US 2018/0244753 A1 Aug. 30, 2018

Related U.S. Application Data

(63) Continuation of application No. PCT/EP2016/075574, filed on Oct. 24, 2016.

(60) Provisional application No. 62/247,671, filed on Oct. 28, 2015.

(51) Int. Cl.
| | |
|---|---|
| *C07K 14/52* | (2006.01) |
| *C07K 16/46* | (2006.01) |
| *C07H 21/04* | (2006.01) |
| *C12N 15/63* | (2006.01) |
| *C07K 14/705* | (2006.01) |
| *A61K 38/00* | (2006.01) |

(52) U.S. Cl.
CPC ........ *C07K 14/70575* (2013.01); *A61K 38/00* (2013.01); *C07K 2319/00* (2013.01); *C07K 2319/22* (2013.01); *C07K 2319/30* (2013.01); *C07K 2319/32* (2013.01); *C07K 2319/35* (2013.01); *C07K 2319/74* (2013.01)

(58) Field of Classification Search
None
See application file for complete search history.

(56) References Cited

U.S. PATENT DOCUMENTS

2013/0211051 A1  8/2013  Sun et al.

FOREIGN PATENT DOCUMENTS

| WO | 2005103077 A1 | 11/2005 |
| WO | 2009000538 A1 | 12/2008 |
| WO | 2009007120 A2 | 1/2009 |
| WO | 2010010051 A1 | 1/2010 |
| WO | 2013092983 A2 | 6/2013 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Samia Q. Khan et al, "Cloning, Expression, and Functional Characterization of TL1A-Ig", The Journal of Immunology, vol. 190, No. 4, Jan. 14, 2013, pp. 1540-1550.
Tengchuan Jin et al, "X-ray crystal structure of TNF ligand family member TL1A at 2.1Å", Biochemical and Biophysical Research Communications, vol. 364, No. 1, Oct. 22, 2007, pp. 1-6.
International Search Report dated Jan. 5, 2017 issued in PCT/EP2016/075574.

* cited by examiner

*Primary Examiner* — Christine J Saoud
*Assistant Examiner* — Jon M Lockard
(74) *Attorney, Agent, or Firm* — Viola T. Kung; Perkins Coie LLP

(57) ABSTRACT

Provided herein are specific TL1A receptor agonist proteins, nucleic acids encoding the same, and methods of treating a subject having a TL1A-associated disease or disorder. The TL1A receptor agonist proteins provided herein comprise three soluble TL1A domains and an Fc fragment. The TL1A receptor agonist proteins are substantially non-aggregating and suitable for therapeutic, diagnostic and/or research applications.

11 Claims, 6 Drawing Sheets

Specification includes a Sequence Listing.

SEQUENCE LISTING

```
<160> NUMBER OF SEQ ID NOS: 43

<210> SEQ ID NO 1
<211> LENGTH: 251
<212> TYPE: PRT
<213> ORGANISM: Homo sapiens
<220> FEATURE:
<223> OTHER INFORMATION: wt-TL1A

<400> SEQUENCE: 1

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60
```

Ala Cys Val Gln Phe Gln Ala Leu Lys Gly Gln Glu Phe Ala Pro Ser
 65                  70                  75                  80

His Gln Gln Val Tyr Ala Pro Leu Arg Ala Asp Gly Asp Lys Pro Arg
                 85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 2
<211> LENGTH: 8
<212> TYPE: PRT
<213> ORGANISM: Artificial Sequence
<220> FEATURE:
<223> OTHER INFORMATION: linker

<400> SEQUENCE: 2

Gly Ser Gly Ser Gly Asn Gly Ser
1               5

<210> SEQ ID NO 3
<211> LENGTH: 8
<212> TYPE: PRT
<213> ORGANISM: Artificial Sequence
<220> FEATURE:
<223> OTHER INFORMATION: linker

<400> SEQUENCE: 3

Gly Ser Gly Ser Gly Ser Gly Ser
1               5

<210> SEQ ID NO 4
<211> LENGTH: 8
<212> TYPE: PRT
<213> ORGANISM: Artificial Sequence
<220> FEATURE:
<223> OTHER INFORMATION: linker

<400> SEQUENCE: 4

Gly Gly Ser Gly Ser Gly Ser Gly
1               5

<210> SEQ ID NO 5
<211> LENGTH: 6
<212> TYPE: PRT

```
<213> ORGANISM: Artificial Sequence
<220> FEATURE:
<223> OTHER INFORMATION: linker

<400> SEQUENCE: 5

Gly Gly Ser Gly Ser Gly
1               5

<210> SEQ ID NO 6
<211> LENGTH: 4
<212> TYPE: PRT
<213> ORGANISM: Artificial Sequence
<220> FEATURE:
<223> OTHER INFORMATION: linker

<400> SEQUENCE: 6

Gly Gly Ser Gly
1

<210> SEQ ID NO 7
<211> LENGTH: 8
<212> TYPE: PRT
<213> ORGANISM: Artificial Sequence
<220> FEATURE:
<223> OTHER INFORMATION: linker

<400> SEQUENCE: 7

Gly Gly Ser Gly Asn Gly Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

Gly Gly Asn Gly Ser Gly Ser Gly
1               5

<210> SEQ ID NO 9
<211> LENGTH: 6
<212> TYPE: PRT
<213> ORGANISM: Artificial Sequence
<220> FEATURE:
<223> OTHER INFORMATION: linker

<400> SEQUENCE: 9

Gly Gly Asn Gly Ser Gly
1               5

<210> SEQ ID NO 10
<211> LENGTH: 6
<212> TYPE: PRT
<213> ORGANISM: Artificial Sequence
<220> FEATURE:
<223> OTHER INFORMATION: linker

<400> SEQUENCE: 10

Gly Ser Gly Ser Gly Ser
1               5

<210> SEQ ID NO 11
<211> LENGTH: 4
<212> TYPE: PRT
<213> ORGANISM: Artificial Sequence
```

```
<220> FEATURE:
<223> OTHER INFORMATION: linker

<400> SEQUENCE: 11

Gly Ser Gly Ser
1

<210> SEQ ID NO 12
<211> LENGTH: 3
<212> TYPE: PRT
<213> ORGANISM: Artificial Sequence
<220> FEATURE:
<223> OTHER INFORMATION: linker

<400> SEQUENCE: 12

Gly Ser Gly
1

<210> SEQ ID NO 13
<211> LENGTH: 218
<212> TYPE: PRT
<213> ORGANISM: Homo sapiens
<220> FEATURE:
<223> OTHER INFORMATION: IGG1 Fc mutein N297S

<400> SEQUENCE: 13

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Ser Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 14
<211> LENGTH: 217
<212> TYPE: PRT
<213> ORGANISM: Homo sapiens
<220> FEATURE:
```

<223> OTHER INFORMATION: wt-IGG1 Fc

<400> SEQUENCE: 14

```
Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 15
<211> LENGTH: 758
<212> TYPE: PRT
<213> ORGANISM: Artificial Sequence
<220> FEATURE:
<223> OTHER INFORMATION: PROTEIN A (TL1A RBDs of Seq39 fused to deglyco Fc)

<400> SEQUENCE: 15

```
Met Glu Thr Asp Thr Leu Leu Val Phe Val Leu Leu Trp Val Pro
1               5                   10                  15

Ala Gly Asn Gly Asp Lys Pro Arg Ala His Leu Thr Val Arg Gln
            20                  25                  30

Thr Pro Thr Gln His Phe Lys Asn Gln Phe Pro Ala Leu His Trp Glu
        35                  40                  45

His Glu Leu Gly Leu Ala Phe Thr Lys Asn Arg Met Asn Tyr Thr Asn
    50                  55                  60

Lys Phe Leu Leu Ile Pro Glu Ser Gly Asp Tyr Phe Ile Tyr Ser Gln
65                  70                  75                  80

Val Thr Phe Arg Gly Met Thr Ser Glu Cys Ser Glu Ile Arg Gln Ala
                85                  90                  95

Gly Arg Pro Asn Lys Pro Asp Ser Ile Thr Val Val Ile Thr Lys Val
            100                 105                 110

Thr Asp Ser Tyr Pro Glu Pro Thr Gln Leu Leu Met Gly Thr Lys Ser
```

```
            115                 120                 125
Val Cys Glu Val Gly Ser Asn Trp Phe Gln Pro Ile Tyr Leu Gly Ala
130                 135                 140

Met Phe Ser Leu Gln Glu Gly Asp Lys Leu Met Val Asn Val Ser Asp
145                 150                 155                 160

Ile Ser Leu Val Asp Tyr Thr Lys Glu Asp Lys Thr Phe Phe Gly Ala
                165                 170                 175

Phe Leu Leu Gly Ser Gly Ser Gly Asn Gly Ser Pro Arg Ala His Leu
                180                 185                 190

Thr Val Val Arg Gln Thr Pro Thr Gln His Phe Lys Asn Gln Phe Pro
                195                 200                 205

Ala Leu His Trp Glu His Glu Leu Gly Leu Ala Phe Thr Lys Asn Arg
210                 215                 220

Met Asn Tyr Thr Asn Lys Phe Leu Leu Ile Pro Glu Ser Gly Asp Tyr
225                 230                 235                 240

Phe Ile Tyr Ser Gln Val Thr Phe Arg Gly Met Thr Ser Glu Cys Ser
                245                 250                 255

Glu Ile Arg Gln Ala Gly Arg Pro Asn Lys Pro Asp Ser Ile Thr Val
                260                 265                 270

Val Ile Thr Lys Val Thr Asp Ser Tyr Pro Glu Pro Thr Gln Leu Leu
                275                 280                 285

Met Gly Thr Lys Ser Val Cys Glu Val Gly Ser Asn Trp Phe Gln Pro
290                 295                 300

Ile Tyr Leu Gly Ala Met Phe Ser Leu Gln Glu Gly Asp Lys Leu Met
305                 310                 315                 320

Val Asn Val Ser Asp Ile Ser Leu Val Asp Tyr Thr Lys Glu Asp Lys
                325                 330                 335

Thr Phe Phe Gly Ala Phe Leu Leu Gly Ser Gly Ser Pro Arg Ala His
                340                 345                 350

Leu Thr Val Val Arg Gln Thr Pro Thr Gln His Phe Lys Asn Gln Phe
                355                 360                 365

Pro Ala Leu His Trp Glu His Glu Leu Gly Leu Ala Phe Thr Lys Asn
370                 375                 380

Arg Met Asn Tyr Thr Asn Lys Phe Leu Leu Ile Pro Glu Ser Gly Asp
385                 390                 395                 400

Tyr Phe Ile Tyr Ser Gln Val Thr Phe Arg Gly Met Thr Ser Glu Cys
                405                 410                 415

Ser Glu Ile Arg Gln Ala Gly Arg Pro Asn Lys Pro Asp Ser Ile Thr
                420                 425                 430

Val Val Ile Thr Lys Val Thr Asp Ser Tyr Pro Glu Pro Thr Gln Leu
                435                 440                 445

Leu Met Gly Thr Lys Ser Val Cys Glu Val Gly Ser Asn Trp Phe Gln
450                 455                 460

Pro Ile Tyr Leu Gly Ala Met Phe Ser Leu Gln Glu Gly Asp Lys Leu
465                 470                 475                 480

Met Val Asn Val Ser Asp Ile Ser Leu Val Asp Tyr Thr Lys Glu Asp
                485                 490                 495

Lys Thr Phe Phe Gly Ala Phe Leu Leu Gly Ser Ser Ser Ser Ser Ser
                500                 505                 510

Ser Ser Gly Ser Cys Asp Lys Thr His Thr Cys Pro Pro Cys Pro Ala
                515                 520                 525

Pro Glu Leu Leu Gly Gly Pro Ser Val Phe Leu Phe Pro Pro Lys Pro
530                 535                 540
```

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
            580                 585                 590

Tyr Ser Ser Thr Tyr Arg Val Val Ser Val Leu Thr Val Leu His Gln
        595                 600                 605

Asp Trp Leu Asn Gly Lys Glu Tyr Lys Cys Lys Val Ser Asn Lys Ala
    610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Glu Glu Met Thr
                645                 650                 655

Lys Asn Gln Val Ser Leu Thr Cys Leu Val Lys Gly Phe Tyr Pro Ser
            660                 665                 670

Asp Ile Ala Val Glu Trp Glu Ser Asn Gly Gln Pro Glu Asn Asn Tyr
        675                 680                 685

Lys Thr Thr Pro Pro Val Leu Asp Ser Asp Gly Ser Phe Phe Leu Tyr
690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Ser Ser Ser Ser Ser Ala Trp Ser
            740                 745                 750

His Pro Gln Phe Glu Lys
        755

<210> SEQ ID NO 16
<211> LENGTH: 21
<212> TYPE: PRT
<213> ORGANISM: Artificial Sequence
<220> FEATURE:
<223> OTHER INFORMATION: hinge linker

<400> SEQUENCE: 16

Gly Ser Ser Ser Ser Ser Ser Gly Ser Cys Asp Lys Thr His
1               5                   10                  15

Thr Cys Pro Pro Cys
            20

<210> SEQ ID NO 17
<211> LENGTH: 20
<212> TYPE: PRT
<213> ORGANISM: Artificial Sequence
<220> FEATURE:
<223> OTHER INFORMATION: universal signal peptide

<400> SEQUENCE: 17

Met Glu Thr Asp Thr Leu Leu Val Phe Val Leu Leu Val Trp Val Pro
1               5                   10                  15

Ala Gly Asn Gly
            20

<210> SEQ ID NO 18
<211> LENGTH: 15
<212> TYPE: PRT

```
<213> ORGANISM: Artificial Sequence
<220> FEATURE:
<223> OTHER INFORMATION: serine linker with strep tag

<400> SEQUENCE: 18

Ser Ser Ser Ser Ser Ser Ala Trp Ser His Pro Gln Phe Glu Lys
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: hinge linker

<400> SEQUENCE: 19

Gly Ser Ser Ser Ser Ser Ser Gly Ser Cys Asp Lys Thr His Thr
1               5                   10                  15

Cys Pro Pro Cys
            20

<210> SEQ ID NO 20
<211> LENGTH: 19
<212> TYPE: PRT
<213> ORGANISM: Artificial Sequence
<220> FEATURE:
<223> OTHER INFORMATION: hinge linker

<400> SEQUENCE: 20

Gly Ser Ser Ser Ser Ser Gly Ser Cys Asp Lys Thr His Thr Cys
1               5                   10                  15

Pro Pro Cys

<210> SEQ ID NO 21
<211> LENGTH: 18
<212> TYPE: PRT
<213> ORGANISM: Artificial Sequence
<220> FEATURE:
<223> OTHER INFORMATION: hinge linker

<400> SEQUENCE: 21

Gly Ser Ser Ser Ser Gly Ser Cys Asp Lys Thr His Thr Cys Pro
1               5                   10                  15

Pro Cys

<210> SEQ ID NO 22
<211> LENGTH: 16
<212> TYPE: PRT
<213> ORGANISM: Artificial Sequence
<220> FEATURE:
<223> OTHER INFORMATION: hinge linker

<400> SEQUENCE: 22

Gly Ser Ser Ser Gly Ser Cys Asp Lys Thr His Thr Cys Pro Pro Cys
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: hinge linker

<400> SEQUENCE: 23

Gly Ser Ser Ser Gly Ser Cys Asp Lys Thr His Thr Cys Pro Pro Cys
```

-continued

```
1               5                   10                  15

Gly Ser

<210> SEQ ID NO 24
<211> LENGTH: 20
<212> TYPE: PRT
<213> ORGANISM: Artificial Sequence
<220> FEATURE:
<223> OTHER INFORMATION: hinge linker

<400> SEQUENCE: 24

Gly Ser Ser Ser Gly Ser Cys Asp Lys Thr His Thr Cys Pro Pro Cys
1               5                   10                  15

Gly Ser Gly Ser
            20

<210> SEQ ID NO 25
<211> LENGTH: 744
<212> TYPE: PRT
<213> ORGANISM: Artificial Sequence
<220> FEATURE:
<223> OTHER INFORMATION: Prot A (Seq15) without strep tag

<400> SEQUENCE: 25

Met Glu Thr Asp Thr Leu Leu Val Phe Val Leu Leu Trp Val Pro
1               5                   10                  15

Ala Gly Asn Gly Asp Lys Pro Arg Ala His Leu Thr Val Val Arg Gln
                20                  25                  30

Thr Pro Thr Gln His Phe Lys Asn Gln Phe Pro Ala Leu His Trp Glu
            35                  40                  45

His Glu Leu Gly Leu Ala Phe Thr Lys Asn Arg Met Asn Tyr Thr Asn
        50                  55                  60

Lys Phe Leu Leu Ile Pro Glu Ser Gly Asp Tyr Phe Ile Tyr Ser Gln
65                  70                  75                  80

Val Thr Phe Arg Gly Met Thr Ser Glu Cys Ser Glu Ile Arg Gln Ala
                85                  90                  95

Gly Arg Pro Asn Lys Pro Asp Ser Ile Thr Val Val Ile Thr Lys Val
            100                 105                 110

Thr Asp Ser Tyr Pro Glu Pro Thr Gln Leu Leu Met Gly Thr Lys Ser
        115                 120                 125

Val Cys Glu Val Gly Ser Asn Trp Phe Gln Pro Ile Tyr Leu Gly Ala
    130                 135                 140

Met Phe Ser Leu Gln Glu Gly Asp Lys Leu Met Val Asn Val Ser Asp
145                 150                 155                 160

Ile Ser Leu Val Asp Tyr Thr Lys Glu Asp Lys Thr Phe Phe Gly Ala
                165                 170                 175

Phe Leu Leu Gly Ser Gly Ser Gly Asn Gly Ser Pro Arg Ala His Leu
            180                 185                 190

Thr Val Val Arg Gln Thr Pro Thr Gln His Phe Lys Asn Gln Phe Pro
        195                 200                 205

Ala Leu His Trp Glu His Glu Leu Gly Leu Ala Phe Thr Lys Asn Arg
    210                 215                 220

Met Asn Tyr Thr Asn Lys Phe Leu Leu Ile Pro Glu Ser Gly Asp Tyr
225                 230                 235                 240

Phe Ile Tyr Ser Gln Val Thr Phe Arg Gly Met Thr Ser Glu Cys Ser
                245                 250                 255

Glu Ile Arg Gln Ala Gly Arg Pro Asn Lys Pro Asp Ser Ile Thr Val
```

```
              260                 265                 270
Val Ile Thr Lys Val Thr Asp Ser Tyr Pro Glu Pro Thr Gln Leu Leu
            275                 280                 285

Met Gly Thr Lys Ser Val Cys Glu Val Gly Ser Asn Trp Phe Gln Pro
        290                 295                 300

Ile Tyr Leu Gly Ala Met Phe Ser Leu Gln Glu Gly Asp Lys Leu Met
305                 310                 315                 320

Val Asn Val Ser Asp Ile Ser Leu Val Asp Tyr Thr Lys Glu Asp Lys
                325                 330                 335

Thr Phe Phe Gly Ala Phe Leu Leu Gly Ser Gly Ser Pro Arg Ala His
            340                 345                 350

Leu Thr Val Val Arg Gln Thr Pro Thr Gln His Phe Lys Asn Gln Phe
        355                 360                 365

Pro Ala Leu His Trp Glu His Glu Leu Gly Leu Ala Phe Thr Lys Asn
    370                 375                 380

Arg Met Asn Tyr Thr Asn Lys Phe Leu Leu Ile Pro Glu Ser Gly Asp
385                 390                 395                 400

Tyr Phe Ile Tyr Ser Gln Val Thr Phe Arg Gly Met Thr Ser Glu Cys
                405                 410                 415

Ser Glu Ile Arg Gln Ala Gly Arg Pro Asn Lys Pro Asp Ser Ile Thr
            420                 425                 430

Val Val Ile Thr Lys Val Thr Asp Ser Tyr Pro Glu Pro Thr Gln Leu
        435                 440                 445

Leu Met Gly Thr Lys Ser Val Cys Glu Val Gly Ser Asn Trp Phe Gln
    450                 455                 460

Pro Ile Tyr Leu Gly Ala Met Phe Ser Leu Gln Glu Gly Asp Lys Leu
465                 470                 475                 480

Met Val Asn Val Ser Asp Ile Ser Leu Val Asp Tyr Thr Lys Glu Asp
                485                 490                 495

Lys Thr Phe Phe Gly Ala Phe Leu Leu Gly Ser Ser Ser Ser Ser Ser
            500                 505                 510

Ser Ser Gly Ser Cys Asp Lys Thr His Thr Cys Pro Pro Cys Pro Ala
        515                 520                 525

Pro Glu Leu Leu Gly Gly Pro Ser Val Phe Leu Phe Pro Pro Lys Pro
    530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
            580                 585                 590

Tyr Ser Thr Tyr Arg Val Val Ser Val Leu Thr Val Leu His Gln
        595                 600                 605

Asp Trp Leu Asn Gly Lys Glu Tyr Lys Cys Lys Val Ser Asn Lys Ala
    610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Glu Glu Met Thr
                645                 650                 655

Lys Asn Gln Val Ser Leu Thr Cys Leu Val Lys Gly Phe Tyr Pro Ser
            660                 665                 670

Asp Ile Ala Val Glu Trp Glu Ser Asn Gly Gln Pro Glu Asn Asn Tyr
        675                 680                 685
```

```
Lys Thr Thr Pro Pro Val Leu Asp Ser Asp Gly Ser Phe Phe Leu Tyr
        690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
            740
```

<210> SEQ ID NO 26
<211> LENGTH: 743
<212> TYPE: PRT
<213> ORGANISM: Artificial Sequence
<220> FEATURE:
<223> OTHER INFORMATION: TL1A RBDs of Seq39 (+ signal peptide) fused to wt-Fc of Seq14

<400> SEQUENCE: 26

```
Met Glu Thr Asp Thr Leu Leu Val Phe Val Leu Leu Val Trp Val Pro
1               5                   10                  15

Ala Gly Asn Gly Asp Lys Pro Arg Ala His Leu Thr Val Val Arg Gln
            20                  25                  30

Thr Pro Thr Gln His Phe Lys Asn Gln Phe Pro Ala Leu His Trp Glu
        35                  40                  45

His Glu Leu Gly Leu Ala Phe Thr Lys Asn Arg Met Asn Tyr Thr Asn
    50                  55                  60

Lys Phe Leu Leu Ile Pro Glu Ser Gly Asp Tyr Phe Ile Tyr Ser Gln
65                  70                  75                  80

Val Thr Phe Arg Gly Met Thr Ser Glu Cys Ser Glu Ile Arg Gln Ala
                85                  90                  95

Gly Arg Pro Asn Lys Pro Asp Ser Ile Thr Val Val Ile Thr Lys Val
            100                 105                 110

Thr Asp Ser Tyr Pro Glu Pro Thr Gln Leu Leu Met Gly Thr Lys Ser
        115                 120                 125

Val Cys Glu Val Gly Ser Asn Trp Phe Gln Pro Ile Tyr Leu Gly Ala
    130                 135                 140

Met Phe Ser Leu Gln Glu Gly Asp Lys Leu Met Val Asn Val Ser Asp
145                 150                 155                 160

Ile Ser Leu Val Asp Tyr Thr Lys Glu Asp Lys Thr Phe Phe Gly Ala
                165                 170                 175

Phe Leu Leu Gly Ser Gly Ser Gly Asn Gly Ser Pro Arg Ala His Leu
            180                 185                 190

Thr Val Val Arg Gln Thr Pro Thr Gln His Phe Lys Asn Gln Phe Pro
        195                 200                 205

Ala Leu His Trp Glu His Glu Leu Gly Leu Ala Phe Thr Lys Asn Arg
    210                 215                 220

Met Asn Tyr Thr Asn Lys Phe Leu Leu Ile Pro Glu Ser Gly Asp Tyr
225                 230                 235                 240

Phe Ile Tyr Ser Gln Val Thr Phe Arg Gly Met Thr Ser Glu Cys Ser
                245                 250                 255

Glu Ile Arg Gln Ala Gly Arg Pro Asn Lys Pro Asp Ser Ile Thr Val
            260                 265                 270

Val Ile Thr Lys Val Thr Asp Ser Tyr Pro Glu Pro Thr Gln Leu Leu
        275                 280                 285

Met Gly Thr Lys Ser Val Cys Glu Val Gly Ser Asn Trp Phe Gln Pro
```

```
            290                 295                 300
Ile Tyr Leu Gly Ala Met Phe Ser Leu Gln Glu Gly Asp Lys Leu Met
305                 310                 315                 320

Val Asn Val Ser Asp Ile Ser Leu Val Asp Tyr Thr Lys Glu Asp Lys
                325                 330                 335

Thr Phe Phe Gly Ala Phe Leu Leu Gly Ser Gly Ser Pro Arg Ala His
                340                 345                 350

Leu Thr Val Val Arg Gln Thr Pro Thr Gln His Phe Lys Asn Gln Phe
                355                 360                 365

Pro Ala Leu His Trp Glu His Glu Leu Gly Leu Ala Phe Thr Lys Asn
            370                 375                 380

Arg Met Asn Tyr Thr Asn Lys Phe Leu Leu Ile Pro Glu Ser Gly Asp
385                 390                 395                 400

Tyr Phe Ile Tyr Ser Gln Val Thr Phe Arg Gly Met Thr Ser Glu Cys
                405                 410                 415

Ser Glu Ile Arg Gln Ala Gly Arg Pro Asn Lys Pro Asp Ser Ile Thr
                420                 425                 430

Val Val Ile Thr Lys Val Thr Asp Ser Tyr Pro Glu Pro Thr Gln Leu
            435                 440                 445

Leu Met Gly Thr Lys Ser Val Cys Glu Val Gly Ser Asn Trp Phe Gln
            450                 455                 460

Pro Ile Tyr Leu Gly Ala Met Phe Ser Leu Gln Glu Gly Asp Lys Leu
465                 470                 475                 480

Met Val Asn Val Ser Asp Ile Ser Leu Val Asp Tyr Thr Lys Glu Asp
                485                 490                 495

Lys Thr Phe Phe Gly Ala Phe Leu Leu Gly Ser Ser Ser Ser Ser Ser
                500                 505                 510

Ser Ser Gly Ser Cys Asp Lys Thr His Thr Cys Pro Pro Cys Pro Ala
            515                 520                 525

Pro Pro Val Ala Gly Pro Ser Val Phe Leu Phe Pro Pro Lys Pro Lys
            530                 535                 540

Asp Thr Leu Met Ile Ser Arg Thr Pro Glu Val Thr Cys Val Val Val
545                 550                 555                 560

Asp Val Ser His Glu Asp Pro Glu Val Lys Phe Asn Trp Tyr Val Asp
                565                 570                 575

Gly Val Glu Val His Asn Ala Lys Thr Lys Pro Arg Glu Glu Gln Tyr
                580                 585                 590

Asn Ser Thr Tyr Arg Val Val Ser Val Leu Thr Val Leu His Gln Asp
            595                 600                 605

Trp Leu Asn Gly Lys Glu Tyr Lys Cys Lys Val Ser Asn Lys Gly Leu
            610                 615                 620

Pro Ser Ser Ile Glu Lys Thr Ile Ser Lys Ala Lys Gly Gln Pro Arg
625                 630                 635                 640

Glu Pro Gln Val Tyr Thr Leu Pro Pro Ser Arg Glu Glu Met Thr Lys
                645                 650                 655

Asn Gln Val Ser Leu Thr Cys Leu Val Lys Gly Phe Tyr Pro Ser Asp
                660                 665                 670

Ile Ala Val Glu Trp Glu Ser Asn Gly Gln Pro Glu Asn Asn Tyr Lys
            675                 680                 685

Thr Thr Pro Pro Val Leu Asp Ser Asp Gly Ser Phe Phe Leu Tyr Ser
            690                 695                 700

Lys Leu Thr Val Asp Lys Ser Arg Trp Gln Gln Gly Asn Val Phe Ser
705                 710                 715                 720
```

```
Cys Ser Val Met His Glu Ala Leu His Asn His Tyr Thr Gln Lys Ser
            725                 730                 735

Leu Ser Leu Ser Pro Gly Lys
            740

<210> SEQ ID NO 27
<211> LENGTH: 724
<212> TYPE: PRT
<213> ORGANISM: Artificial Sequence
<220> FEATURE:
<223> OTHER INFORMATION: TL1A RBDs of Seq39 fused to deglyco Fc

<400> SEQUENCE: 27

Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
            20                  25                  30

Leu Ala Phe Thr Lys Asn Arg Met Asn Tyr Thr Asn Lys Phe Leu Leu
        35                  40                  45

Ile Pro Glu Ser Gly Asp Tyr Phe Ile Tyr Ser Gln Val Thr Phe Arg
    50                  55                  60

Gly Met Thr Ser Glu Cys Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
    130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
        195                 200                 205

Asn Lys Phe Leu Leu Ile Pro Glu Ser Gly Asp Tyr Phe Ile Tyr Ser
    210                 215                 220

Gln Val Thr Phe Arg Gly Met Thr Ser Glu Cys Ser Glu Ile Arg Gln
225                 230                 235                 240

Ala Gly Arg Pro Asn Lys Pro Asp Ser Ile Thr Val Val Ile Thr Lys
                245                 250                 255

Val Thr Asp Ser Tyr Pro Glu Pro Thr Gln Leu Leu Met Gly Thr Lys
            260                 265                 270

Ser Val Cys Glu Val Gly Ser Asn Trp Phe Gln Pro Ile Tyr Leu Gly
        275                 280                 285

Ala Met Phe Ser Leu Gln Glu Gly Asp Lys Leu Met Val Asn Val Ser
    290                 295                 300

Asp Ile Ser Leu Val Asp Tyr Thr Lys Glu Asp Lys Thr Phe Phe Gly
305                 310                 315                 320

Ala Phe Leu Leu Gly Ser Gly Ser Pro Arg Ala His Leu Thr Val Val
                325                 330                 335
```

```
Arg Gln Thr Pro Thr Gln His Phe Lys Asn Gln Phe Pro Ala Leu His
                340                 345                 350

Trp Glu His Glu Leu Gly Leu Ala Phe Thr Lys Asn Arg Met Asn Tyr
            355                 360                 365

Thr Asn Lys Phe Leu Leu Ile Pro Glu Ser Gly Asp Tyr Phe Ile Tyr
370                 375                 380

Ser Gln Val Thr Phe Arg Gly Met Thr Ser Glu Cys Ser Glu Ile Arg
385                 390                 395                 400

Gln Ala Gly Arg Pro Asn Lys Pro Asp Ser Ile Thr Val Val Ile Thr
                405                 410                 415

Lys Val Thr Asp Ser Tyr Pro Glu Pro Thr Gln Leu Leu Met Gly Thr
            420                 425                 430

Lys Ser Val Cys Glu Val Gly Ser Asn Trp Phe Gln Pro Ile Tyr Leu
        435                 440                 445

Gly Ala Met Phe Ser Leu Gln Glu Gly Asp Lys Leu Met Val Asn Val
450                 455                 460

Ser Asp Ile Ser Leu Val Asp Tyr Thr Lys Glu Asp Lys Thr Phe Phe
465                 470                 475                 480

Gly Ala Phe Leu Leu Gly Ser Ser Ser Ser Ser Ser Ser Ser Gly Ser
                485                 490                 495

Cys Asp Lys Thr His Thr Cys Pro Pro Cys Pro Ala Pro Glu Leu Leu
            500                 505                 510

Gly Gly Pro Ser Val Phe Leu Phe Pro Pro Lys Pro Lys Asp Thr Leu
        515                 520                 525

Met Ile Ser Arg Thr Pro Glu Val Thr Cys Val Val Val Asp Val Ser
530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Ser Ser Thr
                565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Ala Lys Gly Gln Pro Arg Glu Pro Gln
610                 615                 620

Val Tyr Thr Leu Pro Pro Ser Arg Glu Glu Met Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
        675                 680                 685

Val Asp Lys Ser Arg Trp Gln Gln Gly Asn Val Phe Ser Cys Ser Val
690                 695                 700

Met His Glu Ala Leu His Asn His Tyr Thr Gln Lys Ser Leu Ser Leu
705                 710                 715                 720

Ser Pro Gly Lys

<210> SEQ ID NO 28
<211> LENGTH: 738
<212> TYPE: PRT
```

<213> ORGANISM: Artificial Sequence
<220> FEATURE:
<223> OTHER INFORMATION: TL1A RBDs of Seq39 fused to deglyco Fc (incl. strep tag)

<400> SEQUENCE: 28

Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
            20                  25                  30

Leu Ala Phe Thr Lys Asn Arg Met Asn Tyr Thr Asn Lys Phe Leu Leu
        35                  40                  45

Ile Pro Glu Ser Gly Asp Tyr Phe Ile Tyr Ser Gln Val Thr Phe Arg
50                  55                  60

Gly Met Thr Ser Glu Cys Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
        195                 200                 205

Asn Lys Phe Leu Leu Ile Pro Glu Ser Gly Asp Tyr Phe Ile Tyr Ser
210                 215                 220

Gln Val Thr Phe Arg Gly Met Thr Ser Glu Cys Ser Glu Ile Arg Gln
225                 230                 235                 240

Ala Gly Arg Pro Asn Lys Pro Asp Ser Ile Thr Val Val Ile Thr Lys
                245                 250                 255

Val Thr Asp Ser Tyr Pro Glu Pro Thr Gln Leu Leu Met Gly Thr Lys
            260                 265                 270

Ser Val Cys Glu Val Gly Ser Asn Trp Phe Gln Pro Ile Tyr Leu Gly
        275                 280                 285

Ala Met Phe Ser Leu Gln Glu Gly Asp Lys Leu Met Val Asn Val Ser
290                 295                 300

Asp Ile Ser Leu Val Asp Tyr Thr Lys Glu Asp Lys Thr Phe Phe Gly
305                 310                 315                 320

Ala Phe Leu Leu Gly Ser Gly Ser Pro Arg Ala His Leu Thr Val Val
                325                 330                 335

Arg Gln Thr Pro Thr Gln His Phe Lys Asn Gln Phe Pro Ala Leu His
            340                 345                 350

Trp Glu His Glu Leu Gly Leu Ala Phe Thr Lys Asn Arg Met Asn Tyr
        355                 360                 365

Thr Asn Lys Phe Leu Leu Ile Pro Glu Ser Gly Asp Tyr Phe Ile Tyr
370                 375                 380

```
Ser Gln Val Thr Phe Arg Gly Met Thr Ser Glu Cys Ser Glu Ile Arg
385                 390                 395                 400

Gln Ala Gly Arg Pro Asn Lys Pro Asp Ser Ile Thr Val Val Ile Thr
            405                 410                 415

Lys Val Thr Asp Ser Tyr Pro Glu Pro Thr Gln Leu Leu Met Gly Thr
        420                 425                 430

Lys Ser Val Cys Glu Val Gly Ser Asn Trp Phe Gln Pro Ile Tyr Leu
    435                 440                 445

Gly Ala Met Phe Ser Leu Gln Glu Gly Asp Lys Leu Met Val Asn Val
450                 455                 460

Ser Asp Ile Ser Leu Val Asp Tyr Thr Lys Glu Asp Lys Thr Phe Phe
465                 470                 475                 480

Gly Ala Phe Leu Leu Gly Ser Ser Ser Ser Ser Ser Ser Ser Gly Ser
                485                 490                 495

Cys Asp Lys Thr His Thr Cys Pro Pro Cys Pro Ala Pro Glu Leu Leu
            500                 505                 510

Gly Gly Pro Ser Val Phe Leu Phe Pro Pro Lys Pro Lys Asp Thr Leu
        515                 520                 525

Met Ile Ser Arg Thr Pro Glu Val Thr Cys Val Val Val Asp Val Ser
530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Ser Ser Thr
                565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Ala Lys Gly Gln Pro Arg Glu Pro Gln
610                 615                 620

Val Tyr Thr Leu Pro Pro Ser Arg Glu Glu Met Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
        675                 680                 685

Val Asp Lys Ser Arg Trp Gln Gln Gly Asn Val Phe Ser Cys Ser Val
690                 695                 700

Met His Glu Ala Leu His Asn His Tyr Thr Gln Lys Ser Leu Ser Leu
705                 710                 715                 720

Ser Pro Gly Ser Ser Ser Ser Ser Ser Ala Trp Ser His Pro Gln Phe
                725                 730                 735

Glu Lys

<210> SEQ ID NO 29
<211> LENGTH: 723
<212> TYPE: PRT
<213> ORGANISM: Artificial Sequence
<220> FEATURE:
<223> OTHER INFORMATION: TL1A RBDs of Seq39 fused to wt-Fc

<400> SEQUENCE: 29

Asp Lys Pro Arg Ala His Leu Thr Val Val Arg Gln Thr Pro Thr Gln
```

-continued

```
1               5               10              15

His Phe Lys Asn Gln Phe Pro Ala Leu His Trp Glu His Glu Leu Gly
                 20              25              30

Leu Ala Phe Thr Lys Asn Arg Met Asn Tyr Thr Asn Lys Phe Leu Leu
                 35              40              45

Ile Pro Glu Ser Gly Asp Tyr Phe Ile Tyr Ser Gln Val Thr Phe Arg
 50              55              60

Gly Met Thr Ser Glu Cys Ser Glu Ile Arg Gln Ala Gly Arg Pro Asn
 65              70              75              80

Lys Pro Asp Ser Ile Thr Val Val Ile Thr Lys Val Thr Asp Ser Tyr
                 85              90              95

Pro Glu Pro Thr Gln Leu Leu Met Gly Thr Lys Ser Val Cys Glu Val
                100             105             110

Gly Ser Asn Trp Phe Gln Pro Ile Tyr Leu Gly Ala Met Phe Ser Leu
                115             120             125

Gln Glu Gly Asp Lys Leu Met Val Asn Val Ser Asp Ile Ser Leu Val
                130             135             140

Asp Tyr Thr Lys Glu Asp Lys Thr Phe Phe Gly Ala Phe Leu Leu Gly
145             150             155             160

Ser Gly Ser Gly Asn Gly Ser Pro Arg Ala His Leu Thr Val Val Arg
                165             170             175

Gln Thr Pro Thr Gln His Phe Lys Asn Gln Phe Pro Ala Leu His Trp
                180             185             190

Glu His Glu Leu Gly Leu Ala Phe Thr Lys Asn Arg Met Asn Tyr Thr
                195             200             205

Asn Lys Phe Leu Leu Ile Pro Glu Ser Gly Asp Tyr Phe Ile Tyr Ser
                210             215             220

Gln Val Thr Phe Arg Gly Met Thr Ser Glu Cys Ser Glu Ile Arg Gln
225             230             235             240

Ala Gly Arg Pro Asn Lys Pro Asp Ser Ile Thr Val Val Ile Thr Lys
                245             250             255

Val Thr Asp Ser Tyr Pro Glu Pro Thr Gln Leu Leu Met Gly Thr Lys
                260             265             270

Ser Val Cys Glu Val Gly Ser Asn Trp Phe Gln Pro Ile Tyr Leu Gly
                275             280             285

Ala Met Phe Ser Leu Gln Glu Gly Asp Lys Leu Met Val Asn Val Ser
                290             295             300

Asp Ile Ser Leu Val Asp Tyr Thr Lys Glu Asp Lys Thr Phe Phe Gly
305             310             315             320

Ala Phe Leu Leu Gly Ser Gly Ser Pro Arg Ala His Leu Thr Val Val
                325             330             335

Arg Gln Thr Pro Thr Gln His Phe Lys Asn Gln Phe Pro Ala Leu His
                340             345             350

Trp Glu His Glu Leu Gly Leu Ala Phe Thr Lys Asn Arg Met Asn Tyr
                355             360             365

Thr Asn Lys Phe Leu Leu Ile Pro Glu Ser Gly Asp Tyr Phe Ile Tyr
                370             375             380

Ser Gln Val Thr Phe Arg Gly Met Thr Ser Glu Cys Ser Glu Ile Arg
385             390             395             400

Gln Ala Gly Arg Pro Asn Lys Pro Asp Ser Ile Thr Val Val Ile Thr
                405             410             415

Lys Val Thr Asp Ser Tyr Pro Glu Pro Thr Gln Leu Leu Met Gly Thr
                420             425             430
```

-continued

Lys Ser Val Cys Glu Val Gly Ser Asn Trp Phe Gln Pro Ile Tyr Leu
            435                 440                 445
Gly Ala Met Phe Ser Leu Gln Glu Gly Asp Lys Leu Met Val Asn Val
        450                 455                 460
Ser Asp Ile Ser Leu Val Asp Tyr Thr Lys Glu Asp Lys Thr Phe Phe
465                 470                 475                 480
Gly Ala Phe Leu Leu Gly Ser Ser Ser Ser Ser Ser Ser Ser Gly Ser
                485                 490                 495
Cys Asp Lys Thr His Thr Cys Pro Pro Cys Pro Ala Pro Pro Val Ala
            500                 505                 510
Gly Pro Ser Val Phe Leu Phe Pro Pro Lys Pro Lys Asp Thr Leu Met
        515                 520                 525
Ile Ser Arg Thr Pro Glu Val Thr Cys Val Val Val Asp Val Ser His
530                 535                 540
Glu Asp Pro Glu Val Lys Phe Asn Trp Tyr Val Asp Gly Val Glu Val
545                 550                 555                 560
His Asn Ala Lys Thr Lys Pro Arg Glu Glu Gln Tyr Asn Ser Thr Tyr
            565                 570                 575
Arg Val Val Ser Val Leu Thr Val Leu His Gln Asp Trp Leu Asn Gly
        580                 585                 590
Lys Glu Tyr Lys Cys Lys Val Ser Asn Lys Gly Leu Pro Ser Ser Ile
    595                 600                 605
Glu Lys Thr Ile Ser Lys Ala Lys Gly Gln Pro Arg Glu Pro Gln Val
610                 615                 620
Tyr Thr Leu Pro Pro Ser Arg Glu Glu Met Thr Lys Asn Gln Val Ser
625                 630                 635                 640
Leu Thr Cys Leu Val Lys Gly Phe Tyr Pro Ser Asp Ile Ala Val Glu
            645                 650                 655
Trp Glu Ser Asn Gly Gln Pro Glu Asn Asn Tyr Lys Thr Thr Pro Pro
        660                 665                 670
Val Leu Asp Ser Asp Gly Ser Phe Phe Leu Tyr Ser Lys Leu Thr Val
    675                 680                 685
Asp Lys Ser Arg Trp Gln Gln Gly Asn Val Phe Ser Cys Ser Val Met
690                 695                 700
His Glu Ala Leu His Asn His Tyr Thr Gln Lys Ser Leu Ser Leu Ser
705                 710                 715                 720
Pro Gly Lys

<210> SEQ ID NO 30
<211> LENGTH: 724
<212> TYPE: PRT
<213> ORGANISM: Artificial Sequence
<220> FEATURE:
<223> OTHER INFORMATION: Seq27 mutein with D93Q in RBD 1

<400> SEQUENCE: 30

Gln Lys Pro Arg Ala His Leu Thr Val Val Arg Gln Thr Pro Thr Gln
1               5                   10                  15
His Phe Lys Asn Gln Phe P

-continued

```
Gly Met Thr Ser Glu Cys Ser Glu Ile Arg Gln Ala Gly Arg Pro Asn
 65                  70                  75                  80

Lys Pro Asp Ser Ile Thr Val Val Ile Thr Lys Val Thr Asp Ser Tyr
                 85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
    130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
        195                 200                 205

Asn Lys Phe Leu Leu Ile Pro Glu Ser Gly Asp Tyr Phe Ile Tyr Ser
    210                 215                 220

Gln Val Thr Phe Arg Gly Met Thr Ser Glu Cys Ser Glu Ile Arg Gln
225                 230                 235                 240

Ala Gly Arg Pro Asn Lys Pro Asp Ser Ile Thr Val Val Ile Thr Lys
                245                 250                 255

Val Thr Asp Ser Tyr Pro Glu Pro Thr Gln Leu Leu Met Gly Thr Lys
            260                 265                 270

Ser Val Cys Glu Val Gly Ser Asn Trp Phe Gln Pro Ile Tyr Leu Gly
        275                 280                 285

Ala Met Phe Ser Leu Gln Glu Gly Asp Lys Leu Met Val Asn Val Ser
    290                 295                 300

Asp Ile Ser Leu Val Asp Tyr Thr Lys Glu Asp Lys Thr Phe Phe Gly
305                 310                 315                 320

Ala Phe Leu Leu Gly Ser Gly Ser Pro Arg Ala His Leu Thr Val Val
                325                 330                 335

Arg Gln Thr Pro Thr Gln His Phe Lys Asn Gln Phe Pro Ala Leu His
            340                 345                 350

Trp Glu His Glu Leu Gly Leu Ala Phe Thr Lys Asn Arg Met Asn Tyr
        355                 360                 365

Thr Asn Lys Phe Leu Leu Ile Pro Glu Ser Gly Asp Tyr Phe Ile Tyr
    370                 375                 380

Ser Gln Val Thr Phe Arg Gly Met Thr Ser Glu Cys Ser Glu Ile Arg
385                 390                 395                 400

Gln Ala Gly Arg Pro Asn Lys Pro Asp Ser Ile Thr Val Val Ile Thr
                405                 410                 415

Lys Val Thr Asp Ser Tyr Pro Glu Pro Thr Gln Leu Leu Met Gly Thr
            420                 425                 430

Lys Ser Val Cys Glu Val Gly Ser Asn Trp Phe Gln Pro Ile Tyr Leu
        435                 440                 445

Gly Ala Met Phe Ser Leu Gln Glu Gly Asp Lys Leu Met Val Asn Val
    450                 455                 460

Ser Asp Ile Ser Leu Val Asp Tyr Thr Lys Glu Asp Lys Thr Phe Phe
465                 470                 475                 480

Gly Ala Phe Leu Leu Gly Ser Ser Ser Ser Ser Ser Ser Ser Gly Ser
```

```
                  485                 490                 495

Cys Asp Lys Thr His Thr Cys Pro Pro Cys Pro Ala Pro Glu Leu Leu
            500                 505                 510

Gly Gly Pro Ser Val Phe Leu Phe Pro Pro Lys Pro Lys Asp Thr Leu
        515                 520                 525

Met Ile Ser Arg Thr Pro Glu Val Thr Cys Val Val Val Asp Val Ser
    530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Ser Ser Thr
                565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Ala Lys Gly Gln Pro Arg Glu Pro Gln
    610                 615                 620

Val Tyr Thr Leu Pro Pro Ser Arg Glu Glu Met Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
        675                 680                 685

Val Asp Lys Ser Arg Trp Gln Gln Gly Asn Val Phe Ser Cys Ser Val
    690                 695                 700

Met His Glu Ala Leu His Asn His Tyr Thr Gln Lys Ser Leu Ser Leu
705                 710                 715                 720

Ser Pro Gly Lys

<210> SEQ ID NO 31
<211> LENGTH: 730
<212> TYPE: PRT
<213> ORGANISM: Artificial Sequence
<220> FEATURE:
<223> OTHER INFORMATION: TL1A RBDs of Seq40 fused to deglyco Fc

<400> SEQUENCE: 31

Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
            20                  25                  30

Leu Ala Phe Thr Lys Asn Arg Met Asn Tyr Thr Asn Lys Phe Leu Leu
        35                  40                  45

Ile Pro Glu Ser Gly Asp Tyr Phe Ile Tyr Ser Gln Val Thr Phe Arg
    50                  55                  60

Gly Met Thr Ser Glu Cys Ser Glu Ile Arg Gln Ala Gly Arg Pro Asn
65              70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125
```

-continued

```
Gln Glu Gly Asp Lys Leu Met Val Asn Val Ser Asp Ile Ser Leu Val
130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Lys Pro Arg Ala His Leu Thr Val Val
                165                 170                 175

Arg Gln Thr Pro Thr Gln His Phe Lys Asn Gln Phe Pro Ala Leu His
            180                 185                 190

Trp Glu His Glu Leu Gly Leu Ala Phe Thr Lys Asn Arg Met Asn Tyr
        195                 200                 205

Thr Asn Lys Phe Leu Leu Ile Pro Glu Ser Gly Asp Tyr Phe Ile Tyr
210                 215                 220

Ser Gln Val Thr Phe Arg Gly Met Thr Ser Glu Cys Ser Glu Ile Arg
225                 230                 235                 240

Gln Ala Gly Arg Pro Asn Lys Pro Asp Ser Ile Thr Val Val Ile Thr
                245                 250                 255

Lys Val Thr Asp Ser Tyr Pro Glu Pro Thr Gln Leu Leu Met Gly Thr
            260                 265                 270

Lys Ser Val Cys Glu Val Gly Ser Asn Trp Phe Gln Pro Ile Tyr Leu
        275                 280                 285

Gly Ala Met Phe Ser Leu Gln Glu Gly Asp Lys Leu Met Val Asn Val
290                 295                 300

Ser Asp Ile Ser Leu Val Asp Tyr Thr Lys Glu Asp Lys Thr Phe Phe
305                 310                 315                 320

Gly Ala Phe Leu Leu Gly Ser Gly Ser Gly Asn Gly Ser Lys Pro Arg
                325                 330                 335

Ala His Leu Thr Val Val Arg Gln Thr Pro Thr Gln His Phe Lys Asn
            340                 345                 350

Gln Phe Pro Ala Leu His Trp Glu His Glu Leu Gly Leu Ala Phe Thr
        355                 360                 365

Lys Asn Arg Met Asn Tyr Thr Asn Lys Phe Leu Leu Ile Pro Glu Ser
370                 375                 380

Gly Asp Tyr Phe Ile Tyr Ser Gln Val Thr Phe Arg Gly Met Thr Ser
385                 390                 395                 400

Glu Cys Ser Glu Ile Arg Gln Ala Gly Arg Pro Asn Lys Pro Asp Ser
                405                 410                 415

Ile Thr Val Val Ile Thr Lys Val Thr Asp Ser Tyr Pro Glu Pro Thr
            420                 425                 430

Gln Leu Leu Met Gly Thr Lys Ser Val Cys Glu Val Gly Ser Asn Trp
        435                 440                 445

Phe Gln Pro Ile Tyr Leu Gly Ala Met Phe Ser Leu Gln Glu Gly Asp
450                 455                 460

Lys Leu Met Val Asn Val Ser Asp Ile Ser Leu Val Asp Tyr Thr Lys
465                 470                 475                 480

Glu Asp Lys Thr Phe Phe Gly Ala Phe Leu Leu Gly Ser Ser Ser Ser
                485                 490                 495

Ser Ser Ser Ser Gly Ser Cys Asp Lys Thr His Thr Cys Pro Pro Cys
            500                 505                 510

Pro Ala Pro Glu Leu Leu Gly Gly Pro Ser Val Phe Leu Phe Pro Pro
        515                 520                 525

Lys Pro Lys Asp Thr Leu Met Ile Ser Arg Thr Pro Glu Val Thr Cys
530                 535                 540
```

-continued

```
Val Val Val Asp Val Ser His Glu Asp Pro Glu Val Lys Phe Asn Trp
545                 550                 555                 560

Tyr Val Asp Gly Val Glu Val His Asn Ala Lys Thr Lys Pro Arg Glu
                565                 570                 575

Glu Gln Tyr Ser Ser Thr Tyr Arg Val Val Ser Val Leu Thr Val Leu
            580                 585                 590

His Gln Asp Trp Leu Asn Gly Lys Glu Tyr Lys Cys Lys Val Ser Asn
        595                 600                 605

Lys Ala Leu Pro Ala Pro Ile Glu Lys Thr Ile Ser Lys Ala Lys Gly
    610                 615                 620

Gln Pro Arg Glu Pro Gln Val Tyr Thr Leu Pro Pro Ser Arg Glu Glu
625                 630                 635                 640

Met Thr Lys Asn Gln Val Ser Leu Thr Cys Leu Val Lys Gly Phe Tyr
                645                 650                 655

Pro Ser Asp Ile Ala Val Glu Trp Glu Ser Asn Gly Gln Pro Glu Asn
            660                 665                 670

Asn Tyr Lys Thr Thr Pro Pro Val Leu Asp Ser Asp Gly Ser Phe Phe
        675                 680                 685

Leu Tyr Ser Lys Leu Thr Val Asp Lys Ser Arg Trp Gln Gln Gly Asn
    690                 695                 700

Val Phe Ser Cys Ser Val Met His Glu Ala Leu His Asn His Tyr Thr
705                 710                 715                 720

Gln Lys Ser Leu Ser Leu Ser Pro Gly Lys
                725                 730

<210> SEQ ID NO 32
<211> LENGTH: 721
<212> TYPE: PRT
<213> ORGANISM: Artificial Sequence
<220> FEATURE:
<223> OTHER INFORMATION: fusion protein of Seq30 with shorter hinge
      linker

<400> SEQUENCE: 32

Gln Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
                20                  25                  30

Leu Ala Phe Thr Lys Asn Arg Met Asn Tyr Thr Asn Lys Phe Leu Leu
            35                  40                  45

Ile Pro Glu Ser Gly Asp Tyr Phe Ile Tyr Ser Gln Val Thr Phe Arg
        50                  55                  60

Gly Met Thr Ser Glu Cys Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
    130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175
```

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
            195                 200                 205

Asn Lys Phe Leu Leu Ile Pro Glu Ser Gly Asp Tyr Phe Ile Tyr Ser
            210                 215                 220

Gln Val Thr Phe Arg Gly Met Thr Ser Glu Cys Ser Glu Ile Arg Gln
225                 230                 235                 240

Ala Gly Arg Pro Asn Lys Pro Asp Ser Ile Thr Val Val Ile Thr Lys
                245                 250                 255

Val Thr Asp Ser Tyr Pro Glu Pro Thr Gln Leu Leu Met Gly Thr Lys
            260                 265                 270

Ser Val Cys Glu Val Gly Ser Asn Trp Phe Gln Pro Ile Tyr Leu Gly
            275                 280                 285

Ala Met Phe Ser Leu Gln Glu Gly Asp Lys Leu Met Val Asn Val Ser
            290                 295                 300

Asp Ile Ser Leu Val Asp Tyr Thr Lys Glu Asp Lys Thr Phe Phe Gly
305                 310                 315                 320

Ala Phe Leu Leu Gly Ser Gly Ser Pro Arg Ala His Leu Thr Val Val
                325                 330                 335

Arg Gln Thr Pro Thr Gln His Phe Lys Asn Gln Phe Pro Ala Leu His
            340                 345                 350

Trp Glu His Glu Leu Gly Leu Ala Phe Thr Lys Asn Arg Met Asn Tyr
            355                 360                 365

Thr Asn Lys Phe Leu Leu Ile Pro Glu Ser Gly Asp Tyr Phe Ile Tyr
            370                 375                 380

Ser Gln Val Thr Phe Arg Gly Met Thr Ser Glu Cys Ser Glu Ile Arg
385                 390                 395                 400

Gln Ala Gly Arg Pro Asn Lys Pro Asp Ser Ile Thr Val Val Ile Thr
                405                 410                 415

Lys Val Thr Asp Ser Tyr Pro Glu Pro Thr Gln Leu Leu Met Gly Thr
            420                 425                 430

Lys Ser Val Cys Glu Val Gly Ser Asn Trp Phe Gln Pro Ile Tyr Leu
            435                 440                 445

Gly Ala Met Phe Ser Leu Gln Glu Gly Asp Lys Leu Met Val Asn Val
            450                 455                 460

Ser Asp Ile Ser Leu Val Asp Tyr Thr Lys Glu Asp Lys Thr Phe Phe
465                 470                 475                 480

Gly Ala Phe Leu Leu Gly Ser Ser Ser Ser Gly Ser Cys Asp Lys
                485                 490                 495

Thr His Thr Cys Pro Pro Cys Pro Ala Pro Glu Leu Leu Gly Gly Pro
            500                 505                 510

Ser Val Phe Leu Phe Pro Pro Lys Pro Lys Asp Thr Leu Met Ile Ser
            515                 520                 525

Arg Thr Pro Glu Val Thr Cys Val Val Val Asp Val Ser His Glu Asp
            530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Ser Ser Thr Tyr Arg Val
                565                 570                 575

Val Ser Val Leu Thr Val Leu His Gln Asp Trp Leu Asn Gly Lys Glu
            580                 585                 590

```
Tyr Lys Cys Lys Val Ser Asn Lys Ala Leu Pro Ala Pro Ile Glu Lys
            595                 600                 605

Thr Ile Ser Lys Ala Lys Gly Gln Pro Arg Glu Pro Gln Val Tyr Thr
    610                 615                 620

Leu Pro Pro Ser Arg Glu Glu Met Thr Lys Asn Gln Val Ser Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
            660                 665                 670

Asp Ser Asp Gly Ser Phe Phe Leu Tyr Ser Lys Leu Thr Val Asp Lys
        675                 680                 685

Ser Arg Trp Gln Gln Gly Asn Val Phe Ser Cys Ser Val Met His Glu
    690                 695                 700

Ala Leu His Asn His Tyr Thr Gln Lys Ser Leu Ser Leu Ser Pro Gly
705                 710                 715                 720

Lys

<210> SEQ ID NO 33
<211> LENGTH: 738
<212> TYPE: PRT
<213> ORGANISM: Artificial Sequence
<220> FEATURE:
<223> OTHER INFORMATION: RBD module of seq42 fused to Fc of seq13

<400> SEQUENCE: 33

Asp Gly Asp Lys Pro Arg Ala His Leu Thr Val Val Arg Gln Thr Pro
1               5                   10                  15

Thr Gln His Phe Lys Asn Gln Phe Pro Ala Leu His Trp Glu His Glu
            20                  25                  30

Leu Gly Leu Ala Phe Thr Lys Asn Arg Met Asn Tyr Thr Asn Lys Phe
        35                  40                  45

Leu Leu Ile Pro Glu Ser Gly Asp Tyr Phe Ile Tyr Ser Gln Val Thr
    50                  55                  60

Phe Arg Gly Met Thr Ser Glu Ser Ser Glu Ile Arg Gln Ala Gly Arg
65                  70                  75                  80

Pro Asn Lys Pro Asp Ser Ile Thr Val Val Ile Thr Lys Val Thr Asp
                85                  90                  95

Ser Tyr Pro Glu Pro Thr Gln Leu Leu Met Gly Thr Lys Ser Val Ser
            100                 105                 110

Glu Val Gly Ser Asn Trp Phe Gln Pro Ile Tyr Leu Gly Ala Met Phe
        115                 120                 125

Ser Leu Gln Glu Gly Asp Lys Leu Met Val Asn Val Ser Asp Ile Ser
    130                 135                 140

Leu Val Asp Tyr Thr Lys Glu Asp Lys Thr Phe Phe Gly Ala Phe Leu
145                 150                 155                 160

Leu Gly Ser Gly Ser Gly Asn Gly Ser Asp Gly Asp Lys Pro Arg Ala
                165                 170                 175

His Leu Thr Val Val Arg Gln Thr Pro Thr Gln His Phe Lys Asn Gln
            180                 185                 190

Phe Pro Ala Leu His Trp Glu His Glu Leu Gly Leu Ala Phe Thr Lys
        195                 200                 205

Asn Arg Met Asn Tyr Thr Asn Lys Phe Leu Leu Ile Pro Glu Ser Gly
    210                 215                 220

Asp Tyr Phe Ile Tyr Ser Gln Val Thr Phe Arg Gly Met Thr Ser Glu
```

```
            225                 230                 235                 240
Ser Ser Glu Ile Arg Gln Ala Gly Arg Pro Asn Lys Pro Asp Ser Ile
                    245                 250                 255

Thr Val Val Ile Thr Lys Val Thr Asp Ser Tyr Pro Glu Pro Thr Gln
                    260                 265                 270

Leu Leu Met Gly Thr Lys Ser Val Ser Glu Val Gly Ser Asn Trp Phe
                    275                 280                 285

Gln Pro Ile Tyr Leu Gly Ala Met Phe Ser Leu Gln Glu Gly Asp Lys
                    290                 295                 300

Leu Met Val Asn Val Ser Asp Ile Ser Leu Val Asp Tyr Thr Lys Glu
305                 310                 315                 320

Asp Lys Thr Phe Phe Gly Ala Phe Leu Leu Gly Ser Gly Ser Gly Asn
                    325                 330                 335

Gly Ser Asp Gly Asp Lys Pro Arg Ala His Leu Thr Val Val Arg Gln
                    340                 345                 350

Thr Pro Thr Gln His Phe Lys Asn Gln Phe Pro Ala Leu His Trp Glu
                    355                 360                 365

His Glu Leu Gly Leu Ala Phe Thr Lys Asn Arg Met Asn Tyr Thr Asn
        370                 375                 380

Lys Phe Leu Leu Ile Pro Glu Ser Gly Asp Tyr Phe Ile Tyr Ser Gln
385                 390                 395                 400

Val Thr Phe Arg Gly Met Thr Ser Glu Ser Glu Ile Arg Gln Ala
                    405                 410                 415

Gly Arg Pro Asn Lys Pro Asp Ser Ile Thr Val Val Ile Thr Lys Val
                    420                 425                 430

Thr Asp Ser Tyr Pro Glu Pro Thr Gln Leu Leu Met Gly Thr Lys Ser
            435                 440                 445

Val Ser Glu Val Gly Ser Asn Trp Phe Gln Pro Ile Tyr Leu Gly Ala
        450                 455                 460

Met Phe Ser Leu Gln Glu Gly Asp Lys Leu Met Val Asn Val Ser Asp
465                 470                 475                 480

Ile Ser Leu Val Asp Tyr Thr Lys Glu Asp Lys Thr Phe Phe Gly Ala
                485                 490                 495

Phe Leu Leu Gly Ser Ser Ser Ser Ser Ser Ser Gly Ser Cys Asp
                500                 505                 510

Lys Thr His Thr Cys Pro Pro Cys Pro Ala Pro Glu Leu Leu Gly Gly
            515                 520                 525

Pro Ser Val Phe Leu Phe Pro Pro Lys Pro Lys Asp Thr Leu Met Ile
            530                 535                 540

Ser Arg Thr Pro Glu Val Thr Cys Val Val Val Asp Val Ser His Glu
545                 550                 555                 560

Asp Pro Glu Val Lys Phe Asn Trp Tyr Val Asp Gly Val Glu Val His
                    565                 570                 575

Asn Ala Lys Thr Lys Pro Arg Glu Glu Gln Tyr Ser Thr Tyr Arg
                580                 585                 590

Val Val Ser Val Leu Thr Val Leu His Gln Asp Trp Leu Asn Gly Lys
            595                 600                 605

Glu Tyr Lys Cys Lys Val Ser Asn Lys Ala Leu Pro Ala Pro Ile Glu
        610                 615                 620

Lys Thr Ile Ser Lys Ala Lys Gly Gln Pro Arg Glu Pro Gln Val Tyr
625                 630                 635                 640

Thr Leu Pro Pro Ser Arg Glu Glu Met Thr Lys Asn Gln Val Ser Leu
                    645                 650                 655
```

-continued

Thr Cys Leu Val Lys Gly Phe Tyr Pro Ser Asp Ile Ala Val Glu Trp
            660                 665                 670

Glu Ser Asn Gly Gln Pro Glu Asn Asn Tyr Lys Thr Thr Pro Pro Val
        675                 680                 685

Leu Asp Ser Asp Gly Ser Phe Phe Leu Tyr Ser Lys Leu Thr Val Asp
    690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
                725                 730                 735

Gly Lys

<210> SEQ ID NO 34
<211> LENGTH: 721
<212> TYPE: PRT
<213> ORGANISM: Artificial Sequence
<220> FEATURE:
<223> OTHER INFORMATION: Protein A with shorter hinge linker

<400> SEQUENCE: 34

Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
            20                  25                  30

Leu Ala Phe Thr Lys Asn Arg Met Asn Tyr Thr Asn Lys Phe Leu Leu
        35                  40                  45

Ile Pro Glu Ser Gly Asp Tyr Phe Ile Tyr Ser Gln Val Thr Phe Arg
    50                  55                  60

Gly Met Thr Ser Glu Cys Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
    130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
        195                 200                 205

Asn Lys Phe Leu Leu Ile Pro Glu Ser Gly Asp Tyr Phe Ile Tyr Ser
    210                 215                 220

Gln Val Thr Phe Arg Gly Met Thr Ser Glu Cys Ser Glu Ile Arg Gln
225                 230                 235                 240

Ala Gly Arg Pro Asn Lys Pro Asp Ser Ile Thr Val Val Ile Thr Lys
                245                 250                 255

Val Thr Asp Ser Tyr Pro Glu Pro Thr Gln Leu Leu Met Gly Thr Lys
            260                 265                 270

```
Ser Val Cys Glu Val Gly Ser Asn Trp Phe Gln Pro Ile Tyr Leu Gly
        275                 280                 285

Ala Met Phe Ser Leu Gln Glu Gly Asp Lys Leu Met Val Asn Val Ser
        290                 295                 300

Asp Ile Ser Leu Val Asp Tyr Thr Lys Glu Asp Lys Thr Phe Phe Gly
305                 310                 315                 320

Ala Phe Leu Leu Gly Ser Gly Ser Pro Arg Ala His Leu Thr Val Val
                325                 330                 335

Arg Gln Thr Pro Thr Gln His Phe Lys Asn Gln Phe Pro Ala Leu His
                340                 345                 350

Trp Glu His Glu Leu Gly Leu Ala Phe Thr Lys Asn Arg Met Asn Tyr
        355                 360                 365

Thr Asn Lys Phe Leu Leu Ile Pro Glu Ser Gly Asp Tyr Phe Ile Tyr
        370                 375                 380

Ser Gln Val Thr Phe Arg Gly Met Thr Ser Glu Cys Ser Glu Ile Arg
385                 390                 395                 400

Gln Ala Gly Arg Pro Asn Lys Pro Asp Ser Ile Thr Val Val Ile Thr
                405                 410                 415

Lys Val Thr Asp Ser Tyr Pro Glu Pro Thr Gln Leu Leu Met Gly Thr
                420                 425                 430

Lys Ser Val Cys Glu Val Gly Ser Asn Trp Phe Gln Pro Ile Tyr Leu
        435                 440                 445

Gly Ala Met Phe Ser Leu Gln Glu Gly Asp Lys Leu Met Val Asn Val
        450                 455                 460

Ser Asp Ile Ser Leu Val Asp Tyr Thr Lys Glu Asp Lys Thr Phe Phe
465                 470                 475                 480

Gly Ala Phe Leu Leu Gly Ser Ser Ser Ser Gly Ser Cys Asp Lys
                485                 490                 495

Thr His Thr Cys Pro Pro Cys Pro Ala Pro Glu Leu Leu Gly Gly Pro
                500                 505                 510

Ser Val Phe Leu Phe Pro Pro Lys Pro Lys Asp Thr Leu Met Ile Ser
        515                 520                 525

Arg Thr Pro Glu Val Thr Cys Val Val Val Asp Val Ser His Glu Asp
530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Ser Ser Thr Tyr Arg Val
                565                 570                 575

Val Ser Val Leu Thr Val Leu His Gln Asp Trp Leu Asn Gly Lys Glu
                580                 585                 590

Tyr Lys Cys Lys Val Ser Asn Lys Ala Leu Pro Ala Pro Ile Glu Lys
        595                 600                 605

Thr Ile Ser Lys Ala Lys Gly Gln Pro Arg Glu Pro Gln Val Tyr Thr
        610                 615                 620

Leu Pro Pro Ser Arg Glu Glu Met Thr Lys Asn Gln Val Ser Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
                660                 665                 670

Asp Ser Asp Gly Ser Phe Phe Leu Tyr Ser Lys Leu Thr Val Asp Lys
                675                 680                 685

Ser Arg Trp Gln Gln Gly Asn Val Phe Ser Cys Ser Val Met His Glu
```

-continued

```
              690                 695                 700
Ala Leu His Asn His Tyr Thr Gln Lys Ser Leu Ser Leu Ser Pro Gly
705                 710                 715                 720

Lys

<210> SEQ ID NO 35
<211> LENGTH: 724
<212> TYPE: PRT
<213> ORGANISM: Artificial Sequence
<220> FEATURE:
<223> OTHER INFORMATION: mature Prot A - mutein C162S and C202S

<400> SEQUENCE: 35

Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
                20                  25                  30

Leu Ala Phe Thr Lys Asn Arg Met Asn Tyr Thr Asn Lys Phe Leu Leu
            35                  40                  45

Ile Pro Glu Ser Gly Asp Tyr Phe Ile Tyr Ser Gln Val Thr Phe Arg
50                  55                  60

Gly Met Thr Ser Glu Ser Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Ser Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
        195                 200                 205

Asn Lys Phe Leu Leu Ile Pro Glu Ser Gly Asp Tyr Phe Ile Tyr Ser
210                 215                 220

Gln Val Thr Phe Arg Gly Met Thr Ser Glu Ser Ser Glu Ile Arg Gln
225                 230                 235                 240

Ala Gly Arg Pro Asn Lys Pro Asp Ser Ile Thr Val Val Ile Thr Lys
                245                 250                 255

Val Thr Asp Ser Tyr Pro Glu Pro Thr Gln Leu Leu Met Gly Thr Lys
            260                 265                 270

Ser Val Ser Glu Val Gly Ser Asn Trp Phe Gln Pro Ile Tyr Leu Gly
        275                 280                 285

Ala Met Phe Ser Leu Gln Glu Gly Asp Lys Leu Met Val Asn Val Ser
290                 295                 300

Asp Ile Ser Leu Val Asp Tyr Thr Lys Glu Asp Lys Thr Phe Phe Gly
305                 310                 315                 320

Ala Phe Leu Leu Gly Ser Gly Ser Pro Arg Ala His Leu Thr Val Val
                325                 330                 335
```

Arg Gln Thr Pro Thr Gln His Phe Lys Asn Gln Phe Pro Ala Leu His
                340                 345                 350

Trp Glu His Glu Leu Gly Leu Ala Phe Thr Lys Asn Arg Met Asn Tyr
                355                 360                 365

Thr Asn Lys Phe Leu Leu Ile Pro Glu Ser Gly Asp Tyr Phe Ile Tyr
        370                 375                 380

Ser Gln Val Thr Phe Arg Gly Met Thr Ser Glu Ser Ser Glu Ile Arg
385                 390                 395                 400

Gln Ala Gly Arg Pro Asn Lys Pro Asp Ser Ile Thr Val Val Ile Thr
                405                 410                 415

Lys Val Thr Asp Ser Tyr Pro Glu Pro Thr Gln Leu Leu Met Gly Thr
                420                 425                 430

Lys Ser Val Ser Glu Val Gly Ser Asn Trp Phe Gln Pro Ile Tyr Leu
                435                 440                 445

Gly Ala Met Phe Ser Leu Gln Glu Gly Asp Lys Leu Met Val Asn Val
                450                 455                 460

Ser Asp Ile Ser Leu Val Asp Tyr Thr Lys Glu Asp Lys Thr Phe Phe
465                 470                 475                 480

Gly Ala Phe Leu Leu Gly Ser Ser Ser Ser Ser Ser Ser Ser Gly Ser
                485                 490                 495

Cys Asp Lys Thr His Thr Cys Pro Pro Cys Pro Ala Pro Glu Leu Leu
                500                 505                 510

Gly Gly Pro Ser Val Phe Leu Phe Pro Pro Lys Pro Lys Asp Thr Leu
                515                 520                 525

Met Ile Ser Arg Thr Pro Glu Val Thr Cys Val Val Val Asp Val Ser
                530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Ser Ser Thr
                565                 570                 575

Tyr Arg Val Val Ser Val Leu Thr Val Leu His Gln Asp Trp Leu Asn
                580                 585                 590

Gly Lys Glu Tyr Lys Cys Lys Val Ser Asn Lys Ala Leu Pro Ala Pro
                595                 600                 605

Ile Glu Lys Thr Ile Ser Lys Ala Lys Gly Gln Pro Arg Glu Pro Gln
                610                 615                 620

Val Tyr Thr Leu Pro Pro Ser Arg Glu Glu Met Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
                660                 665                 670

Pro Val Leu Asp Ser Asp Gly Ser Phe Phe Leu Tyr Ser Lys Leu Thr
                675                 680                 685

Val Asp Lys Ser Arg Trp Gln Gln Gly Asn Val Phe Ser Cys Ser Val
                690                 695                 700

Met His Glu Ala Leu His Asn His Tyr Thr Gln Lys Ser Leu Ser Leu
705                 710                 715                 720

Ser Pro Gly Lys

<210> SEQ ID NO 36
<211> LENGTH: 487
<212> TYPE: PRT

<213> ORGANISM: Artificial Sequence
<220> FEATURE:
<223> OTHER INFORMATION: Exemplary scTL1A-RBD module

<400> SEQUENCE: 36

```
Asp Gly Asp Lys Pro Arg Ala His Leu Thr Val Val Arg Gln Thr Pro
1               5                   10                  15

Thr Gln His Phe Lys Asn Gln Phe Pro Ala Leu His Trp Glu His Glu
            20                  25                  30

Leu Gly Leu Ala Phe Thr Lys Asn Arg Met Asn Tyr Thr Asn Lys Phe
        35                  40                  45

Leu Leu Ile Pro Glu Ser Gly Asp Tyr Phe Ile Tyr Ser Gln Val Thr
50                  55                  60

Phe Arg Gly Met Thr Ser Glu Cys Ser Glu Ile Arg Gln Ala Gly Arg
65                  70                  75                  80

Pro Asn Lys Pro Asp Ser Ile Thr Val Val Ile Thr Lys Val Thr Asp
                85                  90                  95

Ser Tyr Pro Glu Pro Thr Gln Leu Leu Met Gly Thr Lys Ser Val Cys
            100                 105                 110

Glu Val Gly Ser Asn Trp Phe Gln Pro Ile Tyr Leu Gly Ala Met Phe
        115                 120                 125

Ser Leu Gln Glu Gly Asp Lys Leu Met Val Asn Val Ser Asp Ile Ser
130                 135                 140

Leu Val Asp Tyr Thr Lys Glu Asp Lys Thr Phe Phe Gly Ala Phe Leu
145                 150                 155                 160

Leu Gly Ser Gly Ser Asn Gly Ser Pro Arg Ala His Leu Thr Val
                165                 170                 175

Val Arg Gln Thr Pro Thr Gln His Phe Lys Asn Gln Phe Pro Ala Leu
        180                 185                 190

His Trp Glu His Glu Leu Gly Leu Ala Phe Thr Lys Asn Arg Met Asn
    195                 200                 205

Tyr Thr Asn Lys Phe Leu Leu Ile Pro Glu Ser Gly Asp Tyr Phe Ile
    210                 215                 220

Tyr Ser Gln Val Thr Phe Arg Gly Met Thr Ser Glu Cys Ser Glu Ile
225                 230                 235                 240

Arg Gln Ala Gly Arg Pro Asn Lys Pro Asp Ser Ile Thr Val Val Ile
                245                 250                 255

Thr Lys Val Thr Asp Ser Tyr Pro Glu Pro Thr Gln Leu Leu Met Gly
            260                 265                 270

Thr Lys Ser Val Cys Glu Val Gly Ser Asn Trp Phe Gln Pro Ile Tyr
        275                 280                 285

Leu Gly Ala Met Phe Ser Leu Gln Glu Gly Asp Lys Leu Met Val Asn
    290                 295                 300

Val Ser Asp Ile Ser Leu Val Asp Tyr Thr Lys Glu Asp Lys Thr Phe
305                 310                 315                 320

Phe Gly Ala Phe Leu Leu Gly Ser Gly Ser Pro Arg Ala His Leu Thr
                325                 330                 335

Val Val Arg Gln Thr Pro Thr Gln His Phe Lys Asn Gln Phe Pro Ala
            340                 345                 350

Leu His Trp Glu His Glu Leu Gly Leu Ala Phe Thr Lys Asn Arg Met
        355                 360                 365

Asn Tyr Thr Asn Lys Phe Leu Leu Ile Pro Glu Ser Gly Asp Tyr Phe
    370                 375                 380

Ile Tyr Ser Gln Val Thr Phe Arg Gly Met Thr Ser Glu Cys Ser Glu
```

```
                385                 390                 395                 400
Ile Arg Gln Ala Gly Arg Pro Asn Lys Pro Asp Ser Ile Thr Val Val
                    405                 410                 415

Ile Thr Lys Val Thr Asp Ser Tyr Pro Glu Pro Thr Gln Leu Leu Met
                420                 425                 430

Gly Thr Lys Ser Val Cys Glu Val Gly Ser Asn Trp Phe Gln Pro Ile
            435                 440                 445

Tyr Leu Gly Ala Met Phe Ser Leu Gln Glu Gly Asp Lys Leu Met Val
        450                 455                 460

Asn Val Ser Asp Ile Ser Leu Val Asp Tyr Thr Lys Glu Asp Lys Thr
465                 470                 475                 480

Phe Phe Gly Ala Phe Leu Leu
                485

<210> SEQ ID NO 37
<211> LENGTH: 2279
<212> TYPE: DNA
<213> ORGANISM: Artificial Sequence
<220> FEATURE:
<223> OTHER INFORMATION: DNA encoding ORF of Seq25

<400> SEQUENCE: 37
aagctttagg gataacaggg taatagccgc caccatggag actgacaccc tgctggtgtt      60
cgtgctgctg gtctgggtgc ctgcaggaaa tggagacaag ccaagagcac acttgaccgt     120
ggtgcgacag acacctaccc agcattttaa gaatcaattc cctgctctcc actgggagca     180
cgagctgggt ctggccttta caagaacag aatgaactac actaacaaat ttctgctgat     240
ccctgaatct ggggattatt tcatctattc tcaggtgaca tttcggggaa tgacttcaga     300
gtgctcagaa attcgtcagg ctggaaggcc taataagccc gacagcatca cggtcgttat     360
taccaaagtg acagattctt atccagaacc aactcagctg ctgatgggta ccaagagcgt     420
ttgcgaagtg ggcagcaact ggttccagcc catctatctg ggtgctatgt tttctctgca     480
agagggcgat aaactcatgg tcaatgtgag tgacatttct cttgtggatt acactaagga     540
ggataagacc ttcttcggtg cattcctgct gggctcagga tctggcaatg ggagtcctag     600
agcccatctc acagtcgtga ggcagacccc aactcagcac ttcaagaacc agttccccgc     660
cctgcattgg gagcacgaac tgggtcttgc attcaccaag aacaggatga attacaccaa     720
taagttcctg ttgataccccg aatccggaga ctactttatc tactcccaag tcacctttcg     780
cggcatgact tctgaatgca gcgaaatccg gcaggctggt cgcccaaca agcccgattc     840 catcactgta gtgatcacca aggtaacaga cagctaccct gaacccacgc agctcctcat     900
gggcaccaaa agtgtgtgtg aagtcggcag caattggttt cagcccattt atctcggcgc     960
catgttttca cttcaggagg gtgataaact gatggtcaac gtttccgaca ttagcctcgt    1020
tgactacaca aaggaagata aactttctt cggggctttc ctgctggggt ccggaagtcc    1080
ccgagcccac ttgacagtcg ttcgtcaaac gccaacacag cactttaaga atcagtttcc    1140
agcccttcat tgggagcatg agttggggct ggcatttact aagaatcgca tgaactatac    1200
caacaaattc ctgctgatcc cagagagtgg ggattacttt atctacagcc aagtgacatt    1260
tcgaggcatg actagcgagt gttccgagat tcggcaggcc ggaaggccca acaagcctga    1320
ttccattacc gtggtcataa ctaaggtaac agactcctat ccagagccta cccagctttt    1380 gatgggggacc aaatccgttt gtgaggtggg ctcaaactgg tttcaaccca tatccttgg    1440 agccatgttc tccttgcagg agggagacaa actgatggtg aatgtgtctg acatcagtct    1500
```

-continued

```
ggtagactat accaaagagg acaaaacatt ctttggcgct ttcctcctgg gatcctcgag    1560
ttcatcgtcc tcatccggct catgtgataa gacccacacc tgccctccct gtcctgcccc    1620
tgagctgctg gcggaccttc ctgtgttcct gttccccccc aagcctaagg cacccctgat    1680
gatctccagg accctgagg tgacctgtgt ggtggtggac gtgtctcacg aagatcccga    1740
ggtgaagttc aactggtacg tggacggcgt ggaggtccac aacgccaaga ccaagcctag    1800
ggaggagcag tacagctcca cctacccggg ggtgtctgtg ctgaccgtgc tgcaccagga    1860
ttggctgaac ggaaaggagt ataagtgtaa ggtctccaac aaggccctgc ctgcccccat    1920
cgagaaaacc atctccaagg ccaagggcca gcctcgggag cctcaggtgt acaccctgcc    1980
tcctagcagg gaggagatga ccaagaacca ggtgtccctg acctgtctgg tgaagggctt    2040
ctacccttcc gatatcgccg tggagtggga gtctaatggc cagcccgaga caactacaa    2100 gaccaccct cctgtgctgg actctgacgg ctccttcttc ctgtactcca agctgaccgt    2160
ggacaagtcc agatggcagc agggcaacgt gttctcctgc tccgtgatgc acgaggccct    2220
gcacaatcac tacacccaga agtccctgtc tctgagtccg ggcaagtaat aggcgcgcc    2279
```

<210> SEQ ID NO 38
<211> LENGTH: 231
<212> TYPE: PRT
<213> ORGANISM: Artificial Sequence
<220> FEATURE:
<223> OTHER INFORMATION: Protein X: TL1A-RBD fused to RB69-FOLDON

<400> SEQUENCE: 38

```
Met Glu Thr Asp Thr Leu Leu Val Phe Val Leu Val Trp Val Asp
1               5                   10                  15

Lys Pro Arg Ala His Leu Thr Val Val Arg Gln Thr Pro Thr Gln His
            20                  25                  30

Phe Lys Asn Gln Phe Pro Ala Leu His Trp Glu His Glu Leu Gly Leu
        35                  40                  45

Ala Phe Thr Lys Asn Arg Met Asn Tyr Thr Asn Lys Phe Leu Leu Ile
    50                  55                  60

Pro Glu Ser Gly Asp Tyr Phe Ile Tyr Ser Gln Val Thr Phe Arg Gly
65                  70                  75                  80

Met Thr Ser Glu Cys Ser Glu Ile Arg Gln Ala Gly Arg Pro Asn Lys
                85                  90                  95

Pro Asp Ser Ile Thr Val Val Ile Thr Lys Val Thr Asp Ser Tyr Pro
            100                 105                 110

Glu Pro Thr Gln Leu Leu Met Gly Thr Lys Ser Val Cys Glu Val Gly
        115                 120                 125

Ser Asn Trp Phe Gln Pro Ile Tyr Leu Gly Ala Met Phe Ser Leu Gln
    130                 135                 140

Glu Gly Asp Lys Leu Met Val Asn Val Ser Asp Ile Ser Leu Val Asp
145                 150                 155                 160

Tyr Thr Lys Glu Asp Lys Thr Phe Phe Gly Ala Phe Leu Leu Gly Ser
                165                 170                 175

Gly Ser Ser Gly Ser Ser Gly Ser Ser Gly Ser Gly Tyr Ile Glu Asp
            180                 185                 190

Ala Pro Ser Asp Gly Lys Phe Tyr Val Arg Lys Asp Gly Ala Trp Val
        195                 200                 205

Glu Leu Pro Thr Ala Ser Gly Pro Ser Ser Ser Ser Ser Ala Trp
    210                 215                 220
```

Ser His Pro Gln Phe Glu Lys
225                 230

<210> SEQ ID NO 39
<211> LENGTH: 485
<212> TYPE: PRT
<213> ORGANISM: Artificial Sequence
<220> FEATURE:
<223> OTHER INFORMATION: Exemplary scTL1A-RBD module

<400> SEQUENCE: 39

Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
            20                  25                  30

Leu Ala Phe Thr Lys Asn Arg Met Asn Tyr Thr Asn Lys Phe Leu Leu
        35                  40                  45

Ile Pro Glu Ser Gly Asp Tyr Phe Ile Tyr Ser Gln Val Thr Phe Arg
50                  55                  60

Gly Met Thr Ser Glu Cys Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
        195                 200                 205

Asn Lys Phe Leu Leu Ile Pro Glu Ser Gly Asp Tyr Phe Ile Tyr Ser
210                 215                 220

Gln Val Thr Phe Arg Gly Met Thr Ser Glu Cys Ser Glu Ile Arg Gln
225                 230                 235                 240

Ala Gly Arg Pro Asn Lys Pro Asp Ser Ile Thr Val Val Ile Thr Lys
                245                 250                 255

Val Thr Asp Ser Tyr Pro Glu Pro Thr Gln Leu Leu Met Gly Thr Lys
            260                 265                 270

Ser Val Cys Glu Val Gly Ser Asn Trp Phe Gln Pro Ile Tyr Leu Gly
        275                 280                 285

Ala Met Phe Ser Leu Gln Glu Gly Asp Lys Leu Met Val Asn Val Ser
290                 295                 300

Asp Ile Ser Leu Val Asp Tyr Thr Lys Glu Asp Lys Thr Phe Phe Gly
305                 310                 315                 320

Ala Phe Leu Leu Gly Ser Gly Ser Pro Arg Ala His Leu Thr Val Val
                325                 330                 335

Arg Gln Thr Pro Thr Gln His Phe Lys Asn Gln Phe Pro Ala Leu His
            340                 345                 350

Trp Glu His Glu Leu Gly Leu Ala Phe Thr Lys Asn Arg Met Asn Tyr
                355                 360                 365

Thr Asn Lys Phe Leu Leu Ile Pro Glu Ser Gly Asp Tyr Phe Ile Tyr
    370                 375                 380

Ser Gln Val Thr Phe Arg Gly Met Thr Ser Glu Cys Ser Glu Ile Arg
385                 390                 395                 400

Gln Ala Gly Arg Pro Asn Lys Pro Asp Ser Ile Thr Val Val Ile Thr
                405                 410                 415

Lys Val Thr Asp Ser Tyr Pro Glu Pro Thr Gln Leu Leu Met Gly Thr
                420                 425                 430

Lys Ser Val Cys Glu Val Gly Ser Asn Trp Phe Gln Pro Ile Tyr Leu
                435                 440                 445

Gly Ala Met Phe Ser Leu Gln Glu Gly Asp Lys Leu Met Val Asn Val
                450                 455                 460

Ser Asp Ile Ser Leu Val Asp Tyr Thr Lys Glu Asp Lys Thr Phe Phe
465                 470                 475                 480

Gly Ala Phe Leu Leu
                485

<210> SEQ ID NO 40
<211> LENGTH: 491
<212> TYPE: PRT
<213> ORGANISM: Artificial Sequence
<220> FEATURE:
<223> OTHER INFORMATION: Exemplary scTL1A-RBD module

<400> SEQUENCE: 40

Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
                20                  25                  30

Leu Ala Phe Thr Lys Asn Arg Met Asn Tyr Thr Asn Lys Phe Leu Leu
                35                  40                  45

Ile Pro Glu Ser Gly Asp Tyr Phe Ile Tyr Ser Gln Val Thr Phe Arg
            50                  55                  60

Gly Met Thr Ser Glu Cys Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Cys Glu Val
            100                 105                 110

Gly Ser Asn Trp Phe Gln Pro Ile Tyr Leu Gly Ala Met Phe Ser Leu
                115                 120                 125

Gln Glu Gly Asp Lys Leu Met Val Asn Val Ser Asp Ile Ser Leu Val
            130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Lys Pro Arg Ala His Leu Thr Val Val
                165                 170                 175

Arg Gln Thr Pro Thr Gln His Phe Lys Asn Gln Phe Pro Ala Leu His
            180                 185                 190

Trp Glu His Glu Leu Gly Leu Ala Phe Thr Lys Asn Arg Met Asn Tyr
                195                 200                 205

Thr Asn Lys Phe Leu Leu Ile Pro Glu Ser Gly Asp Tyr Phe Ile Tyr
    210                 215                 220

Ser Gln Val Thr Phe Arg Gly Met Thr Ser Glu Cys Ser Glu Ile Arg
225                 230                 235                 240

Gln Ala Gly Arg Pro Asn Lys Pro Asp Ser Ile Thr Val Val Ile Thr
            245                 250                 255

Lys Val Thr Asp Ser Tyr Pro Glu Pro Thr Gln Leu Leu Met Gly Thr
        260                 265                 270

Lys Ser Val Cys Glu Val Gly Ser Asn Trp Phe Gln Pro Ile Tyr Leu
    275                 280                 285

Gly Ala Met Phe Ser Leu Gln Glu Gly Asp Lys Leu Met Val Asn Val
290                 295                 300

Ser Asp Ile Ser Leu Val Asp Tyr Thr Lys Glu Asp Lys Thr Phe Phe
305                 310                 315                 320

Gly Ala Phe Leu Leu Gly Ser Gly Ser Gly Asn Gly Ser Lys Pro Arg
                325                 330                 335

Ala His Leu Thr Val Val Arg Gln Thr Pro Thr Gln His Phe Lys Asn
            340                 345                 350

Gln Phe Pro Ala Leu His Trp Glu His Glu Leu Gly Leu Ala Phe Thr
        355                 360                 365

Lys Asn Arg Met Asn Tyr Thr Asn Lys Phe Leu Leu Ile Pro Glu Ser
370                 375                 380

Gly Asp Tyr Phe Ile Tyr Ser Gln Val Thr Phe Arg Gly Met Thr Ser
385                 390                 395                 400

Glu Cys Ser Glu Ile Arg Gln Ala Gly Arg Pro Asn Lys Pro Asp Ser
                405                 410                 415

Ile Thr Val Val Ile Thr Lys Val Thr Asp Ser Tyr Pro Glu Pro Thr
            420                 425                 430

Gln Leu Leu Met Gly Thr Lys Ser Val Cys Glu Val Gly Ser Asn Trp
        435                 440                 445

Phe Gln Pro Ile Tyr Leu Gly Ala Met Phe Ser Leu Gln Glu Gly Asp
    450                 455                 460

Lys Leu Met Val Asn Val Ser Asp Ile Ser Leu Val Asp Tyr Thr Lys
465                 470                 475                 480

Glu Asp Lys Thr Phe Phe Gly Ala Phe Leu Leu
                485                 490

<210> SEQ ID NO 41
<211> LENGTH: 499
<212> TYPE: PRT
<213> ORGANISM: Artificial Sequence
<220> FEATURE:
<223> OTHER INFORMATION: Exemplary scTL1A-RBD module

<400> SEQUENCE: 41

Asp Gly Asp Lys Pro Arg Ala His Leu Thr Val Val Arg Gln Thr Pro
1               5                   10                  15

Thr Gln His Phe Lys Asn Gln Phe Pro Ala Leu His Trp Glu His Glu
            20                  25                  30

Leu Gly Leu Ala Phe Thr Lys Asn Arg Met Asn Tyr Thr Asn Lys Phe
        35                  40                  45

Leu Leu Ile Pro Glu Ser Gly Asp Tyr Phe Ile Tyr Ser Gln Val Thr
    50                  55                  60

Phe Arg Gly Met Thr Ser Glu Cys Ser Glu Ile Arg Gln Ala Gly Arg
65                  70                  75                  80

Pro Asn Lys Pro Asp Ser Ile Thr Val Val Ile Thr Lys Val Thr Asp
                85                  90                  95

```
Ser Tyr Pro Glu Pro Thr Gln Leu Leu Met Gly Thr Lys Ser Val Cys
            100                 105                 110

Glu Val Gly Ser Asn Trp Phe Gln Pro Ile Tyr Leu Gly Ala Met Phe
        115                 120                 125

Ser Leu Gln Glu Gly Asp Lys Leu Met Val Asn Val Ser Asp Ile Ser
    130                 135                 140

Leu Val Asp Tyr Thr Lys Glu Asp Lys Thr Phe Phe Gly Ala Phe Leu
145                 150                 155                 160

Leu Gly Ser Gly Ser Gly Asn Gly Ser Asp Gly Asp Lys Pro Arg Ala
                165                 170                 175

His Leu Thr Val Val Arg Gln Thr Pro Thr Gln His Phe Lys Asn Gln
            180                 185                 190

Phe Pro Ala Leu His Trp Glu His Glu Leu Gly Leu Ala Phe Thr Lys
        195                 200                 205

Asn Arg Met Asn Tyr Thr Asn Lys Phe Leu Leu Ile Pro Glu Ser Gly
    210                 215                 220

Asp Tyr Phe Ile Tyr Ser Gln Val Thr Phe Arg Gly Met Thr Ser Glu
225                 230                 235                 240

Cys Ser Glu Ile Arg Gln Ala Gly Arg Pro Asn Lys Pro Asp Ser Ile
                245                 250                 255

Thr Val Val Ile Thr Lys Val Thr Asp Ser Tyr Pro Glu Pro Thr Gln
            260                 265                 270

Leu Leu Met Gly Thr Lys Ser Val Cys Glu Val Gly Ser Asn Trp Phe
        275                 280                 285

Gln Pro Ile Tyr Leu Gly Ala Met Phe Ser Leu Gln Glu Gly Asp Lys
    290                 295                 300

Leu Met Val Asn Val Ser Asp Ile Ser Leu Val Asp Tyr Thr Lys Glu
305                 310                 315                 320

Asp Lys Thr Phe Phe Gly Ala Phe Leu Leu Gly Ser Gly Ser Gly Asn
                325                 330                 335

Gly Ser Asp Gly Asp Lys Pro Arg Ala His Leu Thr Val Val Arg Gln
            340                 345                 350

Thr Pro Thr Gln His Phe Lys Asn Gln Phe Pro Ala Leu His Trp Glu
        355                 360                 365

His Glu Leu Gly Leu Ala Phe Thr Lys Asn Arg Met Asn Tyr Thr Asn
    370                 375                 380

Lys Phe Leu Leu Ile Pro Glu Ser Gly Asp Tyr Phe Ile Tyr Ser Gln
385                 390                 395                 400

Val Thr Phe Arg Gly Met Thr Ser Glu Cys Ser Glu Ile Arg Gln Ala
                405                 410                 415

Gly Arg Pro Asn Lys Pro Asp Ser Ile Thr Val Val Ile Thr Lys Val
            420                 425                 430

Thr Asp Ser Tyr Pro Glu Pro Thr Gln Leu Leu Met Gly Thr Lys Ser
        435                 440                 445

Val Cys Glu Val Gly Ser Asn Trp Phe Gln Pro Ile Tyr Leu Gly Ala
    450                 455                 460

Met Phe Ser Leu Gln Glu Gly Asp Lys Leu Met Val Asn Val Ser Asp
465                 470                 475                 480

Ile Ser Leu Val Asp Tyr Thr Lys Glu Asp Lys Thr Phe Phe Gly Ala
                485                 490                 495

Phe Leu Leu

<210> SEQ ID NO 42
```

```
<211> LENGTH: 499
<212> TYPE: PRT
<213> ORGANISM: Artificial Sequence
<220> FEATURE:
<223> OTHER INFORMATION: Exemplary scTL1A-RBD module

<400> SEQUENCE: 42

Asp Gly Asp Lys Pro Arg Ala His Leu Thr Val Val Arg Gln Thr Pro
1               5                   10                  15

Thr Gln His Phe Lys Asn Gln Phe Pro Ala Leu His Trp Glu His Glu
            20                  25                  30

Leu Gly Leu Ala Phe Thr Lys Asn Arg Met Asn Tyr Th

```
Lys Phe Leu Leu Ile Pro Glu Ser Gly Asp Tyr Phe Ile Tyr Ser Gln
385                 390                 395                 400

Val Thr Phe Arg Gly Met Thr Ser Glu Ser Ser Glu Ile Arg Gln Ala
            405                 410                 415

Gly Arg Pro Asn Lys Pro Asp Ser Ile Thr Val Val Ile Thr Lys Val
            420                 425                 430

Thr Asp Ser Tyr Pro Glu Pro Thr Gln Leu Leu Met Gly Thr Lys Ser
            435                 440                 445

Val Ser Glu Val Gly Ser Asn Trp Phe Gln Pro Ile Tyr Leu Gly Ala
        450                 455                 460

Met Phe Ser Leu Gln Glu Gly Asp Lys Leu Met Val Asn Val Ser Asp
465                 470                 475                 480

Ile Ser Leu Val Asp Tyr Thr Lys Glu Asp Lys Thr Phe Phe Gly Ala
                485                 490                 495

Phe Leu Leu
```

<210> SEQ ID NO 43
<211> LENGTH: 485
<212> TYPE: PRT
<213> ORGANISM: Artificial Sequence
<220> FEATURE:
<223> OTHER INFORMATION: Exemplary scTL1A-RBD module

<400> SEQUENCE: 43

```
Asp Lys Pro Arg Ala His Leu Thr Val Val Arg Gln Thr Pro Thr Gln
1               5                   10                  15

His Phe Lys Asn Gln Phe Pro Ala Leu His Trp Glu His Glu Leu Gly
            20                  25                  30

Leu Ala Phe Thr Lys Asn Arg Met Asn Tyr Thr Asn Lys Phe Leu Leu
        35                  40                  45

Ile Pro Glu Ser Gly Asp Tyr Phe Ile Tyr Ser Gln Val Thr Phe Arg
50                  55                  60

Gly Met Thr Ser Glu Ser Ser Glu Ile Arg Gln Ala Gly Arg Pro Asn
65                  70                  75                  80

Lys Pro Asp Ser Ile Thr Val Val Ile Thr Lys Val Thr Asp Ser Tyr
                85                  90                  95

Pro Glu Pro Thr Gln Leu Leu Met Gly Thr Lys Ser Val Ser Glu Val
            100                 105                 110

Gly Ser Asn Trp Phe Gln Pro Ile Tyr Leu Gly Ala Met Phe Ser Leu
        115                 120                 125

Gln Glu Gly Asp Lys Leu Met Val Asn Val Ser Asp Ile Ser Leu Val
    130                 135                 140

Asp Tyr Thr Lys Glu Asp Lys Thr Phe Phe Gly Ala Phe Leu Leu Gly
145                 150                 155                 160

Ser Gly Ser Gly Asn Gly Ser Pro Arg Ala His Leu Thr Val Val Arg
                165                 170                 175

Gln Thr Pro Thr Gln His Phe Lys Asn Gln Phe Pro Ala Leu His Trp
            180                 185                 190

Glu His Glu Leu Gly Leu Ala Phe Thr Lys Asn Arg Met Asn Tyr Thr
        195                 200                 205

Asn Lys Phe Leu Leu Ile Pro Glu Ser Gly Asp Tyr Phe Ile Tyr Ser
    210                 215                 220

Gln Val Thr Phe Arg Gly Met Thr Ser Glu Ser Ser Glu Ile Arg Gln
225                 230                 235                 240
```

```
Ala Gly Arg Pro Asn Lys Pro Asp Ser Ile Thr Val Val Ile Thr Lys
            245                 250                 255
Val Thr Asp Ser Tyr Pro Glu Pro Thr Gln Leu Leu Met Gly Thr Lys
            260                 265                 270
Ser Val Ser Glu Val Gly Ser Asn Trp Phe Gln Pro Ile Tyr Leu Gly
            275                 280                 285
Ala Met Phe Ser Leu Gln Glu Gly Asp Lys Leu Met Val Asn Val Ser
            290                 295                 300
Asp Ile Ser Leu Val Asp Tyr Thr Lys Glu Asp Lys Thr Phe Phe Gly
305                 310                 315                 320
Ala Phe Leu Leu Gly Ser Gly Ser Pro Arg Ala His Leu Thr Val Val
                    325                 330                 335
Arg Gln Thr Pro Thr Gln His Phe Lys Asn Gln Phe Pro Ala Leu His
                340                 345                 350
Trp Glu His Glu Leu Gly Leu Ala Phe Thr Lys Asn Arg Met Asn Tyr
            355                 360                 365
Thr Asn Lys Phe Leu Leu Ile Pro Glu Ser Gly Asp Tyr Phe Ile Tyr
            370                 375                 380
Ser Gln Val Thr Phe Arg Gly Met Thr Ser Glu Ser Ser Glu Ile Arg
385                 390                 395                 400
Gln Ala Gly Arg Pro Asn Lys Pro Asp Ser Ile Thr Val Val Ile Thr
                    405                 410                 415
Lys Val Thr Asp Ser Tyr Pro Glu Pro Thr Gln Leu Leu Met Gly Thr
                420                 425                 430
Lys Ser Val Ser Glu Val Gly Ser Asn Trp Phe Gln Pro Ile Tyr Leu
            435                 440                 445
Gly Ala Met Phe Ser Leu Gln Glu Gly Asp Lys Leu Met Val Asn Val
    450                 455                 460
Ser Asp Ile Ser Leu Val Asp Tyr Thr Lys Glu Asp Lys Thr Phe Phe
465                 470                 475                 480
Gly Ala Phe Leu Leu
                485
```

US 10,683,338 B2

SINGLE-CHAIN TL1A RECEPTOR AGONIST PROTEINS

This application is a continuation of PCT/EP2016/075574, filed Oct. 24, 2016; which claims priority to U.S. Provisional Application No. 62/247,671, filed Oct. 28, 2015. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Apr. 11, 2018, and a size of 111 kilobytes. The Sequence Listing filed via EFS-Web is part of the specification and is hereby incorporated in its entirety by reference herein.

FIELD OF THE INVENTION

The present invention provides specific TL1A receptor agonist proteins comprising three soluble TL1A domains and an Fc fragment, nucleic acid molecules encoding the TL1A receptor agonist proteins, and uses thereof. The TL1A receptor agonist proteins are substantially non-aggregating and suitable for therapeutic, diagnostic and/or research applications.

BACKGROUND OF THE INVENTION

It is known that trimerization of TNF superfamily (TNFSF) cytokines is required for efficient receptor binding and activation. Trimeric complexes of TNF superfamily cytokines, however, are difficult to prepare from recombinant monomeric units.

WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1989), 1205-1213) describe that trimers of TNF cytokines are stabilized by N-terminally positioned stabilization motifs. In CD95L, the stabilization of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these single-chain fusion polypeptides show undesired aggregation.

WO 2010/010051 discloses single-chain fusion polypeptides comprising three soluble TNF family cytokine domains and at least two peptide linkers. The described fusion polypeptides are substantially non-aggregating.

There is a need in the art for novel TL1A receptor agonists that exhibit high biological activity independent of Fc-gamma-R based crosslinking in vivo, high stability, and allow for efficient recombinant manufacturing. Additionally, there is need in the art for enabling technologies to create human TL1A-receptor selective biologics as human TL1A has at least two interaction partners in vivo: DcR3 (Decoy receptor 3) and DR3 (Death receptor 3).

SUMMARY OF THE INVENTION

The present invention provides specific TL1A receptor agonist proteins that mimic the TL1A-receptor(s): TL1A interaction in vivo, exhibit low proteolytic degradation and a shorter in vivo half-life as compared to agonistic monoclonal antibodies.

The TL1A receptor agonist proteins of the instant invention generally comprise: (i) a first soluble TL1A cytokine domain; (ii) a first peptide linker; (iii) a second soluble TL1A domain; (iv) a second peptide linker, (v) a third soluble TL1A domain; (vi) a third peptide linker (e.g., a hinge-linker) and (vii) an antibody Fc fragment.

In one embodiment, the antibody Fc fragment (vii) is located N terminal to the first TL1A domain (i) and/or C-terminal to the third TL1A domain (v). In another embodiment the antibody Fc fragment is located C-terminally to the third TL1A domain (v). In one embodiment, the polypeptide is substantially non-aggregating. In another embodiment, the second and/or third soluble TL1A domain is an N-terminally shortened domain which optionally comprises amino acid sequence mutations.

In one embodiment, at least one of the soluble TL1A domains, particularly at least one of the soluble TL1A domains (iii) and (v), is a soluble TL1A domain with an N-terminal sequence which starts at amino acid Asp91 or Gly92 or Asp93 or Lys94 or Pro95 of human TL1A and wherein Asp91 or Asp93 or Lys94 may be replaced by a neutral amino acid, e.g., Ser or Gly. In another embodiment, at least one of the soluble TL1A domains, particularly at least one of the soluble TL1A domains (iii) and (v), is a soluble TL1A domain with an N-terminal sequences selected from (a) Lys94-Pro95 and (b) (Gly/Ser)94-Pro95. In one embodiment, the soluble TL1A domain ends with amino acid Leu251 of human TL1A and/or optionally comprises one or more mutation at positions: R96, R103, F114, L123, G124, M158, D175, S187, Y188, N207, F209, T239, E241, N133, L251.

In one embodiment, the soluble TL1A domains (i), (iii) and (v) comprise amino acids Asp91-Leu251 of human TL1A according to SEQ ID NO: 01.

In another embodiment, at least one of the soluble TL1A domains, particularly at least the soluble TL1A domains (i), is a soluble TL1A domain with an N-terminal sequence which starts at amino acid Asp91 and wherein Asp91 may be replaced by Gln.

In one embodiment, the first and second peptide linkers (ii) and (iv) independently have a length of 3-8 amino acids, particularly a length of 3, 4, 5, 6, 7, or 8 amino acids, and preferably are glycine/serine linkers, optionally comprising an asparagine residue which may be glycosylated. In one embodiment, the first and the second peptide linkers (ii) and (iv) consist of the amino acid sequence according to SEQ ID NO: 2. In another embodiment, the polypeptide additionally comprises an N-terminal signal peptide domain, e.g., of SEQ ID NO: 17, which may comprise a protease cleavage site, and/or which additionally comprises a C-terminal element which may comprise and/or connect to a recognition/purification domain, e.g., a Strep-tag attached to a serine linker according to SEQ ID NO: 18.

In one embodiment, the antibody Fc fragment (vii) is fused to the soluble TL1A domain (i) and/or (v) via a hinge-linker, preferably of SEQ ID NO: 16. In another embodiment, the antibody Fc fragment (vii) consists of the amino acid sequence as shown in SEQ ID NO: 13 or 14.

In one embodiment, the single-chain fusion polypeptide of the present invention comprises the amino acid sequence selected from the group consisting of SEQ ID NO: 15, and 25-35.

In one embodiment, the present invention provides a TL1A receptor agonist protein comprising a dimer of two single-chain fusion polypeptides each having the amino acid sequence set forth in SEQ ID NO: 27. In one embodiment, the two polypeptides are covalently linked through three interchain disulfide bonds formed between cysteine residues 497, 503, and 506 of each polypeptide. Similar cysteine residues are positions 497, 503 and 506 of SEQ ID NO: 28 or 29, 30.

In SEQ ID 31, the two polypeptides of the dimer are covalently linked through three interchain disulfide bonds formed between cysteine residues 503, 509, and 512 of each polypeptide. In SEQ ID 32, the two polypeptides of the dimer are covalently linked through three interchain disulfide bonds formed between cysteine residues 494, 500, and 503 of each polypeptide.

In one embodiment, one the asparagine residue at position 165 of the mature polypeptide(s) SEQ ID NO: 27, 28, 29, 30, 31 and 32 are N-glycosylated.

In another embodiment, one or more of the asparagine residues at positions 165 and 331 of the mature polypeptide SEQ ID NO: 31 are N-glycosylated.

In another embodiment, the polypeptide(s) are further post-translationally modified. In another embodiment, the post-translational modification comprises the N-terminal glutamine of the mature polypeptide(s) SEQ ID NO: 30 and 32 modified to pyroglutamate.

(1) scTL1A-RBD; (2) CH2 domain; (3) CH3 domain; (4) Hinge-Cysteines (left side: oxidized to disulfidbridges; right side reduced stage with free thiols); (5) CH2-Carbohydrates attached to N297 position (EU-numbering); (6) Upper Hinge Lysine (K223)

Figure 6:
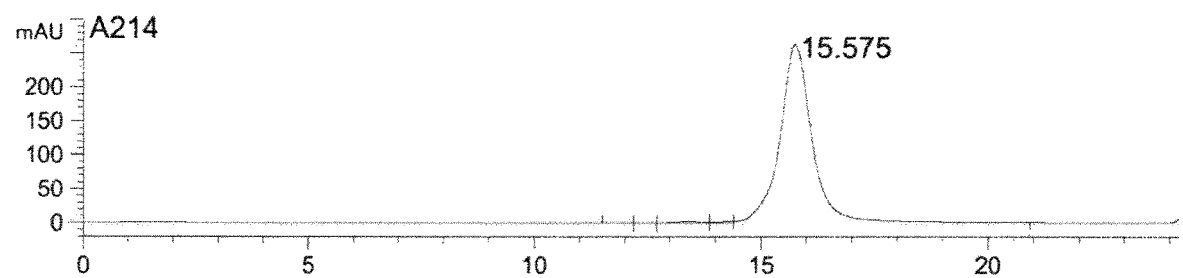

FIG. 6 Analytical size exclusion chromatography of strep tagged PROTEIN A (SEQ ID NO: 28) performed on a 1260 Infinity HPLC system using a Tosoh TSKgelG3000SWxl column. The column was loaded with protein at a concentration of 0.8 mg/ml in a total volume of 20 µl. The flow rate was set to 0.5 ml/min. One observes a single main peak at 15.575 min for PROTEIN A

DETAILED DESCRIPTION OF THE INVENTION

The present invention provides a single-chain fusion polypeptide comprising at least three soluble TL1A domains connected by two peptide linkers and N-terminally and/or C-terminally an antibody-derived dimerization domain. The inventors have discovered that dimerization of the two single-chain fusion polypeptides through the dimerization domain results in a hexavalent TL1A receptor agonist, which provides high biological activity and good stability.

Preferably, the single-chain fusion polypeptide is non-aggregating. The term "non-aggregating" refers to a monomer content of the preparation of ≥50%, preferably ≥70% and more preferably ≥90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the "monomer" content is as defined above after a time period of several days, e.g. 10 days, more preferably after several weeks, e.g. 2, 3 or 4 weeks, and most preferably after several months, e.g. 2 or 3 months of storage at 4° C., or 25° C. With regard to the definition of "monomer" in the case of FC-fusion proteins, the assembly of two polypeptide chains is driven by the FC-part and the functional unit of the resulting assembled protein consists of two chains. This unit is defined as "monomer" in the case of Fc-fusion proteins regardless of being a dimerized single-chain fusion polypeptide.

The single-chain fusion polypeptide may comprise additional domains which may be located at the N- and/or C-termini thereof. Examples for additional fusion domains are e.g. an N-terminal signal peptide domain which may comprise a protease cleave site or a C-terminal element which may comprise and/or connect to a recognition/purification domain. According to a preferred embodiment, the fusion polypeptide comprises a Strep-tag at its C-terminus that is fused via a linker. An exemplary Strep-tag including a short serine linker is shown in SEQ ID NO: 18.

The TL1A receptor agonist protein of the present invention comprises three soluble domains derived from TL1A. Preferably, those soluble domains are derived from a mammalian, particularly human TL1A including allelic variants and/or derivatives thereof. The soluble domains comprise the extracellular portion of TL1A including the receptor binding domain without membrane located domains. Like other proteins of the TNF superfamily, TL1A is anchored to the membrane via an N-terminal portion of 15-30 amino acids, the so-called stalk-region. The stalk region contributes to trimerization and provides a certain distance to the cell membrane. However, the stalk region is not part of the receptor binding domain (RBD).

Figure 1:
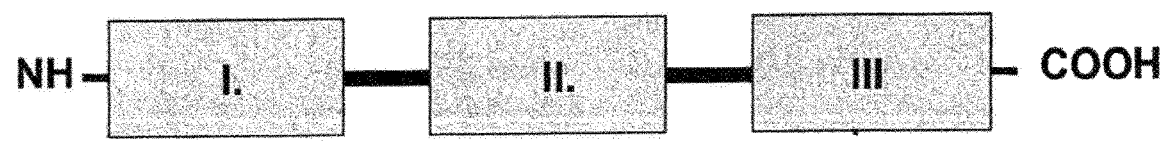
FIG. 1 Domain structure of a single-chain fusion polypeptide comprising three TL1A domains. I., II., III. Soluble TL1A domains.
Figure 1:
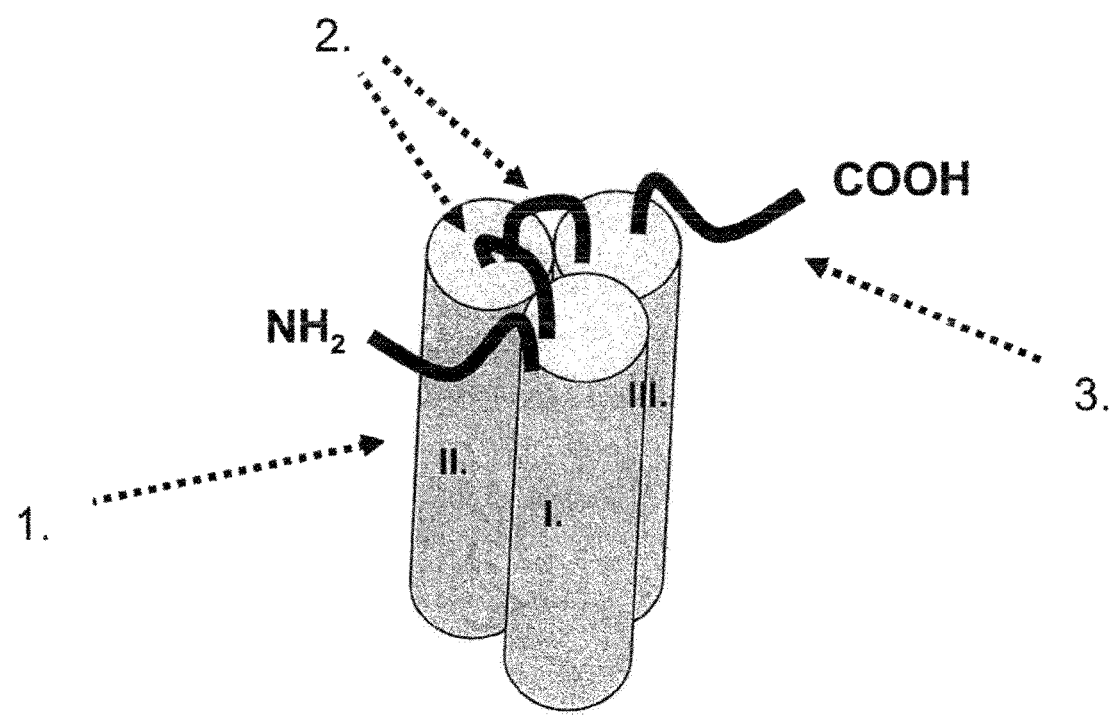
Figure 2:
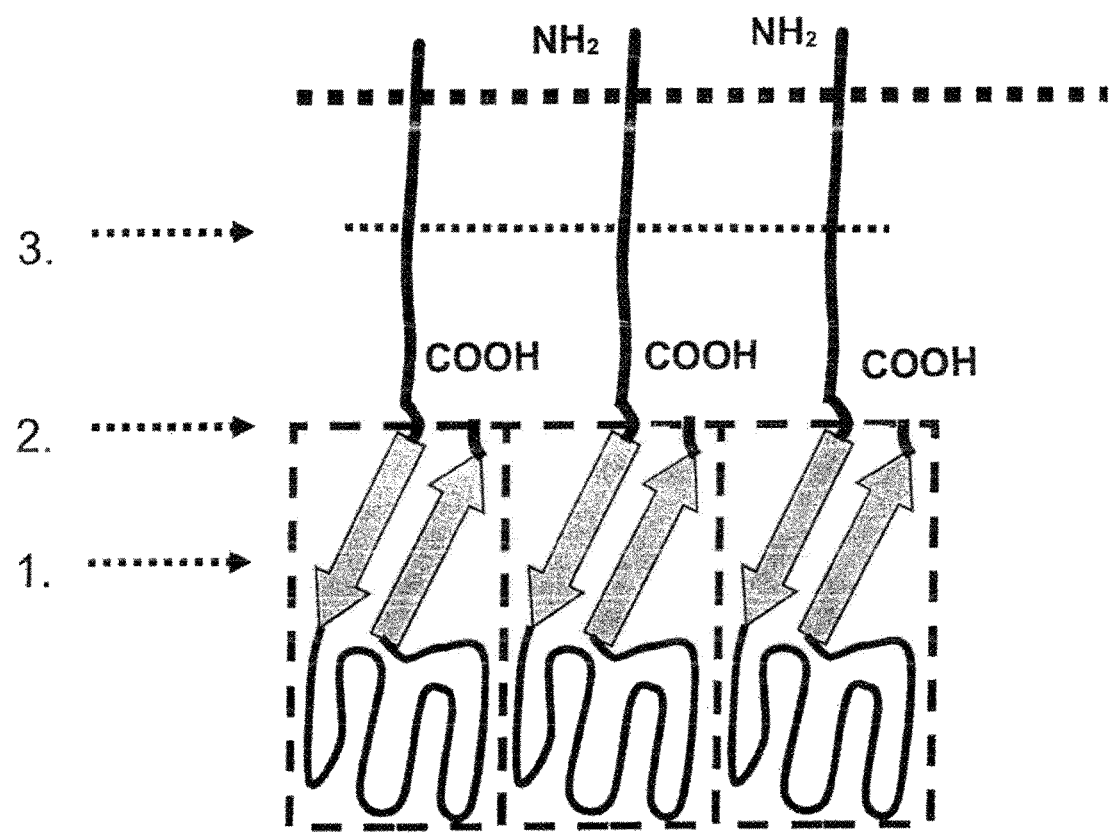
FIG. 2 Schematic picture representing the general structure of TL1A.
Cell membrane, N-terminus located within the cell,
1. anti-parallel β-fold of receptor-binding domain (RBD),
2. interface of RBD and cell membrane,
3. protease cleavage site.
Figure 3:
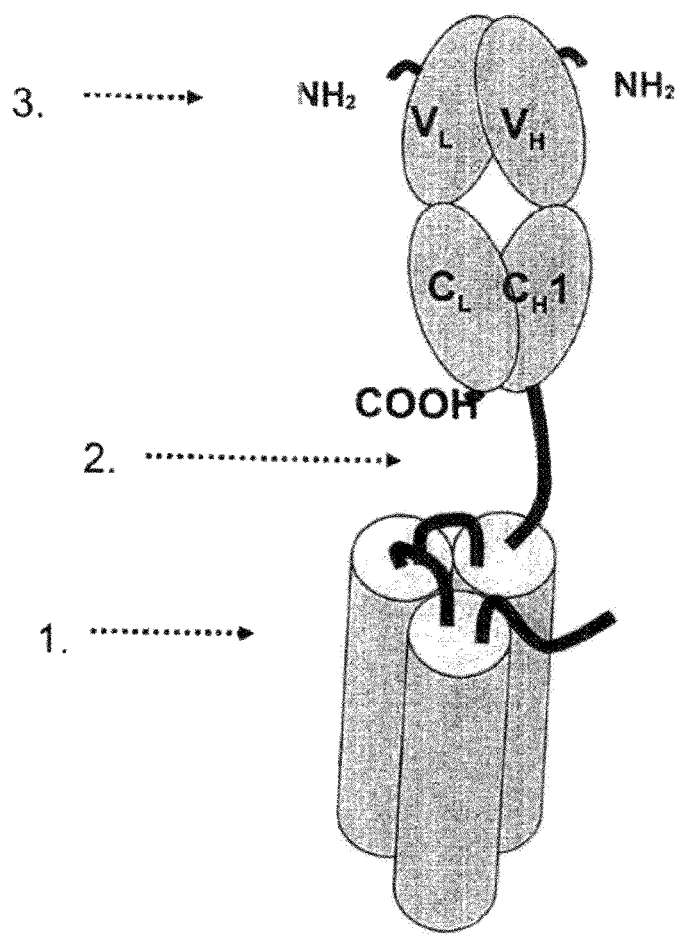
FIG. 3 Single-chain fusion polypeptide comprising an additional Fab antibody fragment.
Figure 4:
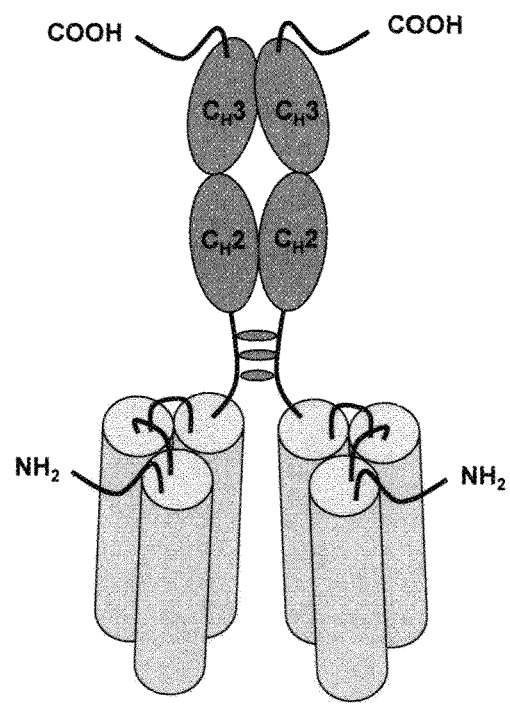
FIG. 4 Dimerization of two C-terminally fused scFc fusion polypeptides via three disulfide bridges.
Figure 5:
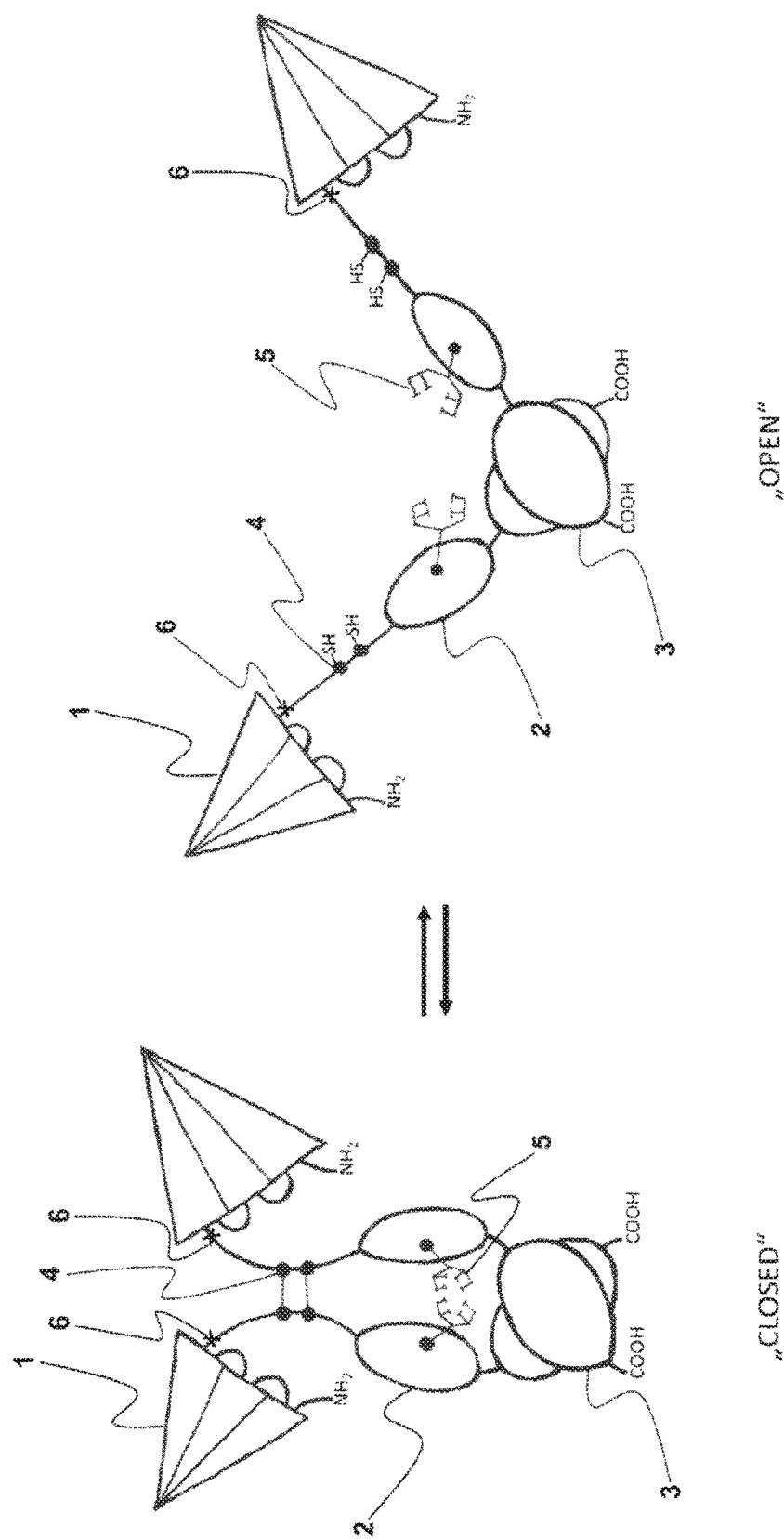
FIG. 5 Schematic representation of the hexavalent single chain TL1A receptor agonist fusion protein of the invention. CH2-Carbohydrates (5) present on the inner surface areas normally shield the CH2-subdomain sterically (2) from proteases during "open Fc-conformation transits" wherein hinge-interchain disulfide bonds (4) are reduced and the covalent interchain linkage is disrupted. This enables CH2-dissociation and exposure of the inner surface areas and the upper hinge lysine K223 (6) towards proteases. Dimer association in the "open stage" remains intact due to the high affinity of the CH3 domains (3) to each other.

Importantly, the RBD is characterized by a particular localization of its N- and C-terminal amino acids. Said amino acids are immediately adjacent and are located centrally to the axis of the trimer. The first N-terminal amino acids of the RBD form an anti-parallel beta-strand with the C-terminal amino acids of the RBD (FIG. 2).

Thus, the anti-parallel beta-strand of the RBD forms an interface with the cell membrane, which is connected to and anchored within the cell membrane via the amino acids of the stalk region. It is highly preferred that the soluble TL1A domains of the TL1A receptor agonist protein comprise a receptor binding domain of the TL1A lacking any amino acids from the stalk region. Otherwise, a long linker connecting the C-terminus of one of the soluble domains with the N-terminus of the next soluble domain would be required to compensate for the N-terminal stalk-region of the next soluble domain, which might result in instability and/or formation of aggregates.

A further advantage of such soluble domains is that the N-terminal amino acids of the RBD are not accessible for any anti-drug antibodies. Preferably, the single-chain fusion polypeptide consisting of (i) a first soluble TL1A cytokine domain; (ii) a first peptide linker; (iii) a second soluble TL1A domain; (iv) a second peptide linker; (v) a third soluble TL1A domain is capable of forming an ordered structure mimicking the trimeric organization of its natural counterpart thereby comprising at least one functional binding site for the respective TL1A receptor. The single-chain fusion polypeptide comprising components (i)-(v) is therefore also termed single-chain-TL1A-receptor-binding-domain (scTL1A-RBD).

The TL1A receptor agonist protein comprises three functional TL1A-receptor binding sites, i.e. amino acid sequences capable of forming a complex with a TL1A-receptor. Thus, the soluble domains are capable of binding to the corresponding TL1A-receptor. In one embodiment, at least one of the soluble domains is capable of receptor activation, whereby apoptotic and/or proliferative activity may be affected. In a further embodiment, one or more of the soluble domains are selected as not being capable of receptor activation.

The soluble TL1A domain may be derived from human TL1A as shown in SEQ ID NO: 1. Preferably, the soluble TL1A domains are derived from human TL1A, particularly starting from amino acids 91 or 95 and comprise particularly amino acids 91-251 or 95-251 of SEQ ID NO: 1. Optionally, amino acid Asp91 of SEQ ID NO: 1 may be replaced by a non-charged amino acid, e.g. Ser or Gly or is replaced by Glutamine.

TABLE 1

Sequence of Wild-Type Human TL1A Protein

| SEQ ID NO | Sequence |
|---|---|
| 1 | MAEDLGLSFGETASVEMLPEHGSCRPKARSSSARWALTCCLVLLPF YLAGLTTLLVSQLRAQGEACVQFQALKGQEFAPSHQQVYAPLRADG DKPRAHLTVVRQTPTQHFKNQFPALHWEHELGLAFTKNRMNYTNKF LLIPESGDYFIYSQVTFRGMTSECSEIRQAGRPNKPDSITVVITKV TDSYPEPTQLLMGTKSVCEVGSNWFQPIYLGAMFSLQEGDKLMVNV SDISLVDYTKEDKTFFGAFLL |

As indicated above, the soluble TL1A domains may comprise the wild-type sequences as indicated in SEQ ID NO: 1. It should be noted, however, that it is possible to introduce mutations in one or more of these soluble domains, e.g. mutations which alter (e.g. increase or decrease) the binding properties of the soluble domains. In one embodiment, soluble domains that cannot bind to the corresponding cytokine receptor can be selected.

In a further embodiment of the invention, the soluble TL1A domain (i) comprises a mutant of TL1A or a receptor binding domain thereof resulting in reduced affinity and/or reduced activation of TL1A-receptor.

TL1A-Muteins Affecting Receptor Binding and/or Activity

The mutant may be generated by any technique known by a skilled person. The substitution may affect at least one amino acid of TL1A, e.g., human TL1A (e.g., SEQ ID NO: 1) or a receptor binding domain thereof as described herein. Preferred substitutions in this regard affect at least one of the following amino acids of human TL1A of SEQ ID NO: 1: R103, L123, G124, M158, D175, S187, Y188, N207, F209, T239, E241.

In a preferred embodiment Y188 is mutated to S, T, D, E, R or F.

Human TL1A has at least two different receptors/interaction partners in vivo, namely DcR3 (Decoy Receptor 3) and DR3 (Death Receptor 3). The amino acid substitution(s) may affect the binding and/or activity of TL1A, e.g., human TL1A, to or on either the TL1A-receptor(s) binding or the TL1A-receptor(s) induced signaling. The binding and/or activity of the TL1A-receptor may be affected positively, i.e., stronger, more selective or more specific binding and/or more activation of the receptor. Alternatively, the binding and/or activity of the TL1A-receptor may be affected negatively, i.e., weaker, less selective or less specific binding and/or less or no activation of the receptor or receptor(s).

Thus one embodiment is a TL1A receptor agonist protein as described herein wherein at least one of the soluble domains comprises a mutant of TL1A or a receptor binding domain thereof which binds and/or activates TL1A-receptor(s) to a lesser extent than the wildtype-TL1A.

The single-chain fusion molecule of the present invention comprises three soluble TL1A domains, namely components (i), (iii) and (v). The stability of a single-chain TL1A fusion polypeptide against aggregation is enhanced, if the second and/or third soluble TL1A domain is an N-terminally shortened domain which optionally comprises amino acid sequence mutations. Thus, preferably, both the second and the third soluble TL1A domain are N-terminally shortened domains which optionally comprise amino acid sequence mutations in the N-terminal regions, preferably within the first five amino acids of the N-terminus of the soluble TL1A domain. These mutations may comprise replacement of basic amino acids, by neutral amino acids, particularly serine or glycine.

In contrast thereto, the selection of the first soluble TL1A domain is not as critical. Here, a soluble domain having a full-length N-terminal sequence may be used. It should be noted, however, that also the first soluble TL1A domain may have an N-terminally shortened and optionally mutated sequence.

In a further preferred embodiment of the present invention, the soluble TL1A domains (i), (iii) and (v) are soluble human TL1A domains. The first soluble TL1A domain (i) may be selected from native, shortened and/or mutated sequences. Thus, the first soluble TL1A domain (i) has an N-terminal sequence which may start at amino acid Asp91 or Pro95 of human TL1A, and wherein Asp91 may be replaced by a neutral amino acid, e.g. by Ser or Gly or by Gln to enable pyroglutamate formation during expression. The second and third soluble TL1A domains (iii) and (v) have a shortened N-terminal sequence which preferably starts with amino acid Asp93 or Pro95 of human TL1A (SEQ ID NO:1) and wherein Asp93 may be replaced by another amino acid, e.g. Ser or Gly.

Preferably, the N-terminal sequence of the soluble TL1A domains (iii) and (v) is selected from:
(a) Asp93 or Pro95
(b) (Gly/Ser) 93.

In another preferred embodiment of the present invention, the soluble TL1A domains (i), (iii) and (v) are soluble human TL1A domains. The first soluble TL1A domain (i) may be selected from native, shortened and/or mutated sequences. Thus, the first soluble TL1A domain (i) has an N-terminal sequence which may start at amino acid Asp93 or Pro95 of human TL1A, and wherein Asp93 may be replaced by a neutral amino acid, e.g. by Ser or Gly or by Gln to enable pyroglutamate formation during expression. The second and third soluble TL1A domains (iii) and (v) have a shortened N-terminal sequence which preferably starts with amino acid Lys94 or Pro95 of human TL1A (SEQ ID NO:1) and wherein Lys94 may be replaced by another amino acid, e.g. Ser or Gly.

Preferably, the N-terminal sequence of the soluble TL1A domains (iii) and (v) is selected from:
(a) Asp93 or Pro95
(b) (Gly/Ser) 94.

The soluble TL1A domain preferably ends with amino acid L251 of human TL1A. In certain embodiments, the TL1A domain may comprise internal mutations as described above.

Components (ii) and (iv) of the TL1A receptor agonist protein are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition it turned out that shorter linkers lead to single chain molecules with reduced tendency to form aggregates. Whereas linkers that are substantially longer than the ones disclosed here may exhibit unfavorable aggregations properties.

If desired, the linker may comprise an asparagine residue which may form a glycosylation site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the TL1A agonist proteins and/or in order to reduce the potential immunogenicity, it may be preferred that linker (ii) or linker (iv) or both comprise a glycosylation site.

Preferred linker sequences are shown in Table 2. A preferred linker is GSGSGNGS (SEQ ID NO: 2). Another preferred linker is GSGS (SEQ ID NO: 11).

TABLE 2

Example Linker Sequences

| SEQ ID NO | Sequence |
| --- | --- |
| 2 | GSGSGNGS |
| 3 | GSGSGSGS |
| 4 | GGSGSGSG |
| 5 | GGSGSG |
| 6 | GGSG |
| 7 | GGSGNGSG |
| 8 | GGNGSGSG |
| 9 | GGNGSG |
| 10 | GSGSGS |
| 11 | GSGS |
| 12 | GSG |

The TL1A receptor agonist protein additionally comprises an antibody Fc fragment domain which may be located N-terminal to the first TL1A domain (i) and/or C-terminal to the third TL1A domain (v). Preferably, the antibody Fc fragment domain comprises a reduced capability to interact with Fc-gamma-R receptors in vivo. Preferably, the antibody Fc fragment domain comprises or consists of an amino acid sequence as shown in SEQ ID NO: 13 or 14 (see Table 3). Sequence ID NO: 13 has N297S mutation compared to wildtype human IGG1-Fc and does not bind to Fc-gamma-R receptors. Sequence ID NO: 14 is a glycosylated (N297 wildtype) human IGG1 Fc mutein with reduced Fc-gamma-R binding capability.

TABLE 3

Examples of Fc Fragment Domains

| SEQ ID NO | Sequence |
| --- | --- |
| 13 | PAPELLGGPSVFLFPPKPKDTLMISRTPEVTCVVVDVSHEDPEVKF NWYVDGVEVHNAKTKPREEQYSSTYRVVSVLTVLHQDWLNGKEYKC KVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPGK |
| 14 | PAPPVAGPSVFLFPPKPKDTLMISRTPEVTCVVVDVSHEDPEVKFN WYVDGVEVHNAKTKPREEQYNSTYRVVSVLTVLHQDWLNGKEYKCK VSNKGLPSSIEKTISKAKGQPREPQVYTLPPSREEMTKNQVSLTCL |

TABLE 3-continued

Examples of Fc Fragment Domains

| SEQ ID NO | Sequence |
|---|---|
| | VKGFYPSDIAVEWESNGQPENNYKTTPPVLDSDGSFFLYSKLTVDK SRWQQGNVFSCSVMHEALHNHYTQKSLSLSPGK |

Number of Glycosylation Sites and In Vivo Stability

The total number of glycosylation sites and the individual position of the carbohydrates in three dimensions impacts the in-vivo stability of TL1A receptor agonist proteins. Further, carbohydrate recognition depends on local density of the terminal saccharides, the branching of the carbohydrate tree and the relative position of the carbohydrates to each other matter.

Further, partially degraded carbohydrates reduce the in vivo half-life of TL1A receptor agonist proteins through lectin-driven mechanisms. By reducing the total number of glycosylation sites and/or their relative position on the molecule's surface, the resulting compound is less accessible to these mechanisms, increasing half-life. In a preferred embodiment, the first linker (ii) is glycosylated and the second linker (iv) is not glycosylated to avoid carbohydrate patterns in close proximity on the proteins accessible surface. In a preferred embodiment, the linkers with (SEQ ID NO: 2) and (SEQ ID NO:11) are combined in one scTL1A-RBD module.

Depletion of antibody CH2-domain carbohydrates is necessary in order to avoid Fc-receptor based crosslinking in vivo and potential TL1A-receptor superclustering-based toxicity. Also, unwanted Fc-driven mechanisms like ADCC could lead to toxic events. Accordingly, in one embodiment, the overall number of glycosylation sites on the TL1A receptor agonist proteins of the instant invention is reduced through the depletion of CH2 glycosylation sites, particularly the N-glycosylation site, resulting in TL1A receptor agonist proteins comprising N297S equivalent mutations of SEQ ID NO: 15 (PROTEIN A) (according to the EU numbering system) creating aglycosl-CH2 domains. In another embodiment of the invention, one or more of the soluble TL1A domains (i), (iii), and (v) may comprise a N133 exchanged to aspartate, serine or glycine resulting in TL1A receptor agonistic fusion proteins with a further reduced number of glycosylation sites. In a preferred embodiment, the N133 [D,S,G] mutation is restricted to the soluble TL1A domains (iii) and (v) of the agonistic TL1A receptor agonistic fusion proteins of the present invention.

CH2-Domain Destabilization is Compensated by an Additional Hinge-Cysteine

CH2 (Heavy chain constant domain 2)-glycosylation present on the inner surface areas normally shields the subdomain from proteases during "open Fc-conformation transits" wherein hinge-interchain disulfide bonds are reduced and the covalent interchain linkage is disrupted (FIG. 6). This enables CH2-dissociation and exposure of the inner surface area towards proteases. TL1A receptor agonist proteins comprising an Fc-domain with a N297S equivalent mutation of SEQ ID NO: 15 (PROTEIN A) (according to the EU numbering system) creates an aglycosylated-CH2 and are therefore likely to be subject to protease digestion and less stable than equivalent structures with wild-type CH2 glycosylation. This would impact the compound's stability during USP/DSP/storage, where host cell proteases are present and have long-term access to the structure. Accordingly, in certain embodiments, the TL1A receptor agonist lacks CH2 glycosylation sites, but comprises glycosylation sites in the linker sequences of each polypeptide chain (e.g., GSGSGNGS, SEQ ID NO: 2).

According to a preferred embodiment of the invention, the antibody Fc fragment domain is fused via a hinge-linker element. The hinge-linker element has a length of 10-30 amino acids, particularly a length of 15-25 amino acids, e.g. 22 amino acids. The term "hinge-linker" includes any linker long enough to allow the domains attached by the hinge-linker element to attain a biologically active confirmation. The hinge-linker element preferably comprises the hinge-region sequence of an immunoglobulin, herein referred to as "Ig hinge-region". The term "Ig hinge-region" means any polypeptide comprising an amino acid sequence that shares sequence identity or similarity with a portion of a naturally occurring Ig hinge-region sequence which includes one or more cysteine residues, e.g., two cysteine residues, at which the disulfide bonds link the two heavy chains of the immunoglobulin.

Derivatives and analogues of the hinge-region can be obtained by mutations. A derivative or analogue as referred to herein is a polypeptide comprising an amino acid sequence that shares sequence identity or similarity with the full length sequence of the wild type (or naturally occurring protein) except that it has one or more amino acid sequence differences attributable to a deletion, insertion and/or substitution.

The number of molecules with open Fc-conformation in an individual TL1A receptor agonist protein depends on the number of interchain-disulfide bonds present in the hinge region. Accordingly, in one embodiment a third cysteine (C225 according to the EU numbering system) was introduced into the hinge region of the TL1A receptor agonist proteins of the instant invention in order to ameliorate the effect of depleting the CH2-glycosites.

Exchange of a Lysine to Glycine in the Hinge Region Results in Enhanced Proteolytic Stability In one embodiment, the TL1A receptor agonist proteins of the invention additionally comprise a mutation of the upper-hinge lysine (K223, according to the EU numbering system) to a glycine to reduce proteolytic processing at this site, thereby enhancing the overall stability of the fusion protein. Combining aforementioned introduction of a third cysteine (C225, according to the EU numbering system) with the aforementioned lysine to glycine mutation (K223G, according to the EU numbering system) within the hinge region results in an overall stabilized TL1A receptor agonist protein of the instant invention.

A particularly preferred hinge-linker element including the aforementioned cysteine (C225) and the lysine to glycine mutation (K223G) comprises or consists of the amino acid sequence as shown in SEQ ID NO: 16 (Table 4). Another particularly preferred hinge-linker element including the aforementioned cysteine (C225) and the lysine to glycine mutation (K223G) comprises or consists of the amino acid sequence as shown in SEQ ID NO: 21 (Table 4).

The interchain-disulfide connectivity of the hinge region stabilizing the homodimer of the hexavalent TL1A receptor agonist protein is also affected by the free thiol groups of the TL1A subsequences. Free thiol groups can be created through reduction of surface exposed disulfide-bridges, e.g. by reduction of the C162-C202 disulfide of TL1A. This also leads to the aforementioned open FC-conformation due to self-reduction of the hinge disulfide-bridges of the structure by the endogenous free thiols of the preparation at high protein concentrations. In consequence, single-chain TL1A-

FC fusion proteins comprising free thiols are expected to be less stable during manufacture and storage, when longtime exposure to oxygen and proteases occurs.

Therefore, to enable manufacture of a hexavalent TL1A receptor agonist at technical scale, the C162 and C202 residues are preferably mutated simultaneously to a different amino acids (e.g S, A, or G).

The TL1A receptor agonist protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. A particularly preferred N-terminal signal peptide domain comprises the amino acid sequence as shown in SEQ ID NO: 17 (Table 4).

Further, the TL1A receptor agonist protein may additionally comprise a C-terminal element, having a length of e.g. 1-50, preferably 10-30 amino acids which may include or connect to a recognition/purification domain, e.g. a FLAG domain, a Strep-tag or Strep-tag II domain and/or a poly-His domain. According to a preferred embodiment, the fusion polypeptide comprises a Strep-tag fused to the C-terminus via a short serine linker as shown in SEQ ID NO: 18 (Table 4).

Preferred hinge-linker elements (SEQ ID NO: 16, 19-24), a preferred N-terminal signal peptide domain (SEQ ID NO: 17) and serine linker-strep tag (SEQ ID NO: 18) are shown in Table 4.

TABLE 4

Exemplary domains and linkers

| SEQ ID NO | Sequence |
|---|---|
| 16 | GSSSSSSSSGSCDKTHTCPPC |
| 17 | METDTLLVFVLLVWVPAGNG |
| 18 | SSSSSSAWSHPQFEK |
| 19 | GSSSSSSSGSCDKTHTCPPC |
| 20 | GSSSSSSGSCDKTHTCPPC |
| 21 | GSSSSSGSCDKTHTCPPC |
| 22 | GSSSGSCDKTHTCPPC |
| 23 | GSSSGSCDKTHTCPPCGS |
| 24 | GSSSGSCDKTHTCPPCGSGS |

In one embodiment of the invention, the fusion polypeptide comprises three soluble TL1A domains fused by two different peptide linker elements. The first linker element (ii) consists of SEQ ID NO: 2. The second linker element (iv) consists of SEQ ID NO: 11. The first soluble TL1A domain (i) consists of amino acids D91-L251 of human TL1A according to SEQ ID NO: 1 and the soluble TL1A domains (iii) and (v) consist of amino acids P95-L251 of human TL1A according to SEQ ID NO: 1. The resulting scTL1A-RBD sequence module is shown in Table 5B SEQ ID NO: 36

In one embodiment of the invention, the fusion polypeptide comprises three soluble TL1A domains fused by two different peptide linker elements. The first linker element (ii) consists of SEQ ID NO: 2. The second linker element (iv) consists of SEQ ID NO: 11. The first soluble TL1A domain (i) consists of amino acids D93-L251 of human TL1A according to SEQ ID NO: 1 and the soluble TL1A domains (iii) and (v) consist of amino acids P95-L251 of human TL1A according to SEQ ID NO: 1. The resulting scTL1A-RBD sequence module is shown in Table 5B SEQ ID NO: 39

In another embodiment of the invention, the fusion polypeptide comprises three soluble TL1A domains fused by peptide linker elements of SEQ ID NO: 2. The first soluble TL1A domain (i) consists of amino acids D93-L251 of human TL1A according to SEQ ID NO: 1 and the soluble TL1A domains (iii) and (v) consist of amino acids K94-L251 of human TL1A according to SEQ ID NO: 1. The resulting scTL1A-RBD sequence module is shown in table 5B SEQ ID NO: 40

In another embodiment of the invention, the fusion polypeptide comprises three soluble TL1A domains fused by peptide linker elements of SEQ ID NO: 2. The first soluble TL1A domain (i) consists of amino acids D91-L251 of human TL1A according to SEQ ID NO: 1 and the soluble TL1A domains (iii) and (v) consist of amino acids D93-L251 of human TL1A according to SEQ ID NO: 1. The resulting scTL1A-RBD sequence module is shown in table 5B SEQ ID NO: 41

In another embodiment of the invention, the fusion polypeptide comprises three soluble TL1A domains fused by peptide linker elements of SEQ ID NO: 2. The first soluble TL1A domain (i) consists of amino acids D91-L251 of human TL1A according to SEQ ID NO: 1 and the soluble TL1A domains (iii) and (v) consist of amino acids D93-L251 of human TL1A according to SEQ ID NO: 1. Each of the soluble TL1A domains (I), (iii) and (v) comprise the C162S and C202S mutations simultaneously. The resulting scTL1A-RBD sequence module is shown in table 5B SEQ ID NO: 42

In one embodiment of the invention, the fusion polypeptide comprises three soluble TL1A domains fused by two different peptide linker elements. The first linker element (ii) consists of SEQ ID NO: 2. The second linker element (iv) consists of SEQ ID NO: 11. The first soluble TL1A domain (i) consists of amino acids D93-L251 of human TL1A according to SEQ ID NO: 1 and the soluble TL1A domains (iii) and (v) consist of amino acids P95-L251 of human TL1A according to SEQ ID NO: 1. Each of the soluble TL1A domains (I), (iii) and (v) comprise the C162S and C202S mutations simultaneously. The resulting scTL1A-RBD sequence module is shown in Table 5B SEQ ID NO: 43.

Preferred Configuration TL1A-Fc

Additionally, the fusion polypeptide comprises an antibody Fc fragment domain according to SEQ ID NO: 13 that is fused C-terminally to the soluble TL1A domain (v) via a hinge-linker according to SEQ ID NO: 16. The inventors surprisingly found that this particular fusion polypeptide provides improved biological activity as compared to bivalent agonistic anti-TL1A-receptor-mAB and has a prolonged stability as compared to similar fusion proteins comprising a lysine in position 223 and a N297S mutation in the CH2 domain (according to the EU numbering). The amino acid sequence of an exemplary embodiment of a TL1A receptor agonist protein of the invention is set forth in SEQ ID NO: 27.

Further, the fusion polypeptide may comprise an N-terminal signal peptide domain e.g. according to SEQ ID NO: 17. A specific example of a TL1A receptor agonist protein of the invention is shown in SEQ ID NO: 25.

According to another preferred embodiment, the fusion polypeptide may additionally comprise a C-terminal Strep-tag that is fused to the polypeptide of the invention via a short serine linker as shown in SEQ ID NO: 18. According to this aspect of the invention, the Fc fragment preferably consists of the amino acid sequence as shown in SEQ ID NO: 13 or 14.

Further, the Fc fragment may consist of a shorter Fc fragment, for example including amino acids 1-217 of SEQ ID NO: 13. Particularly preferred examples of fusion polypeptides comprising a C-terminal Strep-tag are shown in SEQ ID NO: 15 (PROTEIN A).

The exemplary TL1A receptor agonist proteins as shown in SEQ ID Nos: 15, 25, and 26, each comprises an N-terminal signal peptide domain, at amino acids 1-20 of each sequence. In each case, the mature protein starts with amino acid 21. Mature exemplary TL1A receptor agonist proteins (without a signal peptide) of the instant invention are set forth in SEQ ID NO: 27-35.

Exemplary TL1A receptor agonist proteins described above are shown in Table 5.

The TL1A receptor agonist as set forth in SEQ ID NO: 27 has a reduced total number of glycosylation sites (the N297S mutation in the CH2 region providing an aglycosylated CH2 domain, according to the EU numbering system), an increased number of inter-chain disulfide bonds in the hinge region, and the mutation of an upper-hinge lysine to a glycine (K223G, according to the EU numbering system).

Additional, the second peptide linker (iv) is shortened and the modules (iii) and (v) are N-terminal shortened, thereby reducing all in all protomer dissociation and enhancing the proteins stability towards proteases These alterations provide a decrease in potential degradation and TL1A receptor superclustering (along with concomitant toxicity).

The TL1A receptor agonist as set forth in SEQ ID NO: 30 comprises the same layout as SEQ ID NO: 27 but with the D93Q mutation in the soluble TL1A domains (i) thereby enabling formation of pyroglutamate leading to protection of the N-terminus against aminopeptidases and subsequently enhancing the overall stability of the protein during manufacture and storage.

The TL1A receptor agonist as set forth in SEQ ID NO: 32 comprises the same layout as SEQ ID NO: 30 but with the third peptide linker (vi) shortened to reduce the interdomain distance between the soluble TL1A domain (v) and the Fc-domain (Vii) thereby enhancing the proteins stability towards proteases.

According to one embodiment of the invention, the single-chain TL1A fusion polypeptide domain comprises a scTL1A-RBD module as shown in SEQ ID NO: 39 optionally with the soluble domain (i) comprising the D93Q mutation. A specific example of a TL1A receptor agonist protein of the invention comprising the D93Q mutein in domain (i), the hinge linker of SEQ ID NO: 16 and an antibody Fc fragment according to SEQ ID NO: 13 is shown in SEQ ID NO: 30

TABLE 5

Exemplary TL1A receptor agonist proteins

| SEQ ID NO | Sequence |
|---|---|
| 25<br>PROTEIN A<br>without Strep | METDTLLVFVLLVWVPAGNGDKPRAHLTVVRQTPTQHFKNQFPALHWEHELGLAFTKN<br>RMNYTNKFLLIPESGDYFIYSQVTFRGMTSECSEIRQAGRPNKPDSITVVITKVTDSY<br>PEPTQLLMGTKSVCEVGSNWFQPIYLGAMFSLQEGDKLMVNVSDISLVDYTKEDKTFF<br>GAFLLGSGSGNGSPRAHLTVVRQTPTQHFKNQFPALHWEHELGLAFTKNRMNYTNKFL<br>LIPESGDYFIYSQVTFRGMTSECSEIRQAGRPNKPDSITVVITKVTDSYPEPTQLLMG<br>TKSVCEVGSNWFQPIYLGAMFSLQEGDKLMVNVSDISLVDYTKEDKTFFGAFLLGSGS<br>PRAHLTVVRQTPTQHFKNQFPALHWEHELGLAFTKNRMNYTNKFLLIPESGDYFIYSQ<br>VTFRGMTSECSEIRQAGRPNKPDSITVVITKVTDSYPEPTQLLMGTKSVCEVGSNWFQ<br>PIYLGAMFSLQEGDKLMVNVSDISLVDYTKEDKTFFGAFLLGSSSSSSSGSCDKTHT<br>CPPCPAPELLGGPSVFLFPPKPKDTLMISRTPEVTCVVVDVSHEDPEVKFNWYVDGVE<br>VHNAKTKPREEQYSSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPVLD<br>SDGSFFLYSKLTVDKSRWQQGNVFSCSVMHEALHNHYTQKSLSLSPGK |
| 15<br>PROTEIN A<br>SEQ 39 +<br>SEQ 13 (FC) +<br>Signal +<br>Strep | METDTLLVFVLLVWVPAGNGDKPRAHLTVVRQTPTQHFKNQFPALHWEHELGLAFTKN<br>RMNYTNKFLLIPESGDYFIYSQVTFRGMTSECSEIRQAGRPNKPDSITVVITKVTDSY<br>PEPTQLLMGTKSVCEVGSNWFQPIYLGAMFSLQEGDKLMVNVSDISLVDYTKEDKTFF<br>GAFLLGSGSGNGSPRAHLTVVRQTPTQHFKNQFPALHWEHELGLAFTKNRMNYTNKFL<br>LIPESGDYFIYSQVTFRGMTSECSEIRQAGRPNKPDSITVVITKVTDSYPEPTQLLMG<br>TKSVCEVGSNWFQPIYLGAMFSLQEGDKLMVNVSDISLVDYTKEDKTFFGAFLLGSGS<br>PRAHLTVVRQTPTQHFKNQFPALHWEHELGLAFTKNRMNYTNKFLLIPESGDYFIYSQ<br>VTFRGMTSECSEIRQAGRPNKPDSITVVITKVTDSYPEPTQLLMGTKSVCEVGSNWFQ<br>PIYLGAMFSLQEGDKLMVNVSDISLVDYTKEDKTFFGAFLLGSSSSSSSGSCDKTHT<br>CPPCPAPELLGGPSVFLFPPKPKDTLMISRTPEVTCVVVDVSHEDPEVKFNWYVDGVE<br>VHNAKTKPREEQYSSTYRVVSVLTVLHQDWLNGKEYKCKVSNKALPAPIEKTISKAKG<br>QPREPQVYTLPPSREEMTKNQVSLTCLVKGFYPSDIAVEWESNGQPENNYKTTPPVLD<br>SDGSFFLYSKLTVDKSRWQQGNVFSCSVMHEALHNHYTQKSLSLSPGSSSSSSAWSHP<br>QFEK |
| 26<br>SEQ 39 +<br>SEQ 14 (FC) +<br>Signal<br>No Step | METDTLLVFVLLVWVPAGNGDKPRAHLTVVRQTPTQHFKNQFPALHWEHELGLAFTKN<br>PMNYTNKFLLIPESGDYFIYSQVTFRGMTSECSEIRQAGRPNKPDSITVVITKVTDSY<br>PEPTQLLMGTKSVCEVGSNWFQPIYLGAMFSLQEGDKLMVNVSDISLVDYTKEDKTFF<br>GAFLLGSGSGNGSPRAHLTVVRQTPTQHFKNQFPALHWEHELGLAFTKNRMNYTNKFL<br>LIPESGDYFIYSQVTFRGMTSECSEIRQAGRPNKPDSITVVITKVTDSYPEPTQLLMG<br>TKSVCEVGSNWFQPIYLGAMFSLQEGDKLMVNVSDISLVDYTKEDKTFFGAFLLGSGS<br>PRAHLTVVRQTPTQHFKNQFPALHWEHELGLAFTKNRMNYTNKFLLIPESGDYFIYSQ<br>VTFRGMTSECSEIRQAGRPNKPDSITVVITKVTDSYPEPTQLLMGTKSVCEVGSNWFQ<br>PIYLGAMFSLQEGDKLMVNVSDISLVDYTKEDKTFFGAFLLGSSSSSSSGSCDKTHT<br>CPPCPAPPVAGPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKGLPSSIEKTISKAKGQ |

TABLE 5-continued

Exemplary TL1A receptor agonist proteins

| SEQ ID NO | Sequence |
|---|---|
| | PREPQVYTLPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| 27<br>SEQ 39 +<br>SEQ 13 (FC)<br>No Signal<br>No Strep<br>No Glyco | DKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSPRAHLTV<br>VRQTPTQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPIYLGAM<br>FSLQEGDKLMVNVSDISLVDYTKEDKTFFGAFLLGSGSPRAHLTVVRQTPTQHFKNQF<br>PALHWEHELGLAFTKNRMNYTNKFLLIPESGDYFIYSQVTFRGMTSECSEIRQAGRPN<br>KPDSITVVITKVTDSYPEPTQLLMGTKSVCEVGSNWFQPIYLGAMFSLQEGDKLMVNV<br>SDISLVDYTKEDKTFFGAFLLGSSSSSSSSGSCDKTHTCPPCPAPELLGGPSVFLFPP<br>KPKDTLMISRTPEVTCVVVDVSHEDPEVKFNWYVDGVEVHNAKTKPREEQYSSTYRVV<br>SVLTVLHQDWLNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSKLTVDKSRWQQ<br>GNVFSCSVMHEALHNHYTQKSLSLSPGK |
| 28<br>SEQ 39 +<br>SEQ 13 (FC)<br>No Signal +<br>StrepTag<br>No Glyco | DKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSPRAHLTV<br>VRQTPTQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPIYLGAM<br>FSLQEGDKLMVNVSDISLVDYTKEDKTFFGAFLLGSGSPRAHLTVVRQTPTQHFKNQF<br>PALHWEHELGLAFTKNRMNYTNKFLLIPESGDYFIYSQVTFRGMTSECSEIRQAGRPN<br>KPDSITVVITKVTDSYPEPTQLLMGTKSVCEVGSNWFQPIYLGAMFSLQEGDKLMVNV<br>SDISLVDYTKEDKTFFGAFLLGSSSSSSSSGSCDKTHTCPPCPAPELLGGPSVFLFPP<br>KPKDTLMISRTPEVTCVVVDVSHEDPEVKFNWYVDGVEVHNAKTKPREEQYSSTYRVV<br>SVLTVLHQDWLNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSKLTVDKSRWQQ<br>GNVFSCSVMHEALHNHYTQKSLSLSPGSSSSSSAWSHPQFEK |
| 29<br>SEQ 39 +<br>SEQ 14 (FC)<br>No Signal<br>No strep<br>Glyco FC | DKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSPRAHLTV<br>VRQTPTQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPIYLGAM<br>FSLQEGDKLMVNVSDISLVDYTKEDKTFFGAFLLGSGSPRAHLTVVRQTPTQHFKNQF<br>PALHWEHELGLAFTKNRMNYTNKFLLIPESGDYFIYSQVTFRGMTSECSEIRQAGRPN<br>KPDSITVVITKVTDSYPEPTQLLMGTKSVCEVGSNWFQPIYLGAMFSLQEGDKLMVNV<br>SDISLVDYTKEDKTFFGAFLLGSSSSSSSSGSCDKTHTCPPCPAPPVAGPSVFLFPPK<br>PKDTLMISRTPEVTCVVVDVSHEDPEVKFNWYVDGVEVHNAKTKPREEQYNSTYRVVS<br>VLTVLHQDWLNGKEYKCKVSNKGLPSSIEKTISKAKGQPREPQVYTLPPSREEMTKNQ<br>VSLTCLVKGFYPSDIAVEWESNGQPENNYKTTPPVLDSDGSFFLYSKLTVDKSRWQQG<br>YVFSCSVMHEALHNHYTQKSLSLSPGK |
| 30<br>Same as 27<br>with D93Q in<br>module 1 | QKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSPRAHLTV<br>VRQTPTQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPIYLGAM<br>FSLQEGDKLMVNVSDISLVDYTKEDKTFFGAFLLGSGSPRAHLTVVRQTPTQHFKNQF<br>PALHWEHELGLAFTKNRMNYTNKFLLIPESGDYFIYSQVTFRGMTSECSEIRQAGRPN<br>KPDSITVVITKVTDSYPEPTQLLMGTKSVCEVGSNWFQPIYLGAMFSLQEGDKLMVNV<br>SDISLVDYTKEDKTFFGAFLLGSSSSSSSSGSCDKTHTCPPCPAPELLGGPSVFLFPP<br>KPKDTLMISRTPEVTCVVVDVSHEDPEVKFNWYVDGVEVHNAKTKPREEQYSSTYRVV<br>SVLTVLHQDWLNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSKLTVDKSRWQQ<br>GNVFSCSVMHEALHNHYTQKSLSLSPGK |
| 31<br>SEQ 40<br>With L1 8mer<br>L2: 8mer | DKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSKPRAHLT<br>VVRQTPTQHFKNQFPALHWEHELGLAFTKNRMNYTNKFLLIPESGDYFIYSQVTFRGM<br>TSECSEIRQAGRPNKPDSITVVITKVTDSYPEPTQLLMGTKSVCEVGSNWFQPIYLGA<br>MFSLQEGDKLMVNVSDISLVDYTKEDKTFFGAFLLGSGSGNGSKPRAHLTVVRQTPTQ<br>HFKNQFPALHWEHELGLAFTKNRMNYTNKFLLIPESGDYFIYSQVTFRGMTSECSEIR<br>QAGRPNKPDSITVVITKVTDSYPEPTQLLMGTKSVCEVGSNWFQPIYLGAMFSLQEGD<br>KLMVNVSDISLVDYTKEDKTFFGAFLLGSSSSSSSSGSCDKTHTCPPCPAPELLGGPS<br>VFLFPPKPKDTLMISRTPEVTCVVVDVSHEDPEVKFNWYVDGVEVHNAKTKPREEQYS<br>STYRVVSVLTVLHQDWLNGKEYKCKVSNKALPAPIEKTISKAKGQPREPQVYTLPPSR<br>EEMTKNQVSLTCLVKGFYPSDIAVEWESNGQPENNYKTTPPVLDSDGSFFLYSKLTVD<br>KSRWQQGNVFSCSVMHEALHNHYTQKSLSLSPGK |

TABLE 5-continued

Exemplary TL1A receptor agonist proteins

| SEQ ID NO | Sequence |
|---|---|
| 32<br>Same as 30 shortened hinge | QKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSPRAHLTV<br>VRQTPTQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPIYLGAM<br>FSLQEGDKLMVNVSDISLVDYTKEDKTFFGAFLLGSGSGNGSPRAHLTVVRQTPTQHFKNQF<br>PALHWEHELGLAFTKNRMNYTNKFLLIPESGDYFIYSQVTFRGMTSECSEIRQAGRPN<br>KPDSITVVITKVTDSYPEPTQLLMGTKSVCEVGSNWFQPIYLGAMFSLQEGDKLMVNV<br>SDISLVDYTKEDKTFFGAFLLGSSSSGSCDKTHTCPPCPAPELLGGPSVFLFPPKPK<br>DTLMISRTPEVTCVVVDVSHEDPEVKFNWYVDGVEVHNAKTKPREEQYSSTYRVVSVL<br>TVLHQDWLNGKEYKCKVSNKALPAPIEKTISKAKGQPREPQVYTLPPSREEMTKNQVS<br>LTCLVKGFYPSDIAVEWESNGQPENNYKTTPPVLDSDGSFFLYSKLTVDKSRWQQGNV<br>FSCSVMHEALHNHYTQKSLSLSPGK |
| 33<br>SEQ 42 +<br>Fc13 | DGDKPRAHLTVVRQTPTQHFKNQFPALHWEHELGLAFTKNRMNYTNKFLLIPESGDYF<br>IYSQVTFRGMTSEsSEIRQAGRPNKPDSITVVITKVTDSYPEPTQLLMGTKSVsEVGS<br>NWFQPIYLGAMFSLQEGDKLMVNVSDISLVDYTKEDKTFFGAFLLGSGSGNGSDGDKP<br>RAHLTVVRQTPTQHFKNQFPALHWEHELGLAFTKNRMNYTNKFLLIPESGDYFIYSQV<br>TFRGMTSEsSEIRQAGRPNKPDSITVVITKVTDSYPEPTQLLMGTKSVsEVGSNWFQP<br>IYLGAMFSLQEGDKLMVNVSDISLVDYTKEDKTFFGAFLLGSGSGNGSDGDKPRAHLT<br>VVRQTPTQHFKNQFPALHWEHELGLAFTKNRMNYTNKFLLIPESGDYFIYSQVTFRGM<br>TSEsSEIRQAGRPNKPDSITVVITKVTDSYPEPTQLLMGTKSVsEVGSNWFQPIYLGA<br>MFSLQEGDKLMVNVSDISLVDYTKEDKTFFGAFLLGSSSSSSSGSCDKTHTCPPCPA<br>PELLGGPSVFLFPPKPKDTLMISRTPEVTCVVVDVSHEDPEVKFNWYVDGVEVHNAKT<br>KPREEQYSSTYRVVSVLTVLHQDWLNGKEYKCKVSNKALPAPIEKTISKAKGQPREPQ<br>VYTLPPSREEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| 34<br>Protein A with shorter hinge linker | DKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSPRAHLTV<br>VRQTPTQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPIYLGAM<br>FSLQEGDKLMVNVSDISLVDYTKEDKTFFGAFLLGSGSPPAHLTVVRQTPTQHFKNQF<br>PALHWEHELGLAFTKNRMNYTNKFLLIPESGDYFIYSQVTFRGMTSECSEIRQAGRPN<br>KPDSITVVITKVTDSYPEPTQLLMGTKSVCEVGSNWFQPIYLGAMFSLQEGDKLMVNV<br>SDISLVDYTKEDKTFFGAFLLGSSSSGSCDKTHTCPPCPAPELLGGPSVFLFPPKPK<br>DTLMISRTPEVTCVVVDVSHEDPEVKFNWYVDGVEVHNAKTKPREEQYSSTYRVVSVL<br>TVLHQDWLNGKEYKCKVSNKALPAPIEKTISKAKGQPREPQVYTLPPSREEMTKNQVS<br>LTCLVKGFYPSDIAVEWESNGQPENNYKTTPPVLDSDGSFFLYSKLTVDKSRWQQGNV<br>FSCSVMHEALHNHYTQKSLSLSPGK |
| 35<br>Protein A without Streptag with C162S and C202S | DKPRAHLTVVRQTPTQHFKNQFPALHWEHELGLAFTKNRMNYTNKFLLIPESGDYFIY<br>SQVTFRGMTSEsSEIRQAGRPNKPDSITVVITKVTDSYPEPTQLLMGTKSVsEVGSNW<br>FQPIYLGAMFSLQEGDKLMVNVSDISLVDYTKEDKTFFGAFLLGSGSGNGSPPAHLTV<br>VRQTPTQHFKNQFPALHWEHELGLAFTKNRMNYTNKFLLIPESGDYFIYSQVTFRGMT<br>SEsSEIRQAGRPNKPDSITVVITKVTDSYPEPTQLLMGTKSVsEVGSNWFQPIYLGAM<br>FSLQEGDKLMVNVSDISLVDYTKEDKTFFGAFLLGSGSPRAHLTVVRQTPTQHFKNQF<br>PALHWEHELGLAFTKNRMNYTNKFLLIPESGDYFIYSQVTFRGMTSEsSEIRQAGRPN<br>KPDSITVVITKVTDSYPEPTQLLMGTKTVsEVGSNWFQPIYLGAMFSLQEGDKLMVNV<br>SDISLVDYTKEDKTFFGAFLLGSSSSSSSGSCDKTHTCPPCPAPELLGGPSVFLFPP<br>KPKDTLMISRTPEVTCVVVDVSHEDPEVKFNWYVDGVEVHNAKTKPREEQYSSTYRVV<br>SVLTVLHQDWLNGKEYKCKVSNKALPAPIEKTISKAKGQPREPQVYTLPPSREEMTKN<br>QVSLTCLVKGFYPSDIAVEWESNGQPENNYKTTPPVLDSDGSFFLYSKLTVDKSRWQQ<br>GNVFSCSVMHEALHNHYTQKSLSLSPGK |

TABLE 5B

Exemplary scTL1A-RBD modules

| 36<br>D91-P95-P95<br>L1 8mer<br>L2 4mer | DGDKPRAHLTVVRQTPTQHFKNQFPALHWEHELGLAFTKNRMNYTNKFLLIPESGDYF<br>IYSQVTFRGMTSECSEIRQAGRPNKPDSITVVITKVTDSYPEPTQLLMGTKSVCEVGS<br>NWFQPIYLGAMFSLQEGDKLMVNVSDISLVDYTKEDKTFFGAFLLGSGSGNGSPRAHL<br>TVVRQTPTQHFKNQFPALHWEHELGLAFTKNRMNYTNKFLLIPESGDYFIYSQVTFRG<br>MTSECSEIRQAGRPNKPDSITVVITKVTDSYPEPTQLLMGTKSVCEVGSNWFQPIYLG<br>AMFSLQEGDKLMVNVSDISLVDYTKEDKTFFGAFLLGSGSPRAHLTVVRQTPTQHFKN<br>QFPALHWEHELGLAFTKNRMNYTNKFLLIPESGDYFIYSQVTFRGMTSECSEIRQAGR<br>PNKPDSITVVITKVTDSYPEPTQLLMGTKSVCEVGSNWFQPIYLGAMFSLQEGDKLMV<br>NVSDISLVDYTKEDKTFFGAFLL |

TABLE 5B-continued

Exemplary scTL1A-RBD modules

| | |
|---|---|
| 39<br>D93-P95-P95<br>L1 8mer<br>L2 4mer | DKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FWPIYLGAMFSLQEGDKLMVNVSDISLVDYTKEDKTFFGAFLLGSGSGNGSPPAHLTV<br>VRQTPTQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPIYLGAM<br>FSLQEGDKLMVNVSDISLVDYTKEDKTFFGAFLLGSGSPRAHLTVVRQTPTQHFKNQF<br>PALHWEHELGLAFTKNRMNYTNKFLLIPESGDYFIYSQVTFRGMTSECSEIRQAGRPN<br>KPDSITVVITKVTDSYPEPTQLLMGTKSVCEVGSNWFQPIYLGAMFSLQEGDKLMVNV<br>SDISLVDYTKEDKTFFGAFLL |
| 40<br>D93-K94-K94<br>L1 8mer<br>L2 8mer | DKPRAHLTVVRQTPTQHFKNQFPALHWEHELGLAFTKNRMNYTNKFLLIPESGDYFIY<br>SQVTFRGMTSECSEIRQAGRPNKPDSITVVITKVTDSYPEPTQLLMGTKSVCEVGSNW<br>FQPIYLGAMFSLQEGDKLMVNVSDISLVDYTKEDKTFFGAFLLGSGSGNGSKPRAHLT<br>VVRQTPTQHFKNQFPALHWEHELGLAFTKNRMNYTNKFLLIPESGDYFIYSQVTFRGM<br>TSECSEIRQAGRPNKPDSITVVITKVTDSYPEPTQLLMGTKSVCEVGSNWFQPIYLGA<br>MFSLQEGDKLMVNVSDISLVDYTKEDKTFFGAFLLGSGSGNGSKPRAHLTVVRQTPTQ<br>HFKNQFPALHWEHELGLAFTKNRMNYTNKFLLIPESGDYFIYSQVTFRGMTSECSEIR<br>QAGRPNKPDSITVVITKVTDSYPEPTQLLMGTKSVCEVGSNWFQPIYLGAMFSLQEGD<br>KLMVNVSDISLVDYTKEDKTFFGAFLL |
| 41<br>D91-D93-D93<br>C162S and<br>C202S and<br>variation of<br>linker length | DGDKPRAHLTVVRQTPTQHFKNQFPALHWEHELGLAFTKNRMNYTNKFLLIPESGDYF<br>IYSQVTFRGMTSECSEIRQAGRPNKPDSITVVITKVTDSYPEPTQLLMGTKSVCEVGS<br>NWFQPIYLGAMFSLQEGDKLMVNVSDISLVDYTKEDKTFFGAFLLGSGSGNGSDGDKP<br>RAHLTVVRQTPTQHFKNQFPALHWEHELGLAFTKNRMNYTNKFLLIPESGDYFIYSQV<br>TFRGMTSECSEIRQAGRPNKPDSITVVITKVTDSYPEPTQLLMGTKSVCEVGSNWFQP<br>IYLGAMFSLQEGDKLMVNVSDISLVDYTKEDKTFFGAFLLGSGSGNGSDGDKPRAHLT<br>VVRQTPTQHFKNQFPALHWEHELGLAFTKNRMNYTNKFLLIPESGDYFIYSQVTFRGM<br>TSECSEIRQAGRPNKPDSITVVITKVTDSYPEPTQLLMGTKSVCEVGSNWFQPIYLGA<br>MFSLQEGDKLWVNVSDISLVDYTKEDKTFFGAFLL |
| 42 C182S and<br>C202S mutein<br>of Seq 41 | DGDKPRAHLTVVRQTPTQHFKNQFPALHWEHELGLAFTKNRMNYTNKFLLIPESGDYF<br>IYSQVTFRGMTSEsSEIRQAGRPNKPDSITVVITKVTDSYPEPTQLLMGTKSVsEVGS<br>NWFQPIYLGAMFSLQEGDKLMVNVSDISLVDYTKEDKTFFGAFLLGSGSGNGSDGDKP<br>RAHLTVVRQTPTQHFKNQFPALHWEHELGLAFTKNRMNYTNKFLLIPESGDYFIYSQV<br>TFRGMTSEsSEIRQAGRPNKPDSITVVITKVTDSYPEPTQLLMGTKSVsEVGSNWFQP<br>IYLGAMFSLQEGDKLMVNVSDISLVDYTKEDKTFFGAFLLGSGSGNGSDGDKPRAHLT<br>VVRQTPTQHFKNQFPALHWEHELGLAFTKNRMNYTNKFLLIPESGDYFIYSQVTFRGM<br>TSEsSEIRQAGRPNKPDSITVVITKVTDSYPEPTQLLMGTKSVsEVGSNWFQPIYLGA<br>MFSLQEGDKLMVNVSDISLVDYTKEDKTFFGAFLL |
| 43<br>D93-P95-P95 | DKPRAHLTVVRQTPTQHFKNQFPALHWEHELGLAFTKNRMNYTNKFLLIPESGDYFIY<br>SQVTFRGMTSEsSEIRQAGRPNKPDSITVVITKVTDSYPEPTQLLMGTKSVsEVGSNW<br>FQPIYLGAMFSLQEGDKLMVNVSDISLVDYTKEDKTFFGAFLLGSGSGSPRAHLTV<br>VRQTPTQHFKNQFPALHWEHELGLAFTKNRMNYTNKFLLIPESGDYFIYSQVTFRGMT<br>SEsSEIRQAGRPNKPDSITVVITKVTDSYPEPTQLLMGTKSVsEVGSNWFQPIYLGAM<br>FSLQEGDELMVNVSDISLVDYTKEDKTFFGAFLLGSGSPRAHLTVVRQTPTQHFKNQF<br>PALHWEHELGLAFTKNRMNYTNKFLLIPESGDYFIYSQVTFRGMTSEsSEIRQAGRPN<br>KPDSITVVITKVTDSYPEPTQLLMGTKSVsEVGSNWFQPIYLGAMFSLQEGDKLMVNV<br>SDISLVDYTKEDKTFFGAFLL |

Furthermore, it has to be noted that the scTL1A-RBD module (SEQ ID NO: 39) is well suited to generate fusion proteins with additional domains fused to either N- or C-terminal end employing the linkers described in Table 2 (SEQ ID NO: 2-12).

Above presented embodiments of the TL1A receptor agonist proteins of the invention either address stability influencing construction principles or aggregation resistance of soluble receptor agonist proteins of the invention or modulate receptor binding and activity of the receptor agonist proteins.

A further important property for describing suitability of a substance as an active agent in medical preparations is its pharmacokinetic profile (PK profile) Pharmacokinetics is the study of drug disposition in the body and focuses on the changes in drug plasma concentration. For any given drug and dose, the plasma concentration will vary depending on the processes of absorption, distribution and elimination. The time dependent decline of plasma drug concentration and its final elimination from the body mainly depends on biotransformation and excretion of the drug and is generally measured as in vivo half-life time (Pharmacology, 4th Edition; Elesevier 2013).

Understanding the course of events that make up the immune response against a pathogen or a tumor allows to determine advantageous PK profiles of the TL1A receptor agonist proteins of the invention. The immune response against a pathogen or indeed a tumor carrying antigens can be divided into several phases. Each phase shows a characteristic duration and events usually take place in specialized tissues. In particular, the priming phase describes early events in an immune response when lymphocytes are being presented with tumor-associated antigens in secondary lymphoid organs. In order to recognize antigens through their T cell or B cell receptor, T cells and B cells, respectively, need to form cell-cell conjugates with antigen-presenting cells (APC). In case of successful antigen-recognition, lymphocytes are also being presented with co-stimulatory molecules such as TL1A by the APC. As both presentation of antigen and co-stimulatory molecules occurs at the interface of the APC/lymphocyte conjugate, this interaction is rather short lived as the conjugate falls apart after several minutes or very few hours. Following antigen recognition and co-stimulation with molecules such as TL1A lymphocytes become activated and enter the expansion phase during which they proliferate in order to mount an immune response against the tumor.

In light of the short physical interaction of APCs and lymphocytes in secondary lymphoid organs, one could speculate that the co-stimulatory signal elicited by recombinant biologics targeting the TL1A-Receptor pathway is desired to be short-lived. In fact, long exposition to co-stimulatory signals might push lymphocytes into a hyper-activated state possibly leading to systemic toxic effects. Consequently, a favorable PK profile for biologics targeting co-stimulatory pathways of the immune system would show a comparably short terminal half-life in the range of hours or possibly one day. This would be in contrast to antibodies targeting the same pathways, which usually show a terminal half-life of multiple days or even more than one week. In summary, biologics activating co-stimulatory pathways of the immune system having a half-life in the range of several hours are closer to the natural ligand in term of their temporal activity in comparison to stimulating antibodies. This could also make a positive contribution to possible toxicity effects observed during the treatment with some immune-stimulating antibodies. Thus, in a further embodiment the TL1A receptor agonist proteins of the invention have a short terminal half live such as less than 4 days, less than three days, less than two days, less than one day.

A further aspect of the present invention relates to a nucleic acid molecule encoding a TL1A receptor agonist protein as described herein. The nucleic acid molecule may be a DNA molecule, e.g. a double-stranded or single-stranded DNA molecule, or an RNA molecule. The nucleic acid molecule may encode the TL1A receptor agonist protein or a precursor thereof, e.g. a pro- or pre-proform of the TL1A receptor agonist protein which may comprise a signal sequence or other heterologous amino acid portions for secretion or purification which are preferably located at the N- and/or C-terminus of the TL1A receptor agonist protein. The heterologous amino acid portions may be linked to the first and/or second domain via a protease cleavage site, e.g. a Factor X3, thrombin or IgA protease cleavage site. A specific example of a nucleic acid sequence of the invention is shown in Table 6 as SEQ ID NO: 37. This nucleic acid molecule comprises the open reading frame encoding the fusion polypeptide of SEQ ID NO: 25.

TABLE 6

Nucleic Acid Sequence of Exemplary TL1A receptor agonist protein

| SEQ ID NO | Sequence |
|---|---|
| 37 | AAGCTTTAGGGATAACAGGGTAATAGCCGCCACCATGGAGACTGACACCCTGCTGGTGTTCG<br>TGCTGCTGGTCTGGGTGCCTGCAGGAAATGGAGACAAGCCAAGAGCACACTTGACCGTGGTG<br>CGACAGACACCTACCCAGCATTTTAAGAATCAATTCCCTGCTCTCCACTGGGAGCACGAGCT<br>GGGTCTGGCCTTTACAAAGAACAGAATGAACTACACTAACAAATTTCTGCTGATCCCTGAAT<br>CTGGGGATTATTTCATCTATTCTCAGGTGACATTTCGGGGAATGACTTCAGAGTGCTCAGAA<br>ATTCGTCAGGCTGGAAGGCCTAATAAGCCCGACAGCATCACGGTCGTTATTACCAAAGTGAC<br>AGATTCTTATCCAGAACCAACTCAGCTGCTGATGGGTACCAAGAGCGTTTGCGAAGTGGGCA<br>GCAACTGGTTCCAGCCCATCTATCTGGGTGCTATGTTTTCTCTGCAAGAGGGCGATAAACTC<br>ATGGTCAATGTGAGTGACATTTCTCTTGTGGATTACACTAAGGAGGATAAGACCTTCTTCGG<br>TGCATTCCTGCTGGGCTCAGGATCTGGCAATGGGAGTCCTAGAGCCCATCTCACAGTCGTGA<br>GGCAGACCCCAACTCAGCACTTCAAGAACCAGTTCCCCGCCCTGCATTGGGAGCACGAACTG<br>GGTCTTGCATTCACCAAGAACAGGATGAATTACACCAATAAGTTCCTGTTGATACCCGAATC<br>CGGAGACTACTTTATCTACTCCCAAGTCACCTTTCGCGGCATGACTTCTGAATGCAGCGAAA<br>TCCGGCAGGCTGGTCGCCCCAACAAGCCCGATTCCATCACTGTAGTGATCACCAAGGTAACA<br>GACAGCTACCCTGAACCCACGCAGCTCCTCATGGGCACCAAAAGTGTGTGTGAAGTCGGCAG<br>CAATTGGTTTCAGCCCATTTATCTCGGCGCCATGTTTTCACTTCAGGAGGGTGATAAACTGA<br>TGGTCAACGTTTCCGACATTAGCCTCGTTGACTACACAAAGGAAGATAAAACTTTCTTCGGG<br>GCTTTCCTGCTGGGGTCCGGAAGTCCCCGAGCCCACTTGACAGTCGTTCGTCAAACGCCAAC<br>ACAGCACTTTAAGAATCAGTTTCCAGCCCTTCATTGGGAGCATGAGTTGGGGCTGGCATTTA<br>CTAAGAATCGCATGAACTATACCAACAAATTCCTGCTGATCCCAGAGAGTGGGGATTACTTT<br>ATCTACAGCCAAGTGACATTTCGAGGCATGACTAGCGAGTGTTCCGAGATTCGGCAGGCCGG<br>AAGGCCCAACAAGCCTGATTCCATTACCGTGGTCATAACTAAGGTAACAGACTCCTATCCAG<br>AGCCTACCCAGCTTTTGATGGGGACCAAATCCGTTTGTGAGGTGGGCTCAAACTGGTTTCAA<br>CCCATATACCTTGGAGCCATGTTCTCCTTGCAGGAGGGAGACAAACTGATGGTGAATGTGTC<br>TGACATCAGTCTGGTAGACTATACCAAAGAGGACAAAACATTCTTTGGCGCTTTCCTCCTGG<br>GATCCtcgagTTCATCGTCCTCATCCGGCTCATGTGATAAGACCCACACCTGCCCTCCCTGT<br>CCTGCCCCTGAGCTGCTGGGCGGACCTTCTGTGTTCCTGTTCCCCCCCAAGCCTAAGGACAC<br>CCTGATGATCTCCAGGACCCCTGAGGTGACCTGTGTGGTGGTGGACGTGTCTCACGAAGATC<br>CCGAGGTGAAGTTCAACTGGTACGTGGACGGCGTGGAGGTCCACAACGCCAAGACCAAGCCT<br>AGGGAGGAGCAGTACAGCTCCACCTACCGGGTGGTGTCTGTGCTGACCGTGCTGCACCAGGA<br>TTGGCTGAACGGAAAGGAGTATAAGTGTAAGGTCTCCAACAAGGCCCTGCCTGCCCCCATCG<br>AGAAAACCATCTCCAAGGCCAAGGGCCAGCCTCGGGAGCCTCAGGTGTACACCCTGCCTCCT<br>AGCAGGGAGGAGATGACCAAGAACCAGGTGTCCCTGACCTGTCTGGTGAAGGGCTTCTACCC<br>TTCCGATATCGCCGTGGAGTGGGAGTCTAATGGCCAGCCCGAGAACAACTACAAGACCACCC<br>CTCCTGTGCTGGACTCTGACGGCTCCTTCTTCCTGTACTCCAAGCTGACCGTGGACAAGTCC<br>AGATGGCAGCAGGGCAACGTGTTCTCCTGCTCCGTGATGCACGAGGCCCTGCACAATCACTA<br>CACCCAGAAGTCCCTGTCTCTGAGTCCGGGCAAGTAATAggcgcgcc |

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosomal integration vector, etc. Examples of suitable expression control sequences and vectors are described for example by Sambrook et al. (1989) Molecular Cloning, A Laboratory Manual, Cold Spring Harbor Press, and Ausubel et al. (1989), Current Protocols in Molecular Biology, John Wiley & Sons or more recent editions thereof.

Various expression vector/host cell systems may be used to express the nucleic acid sequences encoding the TL1A receptor agonist proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells. Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical or diagnostic composition comprising as the active agent at least one TL1A receptor agonist protein, a respective nucleic acid encoding therefore, or a transformed or transfected cell, all as described herein.

In another aspect, the present invention provides a pharmaceutical composition comprising a TL1A receptor agonist protein disclosed herein and one or more pharmaceutically acceptable carriers, diluents, excipients, and/or adjuvants.

In another aspect, the present invention provides a nucleic acid molecule encoding the TL1A receptor agonist protein. In another embodiment, the present invention provides an expression vector comprising the nucleic acid molecule. In another embodiment, the present invention provides a cell comprising the nucleic acid molecule. In a further embodiment, the cell is a eukaryotic cell. In another embodiment, the cell is a mammalian cell. In another embodiment, the cell is a Chinese Hamster Ovary (CHO) cell. In other embodiments, the cell is selected from the group consisting of CHO-DBX11, CHO-DG44, CHO-S, and CHO-K1 cells. In other embodiments, the cell is selected from the group consisting of Vero, BHK, HeLa, COS, MDCK, HEK-293, NIH-3T3, W138, BT483, Hs578T, HTB2, BT20, T47D, NS0, CRL7030, HsS78Bst, PER.C6, SP2/0-Agl4, and hybridoma cells.

In another aspect, the present invention provides a method of treating a subject having a TL1A-associated disease or disorder, the method comprising administering to the subject an effective amount of the TL1A receptor agonist protein. In one embodiment, the TL1A receptor agonist protein is administered alone. In another embodiment, the TL1A receptor agonist protein is administered before, concurrently, or after the administration of a second agent. In another embodiment, the disease or disorder is selected from the group consisting of: tumors, infectious diseases, inflammatory diseases, metabolic diseases, autoimmune disorders, degenerative diseases, apoptosis-associated diseases, and transplant rejections. In one embodiment, the tumors are solid tumors. In one embodiment, the tumors arise from the group of cancers consisting of sarcoma, esophageal cancer, and gastric cancer. In another embodiment, the tumors arise from Ewing's sarcoma or fibrosarcoma, In another embodiment, the tumors arise from the group of cancers consisting of Non-Small Cell Lung Carcinoma (NSCLC), pancreatic cancer, colorectal cancer, breast cancer, ovarian cancer, head and neck cancers, and Small Cell Lung Cancer (SCLC). In another embodiment, the tumors are lymphatic tumors. In one embodiment, the tumors are hematologic tumors. In another embodiment, the tumors arise from non-Hodgkin's lymphoma, leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), or hairy cell leukemia. In another embodiment, the autoimmune disorders are rheumatoid diseases, arthritic diseases, or rheumatoid and arthritic diseases. In a further embodiment, the disease or disorder is rheumatoid arthritis. In another embodiment, the degenerative disease is a neurodegenerative disease. In a further embodiment, the neurodegenerative disease is multiple sclerosis.

In one embodiment, the second agent is a chemotherapeutic, radiotherapeutic, or biological agent. In one embodiment, the second agent is selected from the group consisting of Duvelisib, Ibrutinib, Navitoclax, and Venetoclax, In another embodiment, the second agent is an apoptotic agent. In one embodiment, the apoptotic second agent is selected from the group consisting of Bortezomib, Azacitidine, Dasatinib, and Gefitinib. In a particular embodiment, the pharmaceutical compositions disclosed herein are administered to a patient by intravenous or subcutaneous administration. In other embodiments, the disclosed pharmaceutical compositions are administered to a patient byoral, parenteral, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In one embodiment, the TL1A receptor agonist protein is administered as a single bolus. In another embodiment, TL1A receptor agonist protein may be administered over several divided doses. The TL1A receptor agonist protein can be administered at about 0.1-100 mg/kg. In one embodiment, the TL1A receptor agonist protein can be administered at a dosage selected from the group consisting of: about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, and 10-100 mg/kg. In other embodiments, the TL1A receptor agonist protein is present in pharmaceutical compositions at about 0.1-100 mg/ml. In one embodiment, the TL1A receptor agonist protein is present in pharmaceutical compositions at an amount selected from the group consisting of: about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml. In other embodiments, a therapeutically effective amount of TL1A receptor agonist protein is administered to a subject. In another embodiment, a prophylactically effective amount of TL1A receptor agonist protein is administered to a subject.

The term "TL1A-associated disease or disorder" as used herein is any disease or disorder which may be ameliorated by administering an effective amount of a TL1A receptor agonist to a subject in need thereof. At least one TL1A receptor agonist protein, respective nucleic acid encoding therefore, or transformed or transfected cell, all as described herein may be used in therapy, e.g., in the prophylaxis and/or treatment of disorders caused by, associated with and/or accompanied by dysfunction of TL1A, particularly proliferative disorders, such as tumors, e.g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of TL1A" as used herein is to be understood as any function or expression of TL1A that deviates from the normal function or expression of TL1A, e.g., overexpression of the TL1A gene or protein, reduced or abolished expression of the TL1A gene or protein compared to the normal physiological expression level of TL1A, increased activity of TL1A, reduced or abolished activity of TL1A, increased binding of TL1A to any binding partners, e.g., to a receptor, particularly a TL1A receptor or another cytokine molecule, reduced or abolished binding to any binding partner, e.g. to a receptor, particularly a TL1A receptor or another cytokine molecule, compared to the normal physiological activity or binding of TL1A.

In various embodiments, a method is provided for treating a human subject suffering from a disorder which can be treated by targeting TL1A-receptors comprising administering to the human subject a TL1A receptor agonist protein disclosed herein such that the effect on the activity of the target, or targets, in the human subject is agonistic, one or more symptoms is alleviated, and/or treatment is achieved. The TL1A receptor agonist proteins provided herein can be used to treat humans suffering from primary and metastatic cancers, including carcinomas of breast, colon, rectum, lung (e.g., small cell lung cancer "SCLC" and non-small cell lung cancer "NSCLC"), oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, DLBCL, follicular lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

A pharmaceutical composition comprising a TL1A receptor agonist protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule modulator or an immune checkpoint inhibitor (including but not limited to anti-B7.1, anti-B7.2, anti-B7.3, anti-B7.4, anti-CD28, anti-B7RP1, CTLA4-Ig, anti-CTLA-4, anti-PD-1, anti-PD-L1, anti-PD-L2, anti-ICOS, anti-LAG-3, anti-Tim3, anti-VISTA, anti-Pro95, anti-BTLA, LIGHT fusion protein, anti-CD137, anti-CD137L, anti-OX40, anti-OX40L, anti-CD70, anti-CD27, anti-CD27L, anti-GAL9, anti-A2AR, anti-KIR, anti-IDO-1, anti-CD20), a dendritic cell/antigen-presenting cell modulator (including but not limited to anti-CD40 antibody, anti-CD40L, anti-DC-SIGN, anti-Dectin-1, anti-CD301, anti-CD303, anti-CD123, anti-CD207, anti-DNGR1, anti-CD205, anti-DCIR, anti-CD206, anti-ILT7), a modulator for Toll-like receptors (including but not limited to anti-TLR-1, anti-TLR-2, anti-TLR-3, anti-TLR-4, anti-TLR-4, anti-TLR-5, anti-TLR-6, anti-TLR-7, anti-TLR-8, anti-TLR-9), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, or an anti-IL-6/cytokine receptor antibody), a bispecific redirected T cell or NK cell cytotoxicity (including but not limited to a BiTE®), a chimeric T cell receptor (CAR-T) based therapy, a T cell receptor (TCR)-based therapy, a therapeutic cancer vaccine, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

In an embodiment, a method of treating a cancer or in the prevention or inhibition of metastases from the tumors described herein, the TL1A receptor agonist protein(s) can be used alone or in combination with one or more additional agents, e.g., a chemotherapeutic, radiotherapy, or biological agent. In some embodiments, the agent can include the following: 13-cis-Retinoic Acid; 2-CdA; 2-Chlorodeoxyadenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil®; Afinitor®; Agrylin@; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Arimidex®; Aromasin®; Arranon®; Arsenic Trioxide; Arzerram; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome@; Duralone®; Duvelisib; Efudex®; Eligard™; Ellence™; Eloxatin™; Elspar®; Emcyt®; Epirubicin; Epoetin Alfa; Erbitux; Erlotinib; Erwinia L-asparaginase; Estramustine; Ethyol Etopophos®; Etoposide; Etoposide Phosphate; Eulexin®; Everolimus; Evista®;

Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar, Gleevecm; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibrutinib; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; ipilimumab, Iressa®; Irinotecan; Isotretinoin; Ixabepilone; Ixempra™; KADCYCLA®; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Lirilumab; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®, Medrol®; Megace®; Megestrol; Megestrol Acetate; MEK inhibitors; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navitoclax; Navelbine®; Nelarabine; Neosar®; Neulastam; Neumega®; Neupogen®; Nexavar®; Nilandron®; Nilotinib; Nilutamide; Nipent®; Nitrogen Mustard Novaldex®; Nivolumab; Novantrone® Nplate; Octreotide; Octreotide acetate; Ofatumumab; Oncospar®; Oncovin®; Ontak®; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pembrolizumab; Pentostatin; Pertuzumab; Phenylalanine Mustard; Pidilizumab; Platinol®; Platinol-AQ®; Prednisolone; Prednisone; Prelone®; Procarbazine; PROCRIT®; Proleukin®; Prolifeprospan 20 with Carmustine Implant; Purinethol®; BRAF inhibitors; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Cortef®; Solu-Medrol®; Sorafenib; SPRYCEL™; STI-571; STIVAGRA™, Streptozocin; SU11248; Sunitinib; Sutent®; Tamoxifen Tarceva®; Targretin®; Tasigna®; Taxol®; Taxotere®; Temodar® Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®, Tremelimumab; Tretinoin; Trexall™; Trisenox®; TSPA; TYKERB®; Urelumab; VCR; Vectibix™; Velban®; Velcade®; Venetoclax; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; ZevalinT; Zinecard®; Zoladex®; Zoledronic acid; Zolinza; or Zometa®, and/or any other agent not specifically listed here that target similar pathways.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more than one, or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In various embodiments, pharmaceutical compositions comprising one or more TL1A receptor agonist proteins, either alone or in combination with prophylactic agents, therapeutic agents, and/or pharmaceutically acceptable carriers are provided herein. In various embodiments, nonlimiting examples of the uses of the pharmaceutical compositions disclosed herein include diagnosing, detecting, and/or monitoring a disorder, preventing, treating, managing, and/or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

As used herein, the phrase "effective amount" means an amount of TL1A agonist protein that results in a detectable improvement (e.g., at least about 5%, 10%, 15%, 20%, 25%, 30%, 35%, 40%, 45%, 50%, 55%, 60%, 65%, 70%, 75%, or more from baseline) in one or more parameters associated with a dysfunction of TL1A or with a TL1A-associated disease or disorder.

Methods of administering a therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a TL1A receptor agonist protein provided herein is about 0.1-100 mg/kg, (e.g., about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the TL1A receptor agonist protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

EXAMPLES

Example 1. Manufacture of a TL1A Receptor Agonist Protein

A) Amino acids Met1-Gly20
Ig-Kappa-signal peptide, assumed signal peptidase cleavage site after amino acid Gly 20.
B) Amino acids Asp21-Leu179
First soluble cytokine domain of the human TL1A (TL1A, amino acid 93-251 of SEQ ID NO: 1).
C) Amino acids Gly180-Ser 187
First peptide linker element of SEQ ID NO: 2.
D) Amino acids Pro188-Leu344
Second soluble cytokine domain of the human TL1A (TL1A, amino acid 95-251 of SEQ ID NO: 1).
E) Amino acids Gly345-Ser348.
Second peptide linker element of SEQ ID NO: 11.
F) Amino acids Pro349-Leu505
Third soluble cytokine domain of the human TL1A (TL1A, amino acid 95-251 of SEQ ID NO: 1).
G) Amino acids Gly506-Cys526
Hinge-linker element of SEQ ID NO: 16.
H) Amino acids Pro527-Lys744
Antibody Fc fragment domain of SEQ ID NO: 13.

The above TL1A receptor agonist protein is shown in SEQ ID NO: 25.

The indicated linkers may be replaced by other preferred linkers, e.g. as shown in SEQ ID NOs: 3-12.

The indicated Hinge-linker element may be replaced by other preferred Hinge-linkers, e.g. as shown in SEQ ID NOs: 19-24.

It should be noted that the first and second peptide linkers do not need to be identical.

The signal peptide sequence (A) may be replaced by any other suitable, e.g. mammalian signal peptide sequence The above TL1A receptor agonist protein is shown in SEQ ID NO: 25.

The indicated linkers may be replaced by other preferred linkers, e.g. as shown in SEQ ID NOs: 3-12.

The indicated Hinge-linker element may be replaced by other preferred Hinge-linkers, e.g. as shown in SEQ ID NOs: 19-24.

It should be noted that the first and second peptide linkers do not need to be identical.

The signal peptide sequence (A) may be replaced by any other suitable, e.g. mammalian signal peptide sequence.

1.2 Gene Cassette Encoding the Polypeptide

The synthetic gene may be optimized in view of its codon usage for the expression in suitable host cells, e.g. insect cells or mammalian cells. A preferred nucleic acid sequence is shown in SEQ ID NO: 37.

Example 2. Expression and Purification 2.1 Cloning, Expression and Purification of Fusion Polypeptides The aforementioned fusion proteins are expressed recombinantly in two different eukaryotic host cells employing the methods described below:

Method for Small Scale Expression of TL1A Receptor Agonist Fusion Proteins:

For initial analysis of aforementioned TL1A receptor agonist fusion proteins, Hek293 cells grown in DMEM+GlutaMAX (GibCo) supplemented with 10% FBS, 100 units/ml Penicillin and 100 [mu]g/ml Streptomycin are transiently transfected with a plasmid containing an expression cassette for a fusion polypeptide and an appropriate selection marker, e.g. a functional expression cassette comprising a blasticidine, puromycin or hygromycin resistance gene. In those cases, where a plurality of polypeptide chains is necessary to achieve the final product, the expression cassettes will be either combined on one plasmid or positioned on different plasmids during the transfection. Cell culture supernatant containing recombinant fusion polypeptide will be harvested three days post transfection and clarified by centrifugation at 300×g followed by filtration through a 0.22 μm sterile filter.

Method for Large Scale Expression and Purification of TL1A Receptor Agonist Fusion Proteins For larger scale expression of TL1A receptor agonist fusion proteins to be used in vivo, synthetic DNA cassettes encoding the aforementioned proteins is inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome. The sequence verified expression vectors are introduced by electroporation into suspension adapted Chinese Hamster Ovary cells (CHO-S, Invitrogen). Appropriate selection pressure will be applied three days post-transfection to the transfected cells. Surviving cells carrying the vector derived resistance gene(s) are recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants are analyzed by ELISA-assays detecting the aforementioned proteins and the cell pools with the highest specific productivity which were expanded in shake flasks prior to protein production (orbital shaker, 100 rpm, shaking throw 50 mm).

For lab-scale protein production, individual cell pools are cultured for 7-12 days in chemically defined medium (PowerCHO2-CD, Lonza) at 37° C. and 7% CO2 atmosphere in a Wave bioreactor 20/50 EHT (GE-Healthcare). The basal medium is PowerCHO2-CD supplemented with 4 mM Glutamax. Wave culture is started with a viable cell concentration of 0.3 to 0.4×10e6 cells/ml and the following settings (for a five- or ten liter bag): shaking frequency 18 rpm, shaking ankle 7°, gas current 0.2-0.3 L/min, 7% CO2, 36.5° C. During the Wave run, the cell culture is fed twice with PowerFeed A (Lonza), usually on day 2 (20% feed) and day 5 (30% feed). After the second feed, shaking frequency is increased to 22 rpm, as well as the shaking ankle to 8°.

The bioreactor is usually harvested in between day 7 to day 12 when the cell viability drops below 80%. First, the culture supernatant is clarified using a manual depth filtration system (Millipore Millistak Pod, MCOHC 0.054 m$^2$). For Strep-tagged proteins, Avidin is added to a final concentration of 0.5 mg/L. Finally, the culture supernatant containing the TL1A receptor agonist fusion protein is sterile filtered using a bottle top filter (0.22 µm, PES, Corning) and stored at 2-8° C. until further processing.

For affinity purification Streptactin Sepharose is packed to a column (gel bed 2 ml), equilibrated with 15 ml buffer W (100 mM Tris-HCl, 150 mM NaCl, pH 8.0) or PBS pH 7.4 and the cell culture supernatant is applied to the column with a flow rate of approx. 4 ml/min. Subsequently, the column is washed with 15 ml buffer W and bound polypeptide is eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternatively to the Streptactin Sepharose based method, the affinity purification is performed employing a column with immobilized Protein-A as affinity ligand and an Äkta chromatography system (GE-Healthcare). A solid phase material with high affinity for the FC-domain of the fusion protein was chosen: MABSelect Sure™ (GE Healthcare). Briefly, the clarified cell culture supernatant is loaded on a HiTrap MabSelectSure column (CV=5 ml) equilibrated in wash-buffer-1 (20 mM Pi, 95 mM NaCl, pH7.2) not exceeding a load of 10 mg fusion protein per ml column-bed. The column is washed with ten column-volumes (10CV) of aforementioned equilibration buffer followed by four column-volumes (4CV) of wash-buffer-2 (20 mM Pi, 95 mM NaCl, pH 8.0) to deplete host-cell protein and host-cell DNA. The column is then eluted with elution buffer (20 mM Pi, 95 mM NaCl, pH 3.5) and the eluate is collected in up to ten fractions with each fraction having a volume equal to column-bed volume (5 ml). Each fraction is neutralized with an equal volume of aforementioned wash-buffer-2. The linear velocity is set to 150 cm/h and kept constant during the aforementioned affinity chromatography method. The protein amount of the eluate fractions is quantitated and peak fractions are concentrated by ultrafiltration and further purified by size exclusion chromatography (SEC).

For determination of the apparent molecular weight of purified fusion polypeptide under native conditions a Superdex 200 column is loaded with standard proteins of known molecular weight. Based on the elution volume of the standard proteins a calibration curve is plotted and the apparent molecular weight of purified fusion polypeptide is determined. The FC-domain comprising TL1A receptor agonist fusion proteins typically elutes from the Superdex200 columns with an apparent molecular weight of approx. 160-180 kDa confirming the homodimerization of the mature TL1A receptor agonist fusion polypeptides by the Fc domain.

Example 4. Trivalent Control Protein

To compare the relative binding between hexavalent TL1A receptor agonist fusion proteins and the, trivalent TL1A-RBD stabilized with bacteriophage RB69-FOLDON, PROTEIN X (SEQ ID NO: 38) was expressed in CHO-S cells and purified as described in the former section. The SEC-purified protein is served as control in the following Examples. The sequence of PROTEIN X (SEQ ID NO: 38) is shown in Table 7. Amino-acids 1-20 of PROTEIN X represent the signal peptide and the mature proteins starts with amino acid Glu51. This protein consists of three identical polypeptides each comprising one soluble TL1A domain (E91-L251 of SEQ ID NO: 1); this assembly stabilized by the trimerization domain of bacteriophage RB69 fibritin fused with a flexible linker to the C-terminus of TL1A.

TABLE 7

| Trivalent control protein including a signal peptide | |
|---|---|
| SEQ ID NO | Sequence |
| 38 (Protein X) | METDTLLVFVLLVWVDKPRAHLTVVRQTPTQHFKNQFPALHWEHELGLAFTKNPM NYTNKFLLIPESGDYFIYSQVTFRGMTSECSEIRQAGRPNKPDSITVVITKVTDS YPEPTQLLMGTKSVCEVGSNWFQPIYLGAMFSLQEGDKLMVNVSDISLVDYTKED KTFFGAFLLGSGSSGSSGSSGSGYIEDAPSDGKFYVRKDGAWVELPTASGPSSSS SSAWSHPQFEK. |

Example 5: Determination of the In Vitro Stability of TL1A Receptor Agonist Proteins by Limited Protease Digestion All TL1A receptor agonist proteins to be investigated will be expressed and purified as hexavalent Fc-Fusion protein as described in Example 1. The set will include TL1A receptor agonist proteins comprising the N297S mutation [according to the EU numbering system] in the CH2-domain and a hinge region that enables the formation of three disulfide bridges and additionally lack the upper hinge lysine [K223, according to the EU numbering system] which is mutated to glycine [K223G]. In a limited protease digestion assay, the aforementioned TL1A receptor agonist proteins comprising the N297S mutation and the K223G mutation simultaneously in context of a three disulfide enabling hinge will be compared to TL1A receptor agonist proteins comprising the N297S mutation but have the K223 wildtype present either in the context of a two disulfide or three disulfide enabling hinge region.

In addition, TL1A receptor agonist proteins with the second linker element (iv) reduced to 4 amino-acids and the shortened hinge element (vi) will be investigated (e.g. SEQ ID NO: 32 and 34). Both engineering strategies (N297S combined with K223G mutation in context of a three-disulfide enabling hinge region) and shortage of linker elements (iv and vi) have a potential impact on the stability of the respective molecules.

The stability of different TL1A agonistic proteins of the present invention can be addressed by limited protease digestion in vitro. For this analysis, the aforementioned TL1A receptor agonist proteins are incubated with low concentrations of proteases (e.g. Trypsin, V8 protease) at different temperatures (e.g. 4° C., 25° C., 37° C.) for different amounts of time. Quantification of specific proteolytic fragments and their appearance over time can be subsequently measured by different methods, like SDS-PAGE, analytical SEC or analytical Mass-Spectrometry methods known in the art (e.g Nano-RP-HPLC-ESI-MSMS). As the investigated proteins have most of their sequences in common, the faster appearance and enlarged quantities of specific proteolytic fragments from individual proteins over time can then be used to judge their relative stability and rank them to each other. With regard to protease based decoy kinetics of the aforementioned TL1A receptor agonist proteins investigated, the following order regarding their proteolytic stability is to be expected:

The TL1A receptor agonist proteins comprising the N297S and the K223G and the three-disulfide enabling hinge region simultaneously have a prolonged stability as compared to the TL1A receptor agonist proteins comprising the N297S and wildtype K223 in the hinge region. The TL1A receptor agonist proteins comprising the SEQ ID NO: 21 as hinge linker have a prolonged stability as compared to TL1A receptor agonist proteins comprising the SEQ ID NO: 16 as hinge linker element.

The results show that PROTEIN A has a surprisingly short terminal half-life in mice. This short half-life constitutes a favorable therapeutic option since a short co-stimulatory stimulus with TL1A receptor agonist proteins is desirable.

Example 7: Stability/Aggregation Test

The contents of monomers and aggregates are determined by analytical SEC as described in Example 2. For this particular purpose the analysis is performed in buffers containing physiological salt concentrations at physiological pH (e.g. 0.9% NaCl, pH 7.4; PBS pH 7.4). A typical aggregation analysis is done on a Superdex200 column (GE Healthcare). This column separates proteins in the range between 10 to 800 kDa.

For determination of the apparent molecular weight of purified fusion polypeptide under native conditions a Superdex 200 column is loaded with standard proteins of known molecular weight. Based on the elution volume of the standard proteins a calibration curve is plotted and the apparent molecular weight of purified fusion proteins of unknown molecular weight is calculated based on the elution volume.

SEC analysis of soluble, non-aggregated protein typically shows a distinct single protein peak at a defined elution volume (measured at OD at 280 nm or at OD 214 nm). This elution volume corresponds to the apparent native molecular weight of the particular protein. With regard to the definition of "monomer" in the case of FC-fusion proteins, the assembly of two polypeptide-chains is driven by the FC-part of the protein and the functional unit is a protein consisting of two chains. This unit that contains two FC-linked polypeptide chains is defined as "monomer" in the case of Fc-fusion proteins regardless of being a dimerized single-chain fusion polypeptide.

If protein aggregation occurs, the SEC analysis shows additional protein peaks with lower retention volumes. Protein oligomers potentially serve as aggregation seeds and a high content of oligomers potentially leads to aggregation of the protein. Oligomers of large molecular weight and aggregates elute in the void volume of the Superdex200 column and cannot be analyzed by SEC with respect to their native molecular weight.

Purified preparations of TL1A receptor agonist fusion proteins should preferably contain only defined monomeric protein and only a very low amount of oligomeric protein. The degree of aggregation/oligomerization of a particular TL1A receptor agonist fusion protein preparation is determined on basis of the SEC analysis by calculating the peak areas of the OD280 diagram for the defined monomer and the oligomer/aggregate fraction, respectively. Based on the total peak area the percentage of defined monomer protein is calculated as follows:

monomer content [%]=[Peak area monomer protein]/ [Total peak area]×100)

Example 8: Determination of the Equilibrium Binding Constants for Tri- and Hexavalent TL1A-Receptor Ligand Constructs by QCM Analysis The equilibrium binding constants ($K_D$) of trivalent and hexavalent PROTEIN X and PROTEIN A are calculated based on kinetic binding data ($k_{on}$ and $k_{off}$) that are determined with an automated biosensor system (Attana A100). The A100 allows to investigate molecular interactions in real-time based on the Quartz Crystal Microbalance (QCM) technique.

For this purpose, the human TL1A-receptor is immobilized to the surface of a carboxyl-activated QCM-chip. Subsequently the tri- or hexavalent PROTEIN X or PROTEIN A, respectively, is used as an analyte at different concentrations (e.g. 0.5, 1, 2, 5, and µg/ml) for analyzing the kinetic binding data for ligand-receptor binding ($k_{on}$) and dissociation ($k_{off}$). The analysis is done in real time and the respective $K_D$ can be calculated: $K_D=k_{off}/k_{on}$.

The QCM analysis shows that the trivalent PROTEIN X binds to the respective immobilized TL1A-receptor with a $K_D$ in the low nM-range with an expected $K_D$ of 1-100 nm. However, hexavalent constructs of PROTEIN A show a higher binding affinity in the pM-range towards the respective immobilized TL1A-receptor with an expected $K_D$ of 1-1000 pM. A common characteristic of the kinetic binding data ($k_{on}$ and $k_{off}$) is that the hexavalent constructs show faster $k_{on}$ in comparison to the trivalent constructs. In addition, slower dissociation ($k_{off}$) is commonly observed for the hexavalent ligands if compared to the trivalent ligand.

Example 9: TL1A Receptor Agonist Combined with TCR Activation Leads to Cytokine Production by Human T Cells Primary human T cells are magnetically purified from buffy coat preparations using negative selection. Cells suspensions are adjusted to a concentration of 1×10e5 cells per ml and cells are seeded in 24-well plates, which are pre-coated with an anti-human CD3 antibody alone or in combination with an anti-human CD28 antibody. The cells are then treated with or without varying amounts of TL1A receptor agonist and incubated at 37° C. for 24 h, 48 h or 72 h. After each time point cells are separated from culture supernatant and the latter is used in an ELISA assay to measure the production of the cytokines IFNγ and GMCSF by the T cells.

Regarding the production of both cytokines by primary human T cells one expects to see a supplementary effect exerted by the anti-human CD28 antibody when comparing results to T cells incubated in wells pre-coated only with anti-human CD3 antibody. Importantly, T cells produce significantly more IFNγ and GMCSF when TL1A receptor agonist is present in the culture medium. This demonstrates a strong supplementary effect exerted by TL1A receptor agonist and implies a role for TL1A in T cell activation.

Example 10: TL1A Receptor Agonist Induces Caspase Activation in the Human Erythroleukemic Line TF-1

The human TF-1 cell line is seeded at 75,000 cells per well in black 96-well plates with clear bottom in RPMI medium containing 1% v/v fetal bovine serum. Cell are treated with varying amounts of TL1A receptor agonist in the presence or absence of cycloheximide (1-100 μg/ml) for 6 hours. Caspase activity is measured directly in the wells by adding an equal volume of a lysis buffer containing 1-50 μg/ml DEVD-rodamine 110 and allowing the reaction to proceed at 37° C. for 1 to 3 hours. Release of rodamine 110 is monitored on a fluorescence plate reader (excitation 485 nm; emission 535 nm).

Caspase activation correlates with the rodamine 110 signal strength measured using the fluorescence plate reader. In TF-1 cells TL1A receptor agonist is able to efficiently trigger Caspase activity in a dose-dependent manner in the presence of cycloheximide as supposed to cells that were not co-incubated with cycloheximide. As the rodamine 110 signal strength correlates to the TL1A receptor agonist concentration used, this indicates that TL1A receptor agonist indeed activated Caspases in TF-1 cells.

Example 11: TL1A Receptor Agonist Induces Apoptosis in the Human Erythroleukemic Line TF-1

The human TF-1 cell line is seeded at 1×105 cells per well in 24-well plates in RPMI medium containing 1% v/v fetal bovine serum. Cell are treated with varying amounts of TL1A receptor agonist in the presence or absence of cycloheximide (1-100 μg/ml) for 24 h, 48 h or 72 h. At each time point cells are harvested and processed for flow cytometric analysis assessing the binding of Propidium Iodide (PI) to double-stranded nucleic acids such as DNA and the upregulation of Annexin V. Both binding of PI and Annexin V upregulation are critical indicators for the induction of apoptotic cell death.

One expects to observe a supplementary effect exerted by TL1A receptor agonist in a sense that it will significantly increase the PI and Annexin V double-positive cell populations when cells are treated with both cycloheximide and TL1A receptor agonist. Compared to cells incubated with cycloheximide or TL1A receptor agonist alone the combination of both agents leads to a higher percentage of PI and Annexin V positive TF-1 cells. This implies that TL1A receptor agonist can drive TF-1 cells into apoptosis in the presence of cycloheximide.

The invention claimed is:

1. A TL1A receptor agonist protein comprising a single-chain fusion polypeptide comprising:
   (i) a first soluble TL1A domain,
   (ii) a first peptide linker,
   (iii) a second soluble TL1A domain,
   (iv) a second peptide linker, and
   (v) a third soluble TL1A domain, and
   (vi) a hinge-linker selected from the group comprising SEQ ID NOs: 16 and 19-24, and
   (vii) an antibody Fc fragment, wherein the antibody Fc fragment consists of the amino acid sequence as shown in SEQ ID NO: 13 or amino acids 1-217 of SEQ ID NO: 13, wherein the soluble TL1A domains (i), (iii) and (v) consist of amino acids Asp91-Leu251 of human TL1A according to SEQ ID NO: 1.

2. A TL1A receptor agonist protein comprising a single-chain fusion polypeptide comprising the amino acid sequence of any one of SEQ ID NOs: 15, 25, 27, 28, and 30-35.

3. The TL1A receptor agonist protein of claim 2, which additionally comprises an N-terminal signal peptide domain, or a protease cleavage site, or a C-terminal element comprising a recognition or a purification domain.

4. The TL1A receptor agonist protein of claim 2, comprising two polypeptides each having the amino acid sequence as set forth in SEQ ID NOs: 27, or 30-35.

5. The TL1A receptor agonist protein of claim 4, wherein the two polypeptides are covalently linked through three interchain disulfide bonds formed at:
   a) positions 497, 503 and 506 of SEQ ID NO: 27, 30, 35, or
   b) positions 503, 509, and 512 of SEQ ID NO: 31, or
   c) positions 494, 500, and 503 of SEQ ID NO: 32 and 34, or
   d) positions 511, 517, and 520 of SEQ ID NO: 33.

6. The TL1A receptor agonist protein of claim 4, comprising one or more N-glycosylated asparagine residues selected from the group of N132 and N266 of NO: 27 and 30, or N128 and N257 of SEQ ID NO: 31, or N128 and N258 of SEQ ID NO: 32, or N122 and N245 of SEQ ID NO: 33, or N129 and N260 of SEQ ID NO: 34, or N125 and N250 of SEQ ID NO: 35.

7. The TL1A receptor agonist protein of claim 2, wherein the polypeptide is further post-translationally modified.

8. The TL1A receptor agonist protein of claim 7, wherein the post-translational modification comprises modification of the N-terminal glutamine to pyroglutamate.

9. A pharmaceutical or diagnostic composition comprising as an active agent the TL1A receptor agonist protein of claim 2, and one or more pharmaceutically acceptable carriers, diluents, excipients and/or adjuvants.

10. A nucleic acid molecule encoding the TL1A receptor agonist protein of claim 2, in operative linkage with an expression control sequence.

11. An expression vector comprising the nucleic acid molecule of claim 10.

* * * * *